US010946098B2

(12) United States Patent
Bruchez et al.

(10) Patent No.: US 10,946,098 B2
(45) Date of Patent: Mar. 16, 2021

(54) ACTIVATABLE TWO-COMPONENT PHOTOSENSITIZERS

(71) Applicant: Carnegie Mellon University, Pittsburgh, PA (US)

(72) Inventors: Marcel P. Bruchez, Pittsburgh, PA (US); Jianjun He, Changsha (CN); Yi Wang, Jamaica Plain, MA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 16/568,886

(22) Filed: Sep. 12, 2019

(65) Prior Publication Data

US 2020/0078460 A1    Mar. 12, 2020

Related U.S. Application Data

(62) Division of application No. 15/527,061, filed as application No. PCT/US2015/061051 on Nov. 17, 2015, now Pat. No. 10,434,177.

(Continued)

(51) Int. Cl.
*A61K 41/00*    (2020.01)
*A61K 47/64*    (2017.01)
(Continued)

(52) U.S. Cl.
CPC .......... *A61K 41/0057* (2013.01); *A61K 47/64* (2017.08); *A61N 5/062* (2013.01);
(Continued)

(58) Field of Classification Search
None
See application file for complete search history.

(56) References Cited

U.S. PATENT DOCUMENTS

| 4,215,050 A | 7/1980 | Lantzsch |
| 4,355,023 A | 10/1982 | Ehrlich et al. |

(Continued)

FOREIGN PATENT DOCUMENTS

| EP | 0043075 A2 | 1/1982 |
| EP | 0368684 A1 | 5/1990 |

(Continued)

OTHER PUBLICATIONS

Ferguson et al. Journal of the Society of Dyers and Colourists (1973), 89(1), 22-4 (Derwent abstract provided).*

(Continued)

*Primary Examiner* — Clinton A Brooks
(74) *Attorney, Agent, or Firm* — The Webb Law Firm

(57) ABSTRACT

Provided herein is a two-component photosensitizer, which demonstrated robust and selective killing effects for transfected HEK cells and affibody targeted A431 cancer cells when exposed to near infrared light excitation. Free MG2I is a pure and stable fluorogen; it is easy to synthesize and modify, and has no toxicity to cells. Unlike conventional photosensitizers, the dye and FAP itself has no photosensitizing effect until they are bound. Also unlike other activation methods, the activation step is achieved by adding the fluorogen, not the presence of the targeted molecule, requiring an 'active' activation instead of a 'passive' activation. This method offers the ability to locally switch-on and selective generation of singlet oxygen at the target site and can be used for a wide variety of molecular targets.

14 Claims, 19 Drawing Sheets

Specification includes a Sequence Listing.

Related U.S. Application Data

(60) Provisional application No. 62/123,489, filed on Nov. 17, 2014.

(51) Int. Cl.

| | |
|---|---|
| *C07C 211/43* | (2006.01) |
| *C07C 233/36* | (2006.01) |
| *C07C 233/40* | (2006.01) |
| *C09B 11/10* | (2006.01) |
| *A61N 5/06* | (2006.01) |
| *C07K 14/00* | (2006.01) |
| *C07K 14/71* | (2006.01) |
| *C09B 11/22* | (2006.01) |

(52) U.S. Cl.
CPC .......... *C07C 211/43* (2013.01); *C07C 233/36* (2013.01); *C07C 233/40* (2013.01); *C07K 14/001* (2013.01); *C07K 14/71* (2013.01); *C09B 11/10* (2013.01); *C09B 11/22* (2013.01); *A61N 2005/0659* (2013.01); *C07K 2317/622* (2013.01); *C07K 2319/035* (2013.01); *C07K 2319/30* (2013.01)

(56) References Cited

U.S. PATENT DOCUMENTS

| | | |
|---|---|---|
| 4,462,334 A | 7/1984 | Kim |
| 4,704,962 A | 11/1987 | Healey |
| 4,745,051 A | 5/1988 | Smith et al. |
| 4,946,778 A | 8/1990 | Ladner et al. |
| 5,096,815 A | 3/1992 | Ladner et al. |
| 5,166,320 A | 11/1992 | Wu et al. |
| 5,198,346 A | 3/1993 | Ladner et al. |
| 5,223,409 A | 6/1993 | Ladner et al. |
| 5,270,163 A | 12/1993 | Gold et al. |
| 5,475,096 A | 12/1995 | Gold et al. |
| 5,496,938 A | 3/1996 | Gold et al. |
| 5,567,588 A | 10/1996 | Gold et al. |
| 5,580,737 A | 12/1996 | Polisky et al. |
| 5,591,828 A | 1/1997 | Bosslet et al. |
| 5,637,459 A | 6/1997 | Burke et al. |
| 5,660,985 A | 8/1997 | Pieken et al. |
| 5,683,867 A | 11/1997 | Biesecker et al. |
| 5,702,892 A | 12/1997 | Mulligan-Kehoe |
| 5,707,796 A | 1/1998 | Gold et al. |
| 5,750,373 A | 5/1998 | Garrard et al. |
| 5,763,189 A | 6/1998 | Buechler et al. |
| 5,821,047 A | 10/1998 | Garrard et al. |
| 5,948,635 A | 9/1999 | Kay et al. |
| 6,127,132 A | 10/2000 | Breitling et al. |
| 6,131,580 A | 10/2000 | Ratner et al. |
| 6,248,558 B1 | 6/2001 | Lin et al. |
| 6,407,213 B1 | 6/2002 | Carter et al. |
| 9,249,306 B2 | 2/2016 | Bruchez et al. |
| 2003/0165918 A1 | 9/2003 | Nakamura et al. |
| 2003/0165961 A1 | 9/2003 | Lee |
| 2003/0220502 A1 | 11/2003 | Waggoner et al. |
| 2004/0262585 A1 | 12/2004 | Cummins et al. |
| 2006/0029936 A9 | 2/2006 | Lee |
| 2007/0254323 A1 | 11/2007 | Wang et al. |
| 2008/0213811 A1 | 9/2008 | Vogel et al. |
| 2010/0124788 A1 | 5/2010 | Sieber |
| 2011/0159519 A1 | 6/2011 | Schmidt et al. |
| 2013/0244891 A1 | 9/2013 | Waggoner et al. |

FOREIGN PATENT DOCUMENTS

| | | |
|---|---|---|
| JP | 6447381 A | 2/1989 |
| JP | 8503994 A | 4/1996 |
| JP | 9104825 A | 4/1997 |
| JP | 2003508065 A | 3/2003 |
| WO | 8801649 | 3/1988 |
| WO | 9106306 | 5/1991 |
| WO | 9119813 A1 | 12/1991 |
| WO | 9206180 A1 | 4/1992 |
| WO | 9219749 A1 | 11/1992 |
| WO | 9220316 A2 | 11/1992 |
| WO | 9222635 A1 | 12/1992 |
| WO | 9304701 A1 | 3/1993 |
| WO | 9311161 A1 | 6/1993 |
| WO | 03014743 A2 | 2/2003 |
| WO | 2004025268 A2 | 3/2004 |
| WO | 2008092041 A2 | 7/2008 |
| WO | 2010096388 A2 | 8/2010 |

OTHER PUBLICATIONS

Jacobsen et al. Trends Cell Biol. Sep. 2008; 18(9): 443-450.*
Babendure et al., "Aptamers Switch on Fluorescence of Triphenylmethane Dyes", Journal of the American Chemical Society, 2003, pp. 14716-14717, vol. 125.
Berlier et al., "Quantitative Comparison of Long-wavelength Alexa Fluor Dyes to Cy Dyes; Fluorescence of the Dyes and Their Bioconjugates", Journal of Histochemistry and Cytochemistry, 2003, pp. 1699-1712, vol. 51, No. 12.
Bielinska et al., "The interaction of plasmid DNA with polyamidoamine dendrimers; mechanism of complex formation and analysis of alterations induced in nuclease sensitivity and transcriptional activity of the complexed DNA", Biochimica et Biophysica Acta, 1997, pp. 180-190, vol. 1353.
Boder et al., "Directed evolution of antibody fragments with monovalent femtomolar antigen-binding affinity", Proceedings of the National Academy of Science, 2000, pp. 10701-10705, vol. 97.
Brenner et al., "GFAP Promoter Directs Astrocyte-Specific Expression in Transgenic Mice", The Journal of Neuroscience, 1994, pp. 1030-1037, vol. 14, No. 3.
Briggs et al., "A pH sensitive fluorescent cyanine dye for biological applications", Chemical Communication—Royal Society of Chemistry, 2000, pp. 2323-2324, vol. 23.
Carter, "Improving The Efficacy Of Antibody-Based Cancer Therapies", Nature Review/ Cancer, 2001, pp. 118-129, vol. 1.
Chao et al., "Isolating and engineering human antibodies using yeast surface display", Nature Protocols, 2006, pp. 755-768, vol. 1, No. 2.
Colby et al., "Potent inhibition of huntingtin aggregation and cytoxicity by a disulfide bond-free single-domain intracellular antibody", Proceedings of the National Academy of Sciences, 2004, pp. 17616-17621, vol. 101, No. 51.
Coloma et al, "Design and production of novel tetravalent bispecific antibodies", Nature Biotechnology, 1997, pp. 159-163, vol. 15, No. 2.
Cristiano et al., "Hepatic gene therapy: Adenovirus enhancement of receptor-mediated gene delivery and expression in primary hepatocytes", Proceedings of the National Academy of Science, 1993, pp. 2122-2126, vol. 90.
Cwirla et al., "Peptides on phage: A vast library of peptides for identifying ligands", Proceedings of the National Academy of Science, 1990, pp. 6378-6382, vol. 87.
Derossi et al., "Cell Internalization of the Third Helix of the Antennapedia Homeodomain Is Receptor-independent", The Journal of Biological Chemistry, 1996, pp. 18188-18193, vol. 271, No. 30.
Devlin et al., "Random Peptide Libraries: A Source of Specific Protein Binding Molecules", Science, 1990, pp. 404-406, vol. 249.
Dick et al., "Molecular Encapsulation: Cyclodextrin-Based Analogues of Heme-Containing Proteins", Journal of the American Chemical Society, 1992, pp. 2664-2669, vol. 114.
Ferguson et al., "Steric and Electronic Effects in Basic Dyes", JSDC, 1973, pp. 22-24.
Filler et al., "Fluorocarbanion chemistry. Tris(4-nitro-2,3,5,6-tetrafluorophenyl) methane and companions", Journal of Fluorine Chemistry, 2000, pp. 185-188, vol. 102.
Fisher et al., "Detection and Quantification of Beta2AR Internalization in Living Cells Using FAP-Based Biosensor Technology", Journal of Biomolecular Screening, 2010, pp. 703-709, vol. 15, No. 6.

(56) References Cited

OTHER PUBLICATIONS

Fitzpatrick et al., "Fluorogen Activating Peptide Based Energy Transfer Donors for FRET in Living Cells", Biophysical Journal, 2009, p. 294A, vol. 96, No. 31.
Fitzpatrick et al., "STED nanoscopy in living cells using Fluorogen Activating Proteins", Bioconjugate Chemistry 2009, pp. 1843-1847, vol. 20, No. 10.
Flotte et al., "Expression of the Cystic Fibrosis Transmembrane Conductance Regulator from a Novel Adeno-associated Virus Promoter", The Journal of Biological Chemistry. 1993, pp. 3781-3790, vol. 268, No. 5.
Gallo et al., "Fluorogen-activating scFv Biosensors Target Surface Markers on Live Cells Via Streptavidin or Single-Chain Avidin", Molecular Biotechnology, 2014, pp. 585-590, vol. 56.
Green et al., "Autonomous Functional Domains of Chemically Synthesized Human Immunodeficiency Virus Tat Trans-Activator Protein", Cell, 1988, pp. 1179-1188, vol. 55.
Grierson et al., "Genetic Transformation of Plants by Agrobacterium", Plant Molecular Biology, 2nd Edition, 1988, Ch. 7-9, Blackie, London.
Grover et al,, "Genetically Encoded pH Sensor for Tracking Surface Proteins through Endocytosis", Angewandte Chemie International Edition, 2012, pp. 4838-4842, vol. 51.
Guilbault, "Practical Fluorescence", 2nd Edition, 1990, pp. 88-92, Marcel Dekker, Inc., New York, New York.
Hanes et al., "Ribosome display efficiently selects and evolves high-affinity antibodies in vitro from immune libraries", Proceedings of the National Academy of Science, 1998, pp. 14130-14135, vol. 95.
Hanes et al., "In Vitro selection and evolution of functional proteins by using ribosome display", Proceedings of the National Academy of Science, 1997, pp. 4937-4942, vol. 91.
Hawker, et al., "Preparation of Polymers with Controlled Molecular Architecture. A New Convergent Approach to Dendritic Macromolecules", Journal of the American Chemical Society, 1990, pp. 7638-7647, vol. 112.
He et al., "Antibody-ribosome-mRNA (ARM) complexes as efficient selection particles for in vitro display and evolution of antibody combining sites", Nucleic Acids Research, 1997, pp. 5132-5134, vol. 25, No. 24.
Hermonat et al., "Use of adeno-associated virus as a mammalian DNA cloning vector: Transduction of neomycin resistance into mammalian tissue culture cells", Proceedings of the National Academy of Science, 1984, pp. 6466-6470, vol. 81.
Hochman et al., "An Active Antibody Fragment (Fv) Composed of the Variable Portions of Heavy and Light Chains", Biochemistry, 1973, pp. 1130-1135, vol. 12, No. 6.
Hoffman et al., "Ion Channel Assay Development using Invitrogen's FRET-Based Voltage Sensor Probes," BMG Labtech, 2005, Application Note 123.
Holt et al., "The use of recombinant antibodies in proteomics", Current Opinion in Biotechnology, 2000, pp. 445-449, vol. 11.
Hung et al., "Energy Transfer Primers with 5- or 6-Carboxyrhodamine-6G as Acceptor Chromophores", Analytical Biochemistry, 1996, pp. 165-170, vol. 238, Article No. 0270.
Hung et al., "Cyanine Dyes with High Absorption Cross Section as Donor Chromophores in Energy Transfer Primers", Analytical Biochemistry, 1996, pp. 15-27, vol. 243, Article No. 0477.
Ike et al., "Solid phase synthesis of polynucleotides, VIII Synthesis of mixed oligodeoxyribonucleotides by the phosphotriester solid phase method", Nucleic Acid Research, 1983, pp. 477-88, vol. 11, No. 2.
Iliades et al., "Triabodies: single chain Fv fragments without a linker form trivalent trimers", FEBS Letters 409, 1997, pp. 437-441.
Itakura et al., "Recombinant DNA—Chemical Synthesis and Application of Oligonucleotides of Mixed Sequence," Proceedings of the 3rd Cleveland Symposium on Macromolecules 1981, pp. 273-289, Elsevier Scientific Publishing Company, New York.

Itakura et al., "Expression in *Escherichia coli* of a Chemically Synthesized Gene for the Hormone Somatostatin", Science, 1977, pp. 1056-1063, vol. 198, No. 4321.
Itakura et al., "Synthesis and use of Synthetic Oligonucleotides", Annual Review of Biochemistry, 1984, pp. 323-356, vol. 53.
Jakobsson et al., "Lesion-dependent regulation of transgene expression in the rat brain using a human glial fibrillary acidic protein-lentiviral vector", European Journal of Neuroscience, pp. 761-765, vol. 19, No. 3.
Javed et al., "Diazo Preparation via Dehydrogenation of Hydrazones with "Activated" DMSO", Organic Letters, 2007, pp. 1789-1792, vol. 9, No. 9.
Jones et al., "Improvements in the Sensitivity of Time Resolved Fluorescence Energy Transfer Assays", Journal of Fluorescence, 2001, pp. 13-21, vol. 11, No. 1.
Jones et. al., "Improvements in the Sensitivity of Time Resolved Fluorescence Energy Transfer Assays", 1999, 6th International conference on methods and applications of fluorescence, Paris, Frankreich. http://www.gelifesciences.com/aptrix/upp00919.nsf/Content/86561D86921D3BF7C1257628001CE279/$file/improve.pdf.
Josefsen et al., "Photodynamic therapy: novel third-generation photosensitizers one step closer?", British Journal of Pharmacology, 2008, pp. 1-3, vol. 154.
Klajnert et al., "Dendrimers: properties and applications", Acta Biochimica Polonica, 2001, pp. 199-208, vol. 48, No. 1.
Kraus et al., "Fluorinated Analogs of Malachite Green: Synthesis and Toxicity", Molecules, 2008, pp. 986-994, vol. 13.
Kuby, "Immunology", Third Edition, 1997, pp. 131-139, W.H. Freeman & Co., New York.
Kugler et al., "Human Synapsin 1 Gene Promoter Confers Highly Neuron-Specific Long-Term Transgene Expression from an Adenoviral Vector in the Adult Rat Brain Depending on the Transduced Area", Gene Therapy, 2003, pp. 337-347, vol. 10.
Lagnoux et al., "Synthesis and Esterolytic Activity of Catalytic Peptide Dendrimers", Chemistry—A European Journal, 2004, pp. 1215-1226, vol. 10.
Lois et al., "Germline Transmission and Tissue-Specific Expression of Transgenes Delivered by Lentiviral Vectors", Science, 2002, pp. 868-872, vol. 295.
Lovell et al., "Activatable Photosensitizers for Imaging and Therapy", Chemical Reviews, 2010, pp. 2839-2857, vol. 110.
Martin et al., "Mammalian cell-based optimization of the biarsenical-binding tetracysteine motif for improved fluorescence and affinity", Nature Biotechnology, 2005, pp. 1-7.
Miller, "Progress Toward Human Gene Therapy", Blood, 1990, pp. 271-278, vol. 76, No. 2.
Mitsunaga et al., "Cancer cell—selective in vivo near infrared photoimmunotherapy targeting specific membrane molecules", Nature Medicine, 2011, pp. 1685-1691, vol. 17, No. 12.
Mizuno et al., "Basic research for interferon gene therapy against malignant glioma", No Shinkei Geka, 1992, pp. 547-551, vol. 20, No. 5.
Mizuno et al., "Growth inhibition of glioma cells by liposome-mediated cell transfection with tumor necrosis factor-alpha gene—its enhancement by prior gamma-interferon treatment", Neurologia Medico-Chirugrica, 1992, pp. 873-876, vol. 32, No. 12.
Mujumdar et al., "Cyanine Dye Labeling Reagents: Sulfoindocyanine Succinimidyl Esters", Bioconjugate Chemistry, 1993, pp. 105-111, vol. 4, No. 2.
Mulligan, "The Basic Science of Gene Therapy", Science, 1993, pp. 926-932, vol. 260.
Narang, "Tetrahedron Report No. 140—DNA Synthesis", Tetrahedron, 1983, pp. 3-22, vol. 39, No. 1.
Ozhalici-Unal et al., "A Rainbow of Fluoromodules: A Promiscuous scFv Protein Binds to and Activates a Diverse Set of Fluourenic Cyanine Dyes", Journal of the American Chemical Society, 2008, pp. 12620-12621, vol. 130, No. 38.
Pack et al., "Tetravalent Miniantibodies with High Avidity Assembling in *Escherichia coli*", Journal of Molecular Biology, 1995, pp. 28-34, vol. 246.

(56) References Cited

OTHER PUBLICATIONS

Paladino et al., "Different GPI-attachment signals affect the oligomerization of GPI-anchored proteins and their apical sorting", Journal of Cell Science, 2008, pp. 4001-4007, vol. 121, No. 24.
Patterson et al., "Use of the Green Fluorescent Protein and Its Mutants in Quantitative Fluorescence Microscopy", Biophysical Journal, 1997, pp. 2782-2790, vol. 73.
Perron et al., "Second and third generation voltage-sensitive fluorescent proteins for monitoring membrane potential", Frontiers in Molecular Neuroscience, 2009, pp. 1-8, vol. 2, Article 5.
Prates et al., "Bactericidal effect of malachite green and red laser on Actinobacillus actinomycetemcomitans", Journal of Photochemistry and Photobiology B: Biology, 2007, pp. 70-76, vol. 86.
Promega In Vitro Resource, "Chapter Six: Ribosome Display", 2005, pp. 29-33, Promega Corporation, Madison, WI.
Rao et al., "Integrating cell-level kinetic modeling into the design of engineered protein therapeutics", Nature Biotechnology, 2005, pp. 191-194, vol. 23, No. 2.
Roberts et al., "Directed evolution of a protein: Selection of potent neutrophil elastase inhibitors displayed on M13 fusion phage", Proceedings of the National Academy of Science, 1992, pp. 2429-2433, vol. 89.
Rogers et al., "Gene Transfer in Plants: Production of Transformed Plants Using Ti Plasmid Vectors", Methods for Plant Molecular Biology, 1988, Section VIII, pp. 423-463, Academic Press Inc., New York.
Saunders et al., "A Bifunctional Converter: Fluorescein Quenching scFv/Fluorogen Activating Protein for Photostability and Improved Signal to Noise in Fluorescence Experiments", Bioconjugate Chemistry, 2014, pp. 1556-1564, vol. 25.
Saurabh et al., "Multiplexed Modular Genetic Targeting of Quantum Dots", ACS Nano, 2014, pp. 11138-11146, vol. 8, No. 11.
Schoch et al., "Neuron-specific gene expression of Synapsin I Major Role of a Negative Regulatory Mechanism", Journal of Biological Chemistry, 1996, pp. 3317-3323, vol. 271, No. 6.
Scott et al., "Searching for Peptide Ligands with an Epitope Library", Science, 1990, pp. 386-390, vol. 249.
Shaner et al., "Improved monomeric red, orange and yellow fluorescent proteins derived from *Discosoma* sp. red fluorescent protein", Nature Biotechnology, 2004, pp. 1567-1572, vol. 22, No. 12.
Shank et al., "Enhanced Photostability of Genetically Encodable Fluoromodules Based on Fluorogenic Cyanine Dyes and a Promiscuous Protein Partner", Journal of the American Chemical Society, 2009, pp. 12960-12969, vol. 131.
Sharon et al., "Preparation of Fv Fragment from the Mouse Myeloma XRPC-25 Immunoglobulin Possessing Anti-Dinitrophenyl Activity", Biochemistry, 1976, pp. 1591-1594, vol. 15, No. 7.
Spring et al., "Selective treatment and monitoring of disseminated cancer micrometastases in vivo using dual-function, activatable immunoconjugates", Proceedings of the National Academy of Science, 2014, pp. E933-E942.
Swers, et al., "Shuffled antibody libraries created by in vivo homologous recombination and yeast surface display", Nucleic Acids Research, 2004, pp. 1-8, vol. 32, No. 3.
Szent-Gyorgy et al., "Fluorogen-activating single-chain antibodies for imaging cell surface proteins", Nature Biotechnology, 2008, pp. 235-240, vol. 26.
Szidonya et al., "Dimerization and oligomerization of G-protein-coupled receptors: debated structures with established and emerging functions", Journal of Endocrinology, 2008, pp. 435-453, vol. 196.
Tratschin et al., "Adeno-Associated Virus Vector for High-Frequency Integration, Expression, and Rescue of Genes in Mammalian Cells", Molecular and Cellular Biology, 1985, pp. 3251-3260, vol. 5, No. 11.
Trikha et al., "Monoclonal antibodies as therapeutics in oncology", Curr. Opin. Biotechnol., 2002, pp. 609-614, vol. 13.
Vandier et al., "Inhibition of glioma cells in vitro and in vivo using a recombinant adenoviral vector containing an astrocyte-specific promoter", Cancer Gene Therapy, 2000, pp. 1120-1126, vol. 7, No. 8.
Viac et al., "An Immunoelectron Microscopic Localization of Wart Associated Antigens Present in Human Papilloma Virus (HPV) Infected Cells", Journal of Investigative Dermatology, 1978, pp. 263-266, vol. 70, No. 5.
Wagner et al., "Influenza virus hemagglutinin HA-2 N-terminal fusogenic peptides augment gene transfer by transferrin-polylysine-DNA complexes: Toward a synthetic virus-like gene-transfer vehicle", Proceedings of the National Academy of Science, 1992, pp. 7934-7938, vol. 89.
Ward et al., "Binding activities of a repertoire of single immunoglobulin variable domains secreted from *Escherichia coli*", Nature, 1989, pp. 544-546, vol. 341.
Weinstock et al., "Synthesis and Evaluation of Non-Catechol D-1 and D-2 Dopamine Receptor Agonists: Benzimidazol-2-one, Benzoxazol-2-one, and the Highly Potent Benzothiazol-2-one 7-Ethylamines", Journal of Medicinal Chemistry, 1987, pp. 11, vol. 30.
Weissbach et al., "Methods for Plant Molecular Biology", 1988, Section VIII, pp. 421-463, Academic Press, New York.
White et al., "Comparison of the glycosyl-phosphatidylinositol cleavage/attachment site between mammalian cells and parasitic protozoa", Journal of Cell Science, 2000, pp. 721-727, vol. 113.
"Yeast Display scFv Antibody Library User's Manual", Pacific Northwest National Laboratory, Richland, WA 99352, Revision Date: MF031112
Yoo et al., "Antibody-ligand interactions studied by fluorescence enhancement methods I. Properties of the ligands 4-anilinonaphthalene-1-sulfonate and 6-anilinonaphthalene-2-sulfonate", Immunochemistry, 1970, pp. 627-636, vol. 7, No. 7.

\* cited by examiner

L5-MG
QAVVTQEPSVTVSPGGTVILTCGSSTGAVTSGHYANWFQQKPGQAPRALIFETDKKYPWTPGRFSGSLLG
VKAALTISDAQPEDEAEYYCLLSDVDGYLFGGGTQLTVLS

L5-MG E52D
QAVVTQEPSVTVSPGGTVILTCGSSTGAVTSGHYANWFQQKPGQAPRALIF<u>D</u>TDKKYPWTPGRFSGSLLG
VKAALTISDAQPEDEAEYYCLLSDVDGYLFGGGTQLTVLS

L5-MG L91S
QAVVTQEPSVTVSPGGTVILTCGSSTGAVTSGHYANWFQQKPGQAPRALIFETDKKYPWTPGRFSGSLLG
VKAALTISDAQPEDEAEYYC<u>S</u>LSDVDGYLFGGGTQLTVLS

L5-MG E52D L91S
QAVVTQEPSVTVSPGGTVILTCGSGTGAVTSGHYANWFQQKPGQAPRALIF<u>D</u>TDKKYPWTPGRFSGSLLG
VKAALTISDAQPEDEAEYYC<u>S</u>LSDVDGYLFGGGTQLTVLS

*Fig. 2A*

HL4-MG core 251aa
QVQLVESEGGLVQPGGSLRLSCAASGFTFSSYEMNWVRQAPGKGLEWVSRIDGDGSSTNYADSVKGRFTI
SRDNAKSTLYLQMNSLRAEDTAVYYCTRARYFGSVSPYGMDVWGQGTTVTVSSGILGSGGGGSGGGGSGG
GGSDIRVTQSPSSVSASVGDRVTISCRASQGIATWLGWYQQKPGKPPQLLIYSASTLQTGVPSRFSGSGS
GTDFTLTISSLQPEDVATYYCQEGSTFPLTFGGGTKVDIKS H6-MG in PNL6 core 130aa
QVQLQESGPGLVKPSETLSLTCTVSGASISSSHYYWGWIRQPPGKGPEWIGSMYYSGRTYYNPALKSRVT
ISPDKSKNQFFLKLTSVTAADTAVYYCAREGPTHYYDNSGPIPSDEYFQHWGQGTLVTVS L9-MG secreted form (MG67) (6aa - 114aa) 109aa
SYELTQPPSVSVSPGQTARITCSGDALPKQYTYWYQQKAGQAPVLVIYKDTERPSGIPERFSGTSSGTTV
TLTISGVQAEDEADYYCQSADSSGSYVFFGGGTKVTVLS

*Fig. 2B*

L5-MG E52D pPNL6 fusion protein 250aa
MQLLRCFSIFSVIASVLAQELTTICEQIPSPTLESTPYSLSTTTILANGKAMQGVFEYYKSVTFVSNCGS
HPSTTSKGSPINTQYVFKDNSSTIEGRYPYDVPDYALQASGGGGSGGGGSGGGGSASQAVVTQEPSVTVS
PGGTVILTCGSSTGAVTSGHYANWFQQKPGQAPRALIFDTDKKYPWTPGRFSGSLLGVKAALTISDAQPE
DEAEYYCLLSDVDGYLFGGGTQLTVLSGILEQKLISEEDL

*Fig. 3A*

L5-MG E52D fusion protein expressed in pPNL6

*Fig 3D*

Her1-dL5AffiFAP:

GPSKLAEAKYAKEMWAAWEEIRNLPNLTGWQMTAFIAKLVDDPSQSSELLSEAKKLND
SQAPKASGSTSGTQAVVTQEPSVTVSPGGTVILTCGSGTGAVTSGHYANWFQQKPG
QAPRALIFDTDKKYSWTPGRFSGSLLGAKAALTISDAQPEDEAEYYCSLSDVDGYLFG
GGTQLTVLSGGGGSGGGGSGGGGSGGGGSQAVVTQEPSVTVSPGGTVILTCGSGT
GAVTSGHYANWFQQKPGQAPRALIFDTDKKYSWTPGRFSGSLLGAKAALTISDAQPE
DEAEYYCSLSDVDGYLFGGGTQLTVLSLE dL5-HER1 AffiFAP:

GPSKLQAVVTQEPSVTVSPGGTVILTCGSGTGAVTSGHYANWFQQKPGQAPRALIFD
TDKKYSWTPGRFSGSLLGAKAALTISDAQPEDEAEYYCSLSDVDGYLFGGGTQLTVLS
GGGGSGGGGSGGGGSGGGGSQAVVTQEPSVTVSPGGTVILTCGSGTGAVTSGHYA
NWFQQKPGQAPRALIFDTDKKYSWTPGRFSGSLLGAKAALTISDAQPEDEAEYYCSLS
DVDGYLFGGGTQLTVLSAEAKYAKEMWAAWEEIRNLPNLTGWQMTAFIAKLVDDPSQ
SSELLSEAKKLNDSQAPKL

Her1-dL5-Her1 AffiFAP:

GPSKLAEAKYAKEMWAAWEEIRNLPNLTGWQMTAFIAKLVDDPSQSSELLSEAKKLND
SQAPKGSQAVVTQEPSVTVSPGGTVILTCGSGTGAVTSGHYANWFQQKPGQAPRALI
FDTDKKYSWTPGRFSGSLLGAKAALTISDAQPEDEAEYYCSLSDVDGYLFGGGTQLTV
LSGGGGSGGGGSGGGGSGGGGSQAVVTQEPSVTVSPGGTVILTCGSGTGAVTSGH
YANWFQQKPGQAPRALIFDTDKKYSWTPGRFSGSLLGAKAALTISDAQPEDEAEYYC
SLSDVDGYLFGGGTQLTVLSGTAEAKYAKEMWAAWEEIRNLPNLTGWQMTAFIAKLV
DDPSQSSELLSEAKKLNDSQAPKLE

Fig. 16A dL5-Her2 AffiFAP:

GPSKLQAVVTQEPSVTVSPGGTVILTCGSGTGAVTSHYANWFQQKPGQAPRALIFDT
DKKYSWTPGRFSGSLLGAKAALTISDAQPEDEAEYYCSLSDVDGYLFGGGTQLTVLSG
GGGSGGGGSGGGGSGGGGSQAVVTQEPSVTVSPGGTVILTCGSGTGAVTSGHYAN
WFQQKPGQAPRALIFDTDKKYSWTPGRFSGSLLGAKAALTISDAQPEDEAEYYCSLSD
VDGYLFGGGTQLTVLSASGSTSGTVENKFNKEMRNAYWEIALLPNLNNQQKRAFIRSL
YDDPSQSANLLAEAKKLNDAQAPKLE

Her2-dL5 AffiFAP:

GPSKLVENKFNKEMRNAYWEIALLPNLNNQQKRAFIRSLYDDPSQSANLLAEAKKLND
AQAPKGSTSGTQAVVTQEPSVTVSPGGTVILTCGSGTGAVTSGHYANWFQQKPGQA
PRALIFDTDKKYSWTPGRFSGSLLGAKAALTISDAQPEDEAEYYCSLSDVDGYLFGGG
TQLTVLSGGGGSGGGGSGGGGSGGGGSQAVVTQEPSVTVSPGGTVILTCGSGTGAV
TSGHYANWFQQKPGQAPRALIFDTDKKYSWTPGRFSGSLLGAKAALTISDAQPEDEA
EYYCSLSDVDGYLFGGGTQLTVLSLE

Her2-dL5-Her2 AffiFAP:

GPSKLVENKFNKEMRNAYWEIALLPNLNNQQKRAFIRSLYDDPSQSANLLAEAKKLND
AQAPKGSTSGTQAVVTQEPSVTVSPGGTVILTCGSGTGAVTSGHYANWFQQKPGQA
PRALIFDTDKKYSWTPGRFSGSLLGAKAALTISDAQPEDEAEYYCSLSDVDGYLFGGG
TQLTVLSGGGGSGGGGSGGGGSGGGGSQAVVTQEPSVTVSPGGTVILTCGSGTGAV
TSGHYANWFQQKPGQAPRALIFDTDKKYSWTPGRFSGSLLGAKAALTISDAQPEDEA
EYYCSLSDVDGYLFGGGTQLTVLSGTVENKFNKEMRNAYWEIALLPNLNNQQKRAFIR
SLYDDPSQSANLLAEAKKLNDAQAPKLE

Fig. 16B

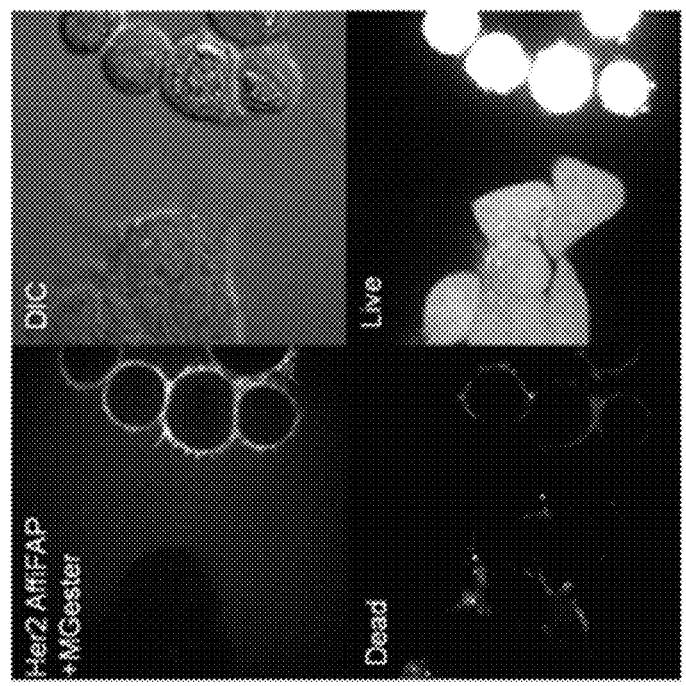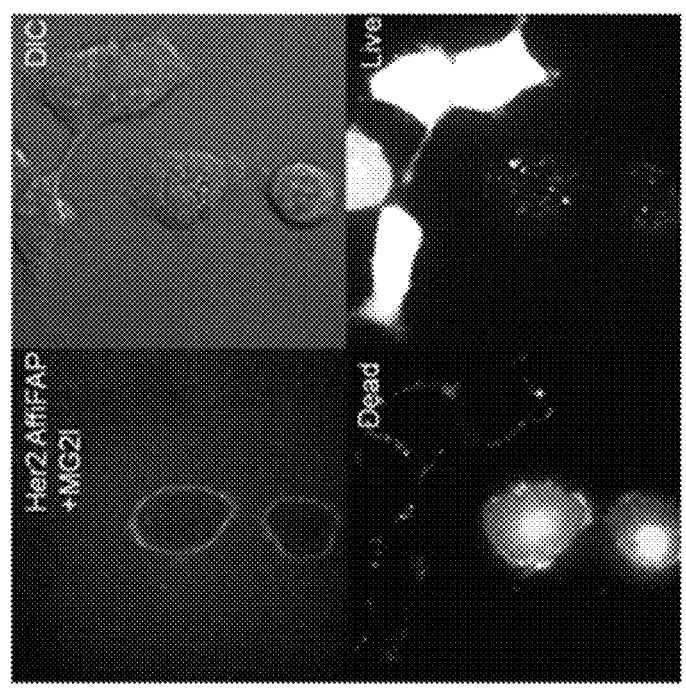
Fig. 18

```
                        SEQUENCE LISTING

<160> NUMBER OF SEQ ID NOS: 18

<210> SEQ ID NO 1
<211> LENGTH: 110
<212> TYPE: PRT
<213> ORGANISM: Artificial Sequence
<220> FEATURE:
<223> OTHER INFORMATION: fluorogen activating peptide L5-MG

<400> SEQUENCE: 1

Gln Ala Val Val Thr Gln Glu Pro Ser Val Thr Val Ser Pro Gly Gly
1               5                   10                  15

Thr Val Ile Leu Thr Cys Gly Ser Ser Thr Gly Ala Val Thr Ser Gly
            20                  25                  30

His Tyr Ala Asn Trp Phe Gln Gln Lys Pro Gly Gln Ala Pro Arg Ala
        35                  40                  45

Leu Ile Phe Glu Thr Asp Lys Lys Tyr Pro Trp Thr Pro Gly Arg Phe
    50                  55                  60

Ser Gly Ser Leu Leu Gly Val Lys Ala Ala Leu Thr Ile Ser Asp Ala
65                  70                  75                  80

Gln Pro Glu Asp Glu Ala Glu Tyr Tyr Cys Leu Leu Ser Asp Val Asp
                85                  90                  95

Gly Tyr Leu Phe Gly Gly Gly Thr Gln Leu Thr Val Leu Ser
            100                 105                 110

<210> SEQ ID NO 2
<211> LENGTH: 110
<212> TYPE: PRT
<213> ORGANISM: Artificial Sequence
<220> FEATURE:
<223> OTHER INFORMATION: fluorogen activating peptide L5-MG E52D

<400> SEQUENCE: 2

Gln Ala Val Val Thr Gln Glu Pro Ser Val Thr Val Ser Pro Gly Gly
1               5                   10                  15

Thr Val Ile Leu Thr Cys Gly Ser Ser Thr Gly Ala Val Thr Ser Gly
            20                  25                  30
```

His Tyr Ala Asn Trp Phe Gln Gln Lys Pro Gly Gln Ala Pro Arg Ala
            35                  40                  45

Leu Ile Phe Asp Thr Asp Lys Lys Tyr Pro Trp Thr Pro Gly Arg Phe
 50                  55                  60

Ser Gly Ser Leu Leu Gly Val Lys Ala Ala Leu Thr Ile Ser Asp Ala
 65                  70                  75                  80

Gln Pro Glu Asp Glu Ala Glu Tyr Tyr Cys Leu Leu Ser Asp Val Asp
                 85                  90                  95

Gly Tyr Leu Phe Gly Gly Gly Thr Gln Leu Thr Val Leu Ser
            100                 105                 110

<210> SEQ ID NO 3
<211> LENGTH: 110
<212> TYPE: PRT
<213> ORGANISM: Artificial Sequence
<220> FEATURE:
<223> OTHER INFORMATION: fluorogen activating peptide L5-MG L91S

<400> SEQUENCE: 3

Gln Ala Val Val Thr Gln Glu Pro Ser Val Thr Val Ser Pro Gly Gly
 1               5                  10                  15

Thr Val Ile Leu Thr Cys Gly Ser Ser Thr Gly Ala Val Thr Ser Gly
             20                  25                  30

His Tyr Ala Asn Trp Phe Gln Gln Lys Pro Gly Gln Ala Pro Arg Ala
            35                  40                  45

Leu Ile Phe Glu Thr Asp Lys Lys Tyr Pro Trp Thr Pro Gly Arg Phe
 50                  55                  60

Ser Gly Ser Leu Leu Gly Val Lys Ala Ala Leu Thr Ile Ser Asp Ala
 65                  70                  75                  80

Gln Pro Glu Asp Glu Ala Glu Tyr Tyr Cys Ser Leu Ser Asp Val Asp
                 85                  90                  95

Gly Tyr Leu Phe Gly Gly Gly Thr Gln Leu Thr Val Leu Ser
            100                 105                 110

<210> SEQ ID NO 4
<211> LENGTH: 110
<212> TYPE: PRT
<213> ORGANISM: Artificial Sequence
<220> FEATURE:
<223> OTHER INFORMATION: fluorogen activating peptide L5-MG E52D L91S

<400> SEQUENCE: 4

Gln Ala Val Val Thr Gln Glu Pro Ser Val Thr Val Ser Pro Gly Gly
 1               5                  10                  15

Thr Val Ile Leu Thr Cys Gly Ser Gly Thr Gly Ala Val Thr Ser Gly
             20                  25                  30

His Tyr Ala Asn Trp Phe Gln Gln Lys Pro Gly Gln Ala Pro Arg Ala
            35                  40                  45

Leu Ile Phe Asp Thr Asp Lys Lys Tyr Pro Trp Thr Pro Gly Arg Phe
 50                  55                  60

Ser Gly Ser Leu Leu Gly Val Lys Ala Ala Leu Thr Ile Ser Asp Ala
 65                  70                  75                  80

Gln Pro Glu Asp Glu Ala Glu Tyr Tyr Cys Ser Leu Ser Asp Val Asp
                 85                  90                  95

Gly Tyr Leu Phe Gly Gly Gly Thr Gln Leu Thr Val Leu Ser
            100                 105                 110

<210> SEQ ID NO 5

<211> LENGTH: 251
<212> TYPE: PRT
<213> ORGANISM: Artificial Sequence
<220> FEATURE:
<223> OTHER INFORMATION: fluorogen activating peptide HL4-MG core 251aa

<400> SEQUENCE: 5

```
Gln Val Gln Leu Val Glu Ser Glu Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Arg Ile Asp Gly Asp Gly Ser Ser Thr Asn Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Tyr Cys
                85                  90                  95

Thr Arg Ala Arg Tyr Phe Gly Ser Val Ser Pro Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Ser Gly Gly Gly Ser Asp
    130                 135                 140

Ile Arg Val Thr Gln Ser Pro Ser Ser Val Ser Ala Ser Val Gly Asp
145                 150                 155                 160

Arg Val Thr Ile Ser Cys Arg Ala Ser Gln Gly Ile Ala Thr Trp Leu
                165                 170                 175

Gly Trp Tyr Gln Gln Lys Pro Gly Lys Pro Pro Gln Leu Leu Ile Tyr
            180                 185                 190

Ser Ala Ser Thr Leu Gln Thr Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Val Ala Thr Tyr Tyr Cys Gln Glu Gly Ser Thr Phe Pro Leu Thr
225                 230                 235                 240

Phe Gly Gly Gly Thr Lys Val Asp Ile Lys Ser
                245                 250
```

<210> SEQ ID NO 6
<211> LENGTH: 130
<212> TYPE: PRT
<213> ORGANISM: Artificial Sequence
<220> FEATURE:
<223> OTHER INFORMATION: fluorogen activating peptide H6-MG in PNL6 core
    130aa

<400> SEQUENCE: 6

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

His Tyr Tyr Trp Gly Trp Ile Arg Gln Pro Pro Gly Lys Gly Pro Glu
        35                  40                  45

Trp Ile Gly Ser Met Tyr Tyr Ser Gly Arg Thr Tyr Tyr Asn Pro Ala
    50                  55                  60
```

```
Leu Lys Ser Arg Val Thr Ile Ser Pro Asp Lys Ser Lys Asn Gln Phe
 65                  70                  75                  80

Phe Leu Lys Leu Thr Ser Val Thr Ala Ala Asp Thr Ala Val Tyr Tyr
                 85                  90                  95

Cys Ala Arg Glu Gly Pro Thr His Tyr Tyr Asp Asn Ser Gly Pro Ile
            100                 105                 110

Pro Ser Asp Glu Tyr Phe Gln His Trp Gly Gln Gly Thr Leu Val Thr
        115                 120                 125

Val Ser
    130
```

```
<210> SEQ ID NO 7
<211> LENGTH: 109
<212> TYPE: PRT
<213> ORGANISM: Artificial Sequence
<220> FEATURE:
<223> OTHER INFORMATION: fluorogen activating peptide L9-MG secreted
      form (MG67) (6aa-114aa) 109aa

<400> SEQUENCE: 7

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Thr
                 20                  25                  30

Tyr Trp Tyr Gln Gln Lys Ala Gly Gln Ala Pro Val Leu Val Ile Tyr
             35                  40                  45

Lys Asp Thr Glu Arg Pro Ser Gly Ile Pro Glu Arg Phe Ser Gly Thr
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Ser Tyr
                 85                  90                  95

Val Phe Phe Gly Gly Gly Thr Lys Val Thr Val Leu Ser
            100                 105
```

```
<210> SEQ ID NO 8
<211> LENGTH: 250
<212> TYPE: PRT
<213> ORGANISM: Artificial Sequence
<220> FEATURE:
<223> OTHER INFORMATION: fluorogen activating peptide - fusion protein
      L5-MG ED2D pPNL6 fusion protein 250aa

<400> SEQUENCE: 8

Met Gln Leu Leu Arg Cys Phe Ser Ile Phe Ser Val Ile Ala Ser Val
 1               5                  10                  15

Leu Ala Gln Glu Leu Thr Thr Ile Cys Glu Gln Ile Pro Ser Pro Thr
                 20                  25                  30

Leu Glu Ser Thr Pro Tyr Ser Leu Ser Thr Thr Thr Ile Leu Ala Asn
             35                  40                  45

Gly Lys Ala Met Gln Gly Val Phe Glu Tyr Tyr Lys Ser Val Thr Phe
 50                  55                  60

Val Ser Asn Cys Gly Ser His Pro Ser Thr Thr Ser Lys Gly Ser Pro
 65                  70                  75                  80

Ile Asn Thr Gln Tyr Val Phe Lys Asp Asn Ser Ser Thr Ile Glu Gly
                 85                  90                  95

Arg Tyr Pro Tyr Asp Val Pro Asp Tyr Ala Leu Gln Ala Ser Gly Gly
            100                 105                 110
```

```
Gly Gly Ser Gly Gly Gly Gly Ser Gly Gly Gly Ser Ala Ser Gln
            115                 120                 125

Ala Val Val Thr Gln Glu Pro Ser Val Thr Val Ser Pro Gly Gly Thr
        130                 135                 140

Val Ile Leu Thr Cys Gly Ser Ser Thr Gly Ala Val Thr Ser Gly His
145                 150                 155                 160

Tyr Ala Asn Trp Phe Gln Gln Lys Pro Gly Gln Ala Pro Arg Ala Leu
                165                 170                 175

Ile Phe Asp Thr Asp Lys Lys Tyr Pro Trp Thr Pro Gly Arg Phe Ser
            180                 185                 190

Gly Ser Leu Leu Gly Val Lys Ala Ala Leu Thr Ile Ser Asp Ala Gln
        195                 200                 205

Pro Glu Asp Glu Ala Glu Tyr Tyr Cys Leu Leu Ser Asp Val Asp Gly
    210                 215                 220

Tyr Leu Phe Gly Gly Gly Thr Gln Leu Thr Val Leu Ser Gly Ile Leu
225                 230                 235                 240

Glu Gln Lys Leu Ile Ser Glu Glu Asp Leu
                245                 250

<210> SEQ ID NO 9
<211> LENGTH: 813
<212> TYPE: DNA
<213> ORGANISM: Artificial Sequence
<220> FEATURE:
<223> OTHER INFORMATION: fluorogen activating peptide-Fusion protein
      pPNL6 L5-MG E52D nucleotide sequence

<400> SEQUENCE: 9
aaaaaacccc ggatcgaatt ctacttcata catttttcaat taagatgcag ttacttcgct      60 gttttttcaat attttctgtt attgcttcag ttttagcaca ggaactgaca actatatgcg     120
agcaaatccc ctcaccaact ttagaatcga cgccgtactc tttgtcaacg actactattt     180
tggccaacgg gaaggcaatg caaggagttt tgaatatta caaatcagta acgtttgtca     240
gtaattgcgg ttctcacccc tcaacaacta gcaaaggcag ccccataaac acacagtatg     300
tttttaagga caatagctcg acgattgaag gtagataccc atacgacgtt ccagactacg     360
ctctgcaggc tagtggtggt ggtggttctg gtggtggtgg ttctggtggt ggtggttctg     420
ctagccaggc tgtggtgact caggagccgt cagtgactgt gtcccaggga ggacagtca     480 ttctcacttg tggctccagc actggagctg tcaccagtgg tcattatgcc aactggttcc     540
agcagaaacc tggccaagcc cccagggcac ttatatttga caccgacaag aaatatccct     600 ggaccccctgg ccgattctca ggctccctcc ttggggtcaa ggctgccctg accatctcgg     660
atgcgcagcc tgaagatgag gctgagtatt actgtttgct ctccgacgtt gacggttatc     720
tgttcggagg aggcacccag ctgaccgtcc tctccggaat tctagaacaa aagcttattt     780
ctgaagaaga cttgtaatag ctcggcggcc gca                                    813

<210> SEQ ID NO 10
<211> LENGTH: 313
<212> TYPE: PRT
<213> ORGANISM: Artificial Sequence
<220> FEATURE:
<223> OTHER INFORMATION: Affibody-fluorogen activating peptide fusion
      protein Her1-dL5AffiFAP

<400> SEQUENCE: 10

Gly Pro Ser Lys Leu Ala Glu Ala Lys Tyr Ala Lys Glu Met Trp Ala
1               5                   10                  15
```

-continued

Ala Trp Glu Glu Ile Arg Asn Leu Pro Asn Leu Thr Gly Trp Gln Met
            20                  25                  30

Thr Ala Phe Ile Ala Lys Leu Val Asp Asp Pro Ser Gln Ser Ser Glu
        35                  40                  45

Leu Leu Ser Glu Ala Lys Lys Leu Asn Asp Ser Gln Ala Pro Lys Ala
    50                  55                  60

Ser Gly Ser Thr Ser Gly Thr Gln Ala Val Val Thr Gln Glu Pro Ser
65                  70                  75                  80

Val Thr Val Ser Pro Gly Gly Thr Val Ile Leu Thr Cys Gly Ser Gly
                85                  90                  95

Thr Gly Ala Val Thr Ser Gly His Tyr Ala Asn Trp Phe Gln Gln Lys
            100                 105                 110

Pro Gly Gln Ala Pro Arg Ala Leu Ile Phe Asp Thr Asp Lys Lys Tyr
        115                 120                 125

Ser Trp Thr Pro Gly Arg Phe Ser Gly Ser Leu Leu Gly Ala Lys Ala
130                 135                 140

Ala Leu Thr Ile Ser Asp Ala Gln Pro Glu Asp Glu Ala Glu Tyr Tyr
145                 150                 155                 160

Cys Ser Leu Ser Asp Val Asp Gly Tyr Leu Phe Gly Gly Gly Thr Gln
                165                 170                 175

Leu Thr Val Leu Ser Gly Gly Gly Gly Ser Gly Gly Gly Gly Ser Gly
            180                 185                 190

Gly Gly Ser Gly Gly Gly Gly Ser Gln Ala Val Val Thr Gln Glu
        195                 200                 205

Pro Ser Val Thr Val Ser Pro Gly Gly Thr Val Ile Leu Thr Cys Gly
    210                 215                 220

Ser Gly Thr Gly Ala Val Thr Ser Gly His Tyr Ala Asn Trp Phe Gln
225                 230                 235                 240

Gln Lys Pro Gly Gln Ala Pro Arg Ala Leu Ile Phe Asp Thr Asp Lys
                245                 250                 255

Lys Tyr Ser Trp Thr Pro Gly Arg Phe Ser Gly Ser Leu Leu Gly Ala
            260                 265                 270

Lys Ala Ala Leu Thr Ile Ser Asp Ala Gln Pro Glu Asp Glu Ala Glu
        275                 280                 285

Tyr Tyr Cys Ser Leu Ser Asp Val Asp Gly Tyr Leu Phe Gly Gly Gly
    290                 295                 300

Thr Gln Leu Thr Val Leu Ser Leu Glu
305                 310

<210> SEQ ID NO 11
<211> LENGTH: 304
<212> TYPE: PRT
<213> ORGANISM: Artificial Sequence
<220> FEATURE:
<223> OTHER INFORMATION: Affibody-fluorogen activating peptide fusion
      protein dL5-HER1 AffiFAP

<400> SEQUENCE: 11

Gly Pro Ser Lys Leu Gln Ala Val Val Thr Gln Glu Pro Ser Val Thr
1               5                   10                  15

Val Ser Pro Gly Gly Thr Val Ile Leu Thr Cys Gly Ser Gly Thr Gly
            20                  25                  30

Ala Val Thr Ser Gly His Tyr Ala Asn Trp Phe Gln Gln Lys Pro Gly
        35                  40                  45

Gln Ala Pro Arg Ala Leu Ile Phe Asp Thr Asp Lys Lys Tyr Ser Trp

```
                50                  55                  60
Thr Pro Gly Arg Phe Ser Gly Ser Leu Leu Gly Ala Lys Ala Ala Leu
65                  70                  75                  80

Thr Ile Ser Asp Ala Gln Pro Glu Asp Glu Ala Glu Tyr Tyr Cys Ser
                85                  90                  95

Leu Ser Asp Val Asp Gly Tyr Leu Phe Gly Gly Gly Thr Gln Leu Thr
            100                 105                 110

Val Leu Ser Gly Gly Gly Ser Gly Gly Gly Ser Gly Gly Gly
        115                 120                 125

Gly Ser Gly Gly Gly Ser Gln Ala Val Val Thr Gln Glu Pro Ser
    130                 135                 140

Val Thr Val Ser Pro Gly Gly Thr Val Ile Leu Thr Cys Gly Ser Gly
145                 150                 155                 160

Thr Gly Ala Val Thr Ser Gly His Tyr Ala Asn Trp Phe Gln Gln Lys
                165                 170                 175

Pro Gly Gln Ala Pro Arg Ala Leu Ile Phe Asp Thr Asp Lys Lys Tyr
            180                 185                 190

Ser Trp Thr Pro Gly Arg Phe Ser Gly Ser Leu Leu Gly Ala Lys Ala
        195                 200                 205

Ala Leu Thr Ile Ser Asp Ala Gln Pro Glu Asp Glu Ala Glu Tyr Tyr
210                 215                 220

Cys Ser Leu Ser Asp Val Asp Gly Tyr Leu Phe Gly Gly Gly Thr Gln
225                 230                 235                 240

Leu Thr Val Leu Ser Ala Glu Ala Lys Tyr Ala Lys Glu Met Trp Ala
                245                 250                 255

Ala Trp Glu Glu Ile Arg Asn Leu Pro Asn Leu Thr Gly Trp Gln Met
            260                 265                 270

Thr Ala Phe Ile Ala Lys Leu Val Asp Asp Pro Ser Gln Ser Ser Glu
        275                 280                 285

Leu Leu Ser Glu Ala Lys Lys Leu Asn Asp Ser Gln Ala Pro Lys Leu
    290                 295                 300

<210> SEQ ID NO 12
<211> LENGTH: 367
<212> TYPE: PRT
<213> ORGANISM: Artificial Sequence
<220> FEATURE:
<223> OTHER INFORMATION: Affibody-fluorogen activating peptide fusion
      protein Her1-dL5-Her1 AffiFAP

<400> SEQUENCE: 12

Gly Pro Ser Lys Leu Ala Glu Ala Lys Tyr Ala Lys Glu Met Trp Ala
1               5                   10                  15

Ala Trp Glu Glu Ile Arg Asn Leu Pro Asn Leu Thr Gly Trp Gln Met
            20                  25                  30

Thr Ala Phe Ile Ala Lys Leu Val Asp Asp Pro Ser Gln Ser Ser Glu
        35                  40                  45

Leu Leu Ser Glu Ala Lys Lys Leu Asn Asp Ser Gln Ala Pro Lys Gly
    50                  55                  60

Ser Gln Ala Val Val Thr Gln Glu Pro Ser Val Thr Val Ser Pro Gly
65                  70                  75                  80

Gly Thr Val Ile Leu Thr Cys Gly Ser Gly Thr Gly Ala Val Thr Ser
                85                  90                  95

Gly His Tyr Ala Asn Trp Phe Gln Gln Lys Pro Gly Gln Ala Pro Arg
            100                 105                 110
```

Ala Leu Ile Phe Asp Thr Asp Lys Lys Tyr Ser Trp Thr Pro Gly Arg
                115                 120                 125

Phe Ser Gly Ser Leu Leu Gly Ala Lys Ala Ala Leu Thr Ile Ser Asp
            130                 135                 140

Ala Gln Pro Glu Asp Glu Ala Glu Tyr Tyr Cys Ser Leu Ser Asp Val
145                 150                 155                 160

Asp Gly Tyr Leu Phe Gly Gly Gly Thr Gln Leu Thr Val Leu Ser Gly
                165                 170                 175

Gly Gly Gly Ser Gly Gly Gly Gly Ser Gly Gly Gly Gly Ser Gly Gly
            180                 185                 190

Gly Gly Ser Gln Ala Val Val Thr Gln Glu Pro Ser Val Thr Val Ser
            195                 200                 205

Pro Gly Gly Thr Val Ile Leu Thr Cys Gly Ser Gly Thr Gly Ala Val
210                 215                 220

Thr Ser Gly His Tyr Ala Asn Trp Phe Gln Gln Lys Pro Gly Gln Ala
225                 230                 235                 240

Pro Arg Ala Leu Ile Phe Asp Thr Asp Lys Lys Tyr Ser Trp Thr Pro
                245                 250                 255

Gly Arg Phe Ser Gly Ser Leu Leu Gly Ala Lys Ala Ala Leu Thr Ile
            260                 265                 270

Ser Asp Ala Gln Pro Glu Asp Glu Ala Glu Tyr Tyr Cys Ser Leu Ser
            275                 280                 285

Asp Val Asp Gly Tyr Leu Phe Gly Gly Gly Thr Gln Leu Thr Val Leu
            290                 295                 300

Ser Gly Thr Ala Glu Ala Lys Tyr Ala Lys Glu Met Trp Ala Ala Trp
305                 310                 315                 320

Glu Glu Ile Arg Asn Leu Pro Asn Leu Thr Gly Trp Gln Met Thr Ala
                325                 330                 335

Phe Ile Ala Lys Leu Val Asp Asp Pro Ser Gln Ser Ser Glu Leu Leu
                340                 345                 350

Ser Glu Ala Lys Lys Leu Asn Asp Ser Gln Ala Pro Lys Leu Glu
            355                 360                 365

<210> SEQ ID NO 13
<211> LENGTH: 312
<212> TYPE: PRT
<213> ORGANISM: Artificial Sequence
<220> FEATURE:
<223> OTHER INFORMATION: Affibody-fluorogen activating peptide fusion
      protein dL5-Her2 AffiFAP

<400> SEQUENCE: 13

Gly Pro Ser Lys Leu Gln Ala Val Val Thr Gln Glu Pro Ser Val Thr
1               5                   10                  15

Val Ser Pro Gly Gly Thr Val Ile Leu Thr Cys Gly Ser Gly Thr Gly
            20                  25                  30

Ala Val Thr Ser His Tyr Ala Asn Trp Phe Gln Gln Lys Pro Gly Gln
            35                  40                  45

Ala Pro Arg Ala Leu Ile Phe Asp Thr Asp Lys Lys Tyr Ser Trp Thr
50                  55                  60

Pro Gly Arg Phe Ser Gly Ser Leu Leu Gly Ala Lys Ala Ala Leu Thr
65                  70                  75                  80

Ile Ser Asp Ala Gln Pro Glu Asp Glu Ala Glu Tyr Tyr Cys Ser Leu
                85                  90                  95

Ser Asp Val Asp Gly Tyr Leu Phe Gly Gly Gly Thr Gln Leu Thr Val
            100                 105                 110

-continued

```
Leu Ser Gly Gly Gly Ser Gly Gly Gly Ser Gly Gly Gly
        115                 120                 125
Ser Gly Gly Gly Ser Gln Ala Val Val Thr Gln Glu Pro Ser Val
    130                 135                 140
Thr Val Ser Pro Gly Gly Thr Val Ile Leu Thr Cys Gly Ser Gly Thr
145                 150                 155                 160
Gly Ala Val Thr Ser Gly His Tyr Ala Asn Trp Phe Gln Gln Lys Pro
                165                 170                 175
Gly Gln Ala Pro Arg Ala Leu Ile Phe Asp Thr Asp Lys Lys Tyr Ser
                180                 185                 190
Trp Thr Pro Gly Arg Phe Ser Gly Ser Leu Leu Gly Ala Lys Ala Ala
                195                 200                 205
Leu Thr Ile Ser Asp Ala Gln Pro Glu Asp Glu Ala Glu Tyr Tyr Cys
                210                 215                 220
Ser Leu Ser Asp Val Asp Gly Tyr Leu Phe Gly Gly Thr Gln Leu
225                 230                 235                 240
Thr Val Leu Ser Ala Ser Gly Ser Thr Ser Gly Thr Val Glu Asn Lys
                245                 250                 255
Phe Asn Lys Glu Met Arg Asn Ala Tyr Trp Glu Ile Ala Leu Leu Pro
                260                 265                 270
Asn Leu Asn Asn Gln Gln Lys Arg Ala Phe Ile Arg Ser Leu Tyr Asp
                275                 280                 285
Asp Pro Ser Gln Ser Ala Asn Leu Leu Ala Glu Ala Lys Lys Leu Asn
                290                 295                 300
Asp Ala Gln Ala Pro Lys Leu Glu
305                 310

<210> SEQ ID NO 14
<211> LENGTH: 311
<212> TYPE: PRT
<213> ORGANISM: Artificial Sequence
<220> FEATURE:
<223> OTHER INFORMATION: Affibody-fluorogen activating peptide fusion
      protein Her2-dL5 AffiFAP

<400> SEQUENCE: 14

Gly Pro Ser Lys Leu Val Glu Asn Lys Phe Asn Lys Glu Met Arg Asn
1               5                   10                  15
Ala Tyr Trp Glu Ile Ala Leu Leu Pro Asn Leu Asn Asn Gln Gln Lys
                20                  25                  30
Arg Ala Phe Ile Arg Ser Leu Tyr Asp Asp Pro Ser Gln Ser Ala Asn
                35                  40                  45
Leu Leu Ala Glu Ala Lys Lys Leu Asn Asp Ala Gln Ala Pro Lys Gly
            50                  55                  60
Ser Thr Ser Gly Thr Gln Ala Val Val Thr Gln Glu Pro Ser Val Thr
65              70                  75                  80
Val Ser Pro Gly Gly Thr Val Ile Leu Thr Cys Gly Ser Gly Thr Gly
                85                  90                  95
Ala Val Thr Ser Gly His Tyr Ala Asn Trp Phe Gln Gln Lys Pro Gly
                100                 105                 110
Gln Ala Pro Arg Ala Leu Ile Phe Asp Thr Asp Lys Lys Tyr Ser Trp
                115                 120                 125
Thr Pro Gly Arg Phe Ser Gly Ser Leu Leu Gly Ala Lys Ala Ala Leu
            130                 135                 140
Thr Ile Ser Asp Ala Gln Pro Glu Asp Glu Ala Glu Tyr Tyr Cys Ser
```

```
145                 150                 155                 160
Leu Ser Asp Val Asp Gly Tyr Leu Phe Gly Gly Gly Thr Gln Leu Thr
                165                 170                 175

Val Leu Ser Gly Gly Gly Gly Ser Gly Gly Gly Ser Gly Gly Gly
            180                 185                 190

Gly Ser Gly Gly Gly Ser Gln Ala Val Val Thr Gln Glu Pro Ser
        195                 200                 205

Val Thr Val Ser Pro Gly Gly Thr Val Ile Leu Thr Cys Gly Ser Gly
    210                 215                 220

Thr Gly Ala Val Thr Ser Gly His Tyr Ala Asn Trp Phe Gln Gln Lys
225                 230                 235                 240

Pro Gly Gln Ala Pro Arg Ala Leu Ile Phe Asp Thr Asp Lys Lys Tyr
                245                 250                 255

Ser Trp Thr Pro Gly Arg Phe Ser Gly Ser Leu Leu Gly Ala Lys Ala
            260                 265                 270

Ala Leu Thr Ile Ser Asp Ala Gln Pro Glu Asp Glu Ala Glu Tyr Tyr
        275                 280                 285

Cys Ser Leu Ser Asp Val Asp Gly Tyr Leu Phe Gly Gly Gly Thr Gln
290                 295                 300

Leu Thr Val Leu Ser Leu Glu
305                 310

<210> SEQ ID NO 15
<211> LENGTH: 371
<212> TYPE: PRT
<213> ORGANISM: Artificial Sequence
<220> FEATURE:
<223> OTHER INFORMATION: Affibody-fluorogen activating peptide fusion
      protein Her2-dL5-Her2 AffiFAP

<400> SEQUENCE: 15

Gly Pro Ser Lys Leu Val Glu Asn Lys Phe Asn Lys Glu Met Arg Asn
1               5                   10                  15

Ala Tyr Trp Glu Ile Ala Leu Leu Pro Asn Leu Asn Asn Gln Gln Lys
            20                  25                  30

Arg Ala Phe Ile Arg Ser Leu Tyr Asp Asp Pro Ser Gln Ser Ala Asn
        35                  40                  45

Leu Leu Ala Glu Ala Lys Lys Leu Asn Asp Ala Gln Ala Pro Lys Gly
    50                  55                  60

Ser Thr Ser Gly Thr Gln Ala Val Val Thr Gln Glu Pro Ser Val Thr
65                  70                  75                  80

Val Ser Pro Gly Gly Thr Val Ile Leu Thr Cys Gly Ser Gly Thr Gly
            85                  90                  95

Ala Val Thr Ser Gly His Tyr Ala Asn Trp Phe Gln Gln Lys Pro Gly
        100                 105                 110

Gln Ala Pro Arg Ala Leu Ile Phe Asp Thr Asp Lys Lys Tyr Ser Trp
    115                 120                 125

Thr Pro Gly Arg Phe Ser Gly Ser Leu Leu Gly Ala Lys Ala Ala Leu
130                 135                 140

Thr Ile Ser Asp Ala Gln Pro Glu Asp Glu Ala Glu Tyr Tyr Cys Ser
145                 150                 155                 160

Leu Ser Asp Val Asp Gly Tyr Leu Phe Gly Gly Gly Thr Gln Leu Thr
                165                 170                 175

Val Leu Ser Gly Gly Gly Gly Ser Gly Gly Gly Ser Gly Gly Gly
            180                 185                 190
```

```
Gly Ser Gly Gly Gly Ser Gln Ala Val Val Thr Gln Glu Pro Ser
        195                 200                 205

Val Thr Val Ser Pro Gly Gly Thr Val Ile Leu Thr Cys Gly Ser Gly
    210                 215                 220

Thr Gly Ala Val Thr Ser Gly His Tyr Ala Asn Trp Phe Gln Lys
225                 230                 235                 240

Pro Gly Gln Ala Pro Arg Ala Leu Ile Phe Asp Thr Asp Lys Lys Tyr
                245                 250                 255

Ser Trp Thr Pro Gly Arg Phe Ser Gly Ser Leu Leu Gly Ala Lys Ala
                260                 265                 270

Ala Leu Thr Ile Ser Asp Ala Gln Pro Glu Asp Glu Ala Tyr Tyr
                275                 280                 285

Cys Ser Leu Ser Asp Val Asp Gly Tyr Leu Phe Gly Gly Gly Thr Gln
                290                 295                 300

Leu Thr Val Leu Ser Gly Thr Val Glu Asn Lys Phe Asn Lys Glu Met
305                 310                 315                 320

Arg Asn Ala Tyr Trp Glu Ile Ala Leu Leu Pro Asn Leu Asn Asn Gln
                325                 330                 335

Gln Lys Arg Ala Phe Ile Arg Ser Leu Tyr Asp Asp Pro Ser Gln Ser
                340                 345                 350

Ala Asn Leu Leu Ala Glu Ala Lys Lys Leu Asn Asp Ala Gln Ala Pro
                355                 360                 365

Lys Leu Glu
    370

<210> SEQ ID NO 16
<211> LENGTH: 5
<212> TYPE: PRT
<213> ORGANISM: Artificial Sequence
<220> FEATURE:
<223> OTHER INFORMATION: fusion protein peptide linker G4S

<400> SEQUENCE: 16

Gly Gly Gly Gly Ser
1               5

<210> SEQ ID NO 17
<211> LENGTH: 58
<212> TYPE: PRT
<213> ORGANISM: Artificial Sequence
<220> FEATURE:
<223> OTHER INFORMATION: Affibody ZHER2:342

<400> SEQUENCE: 17

Val Glu Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
                20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 18
<211> LENGTH: 58
<212> TYPE: PRT
<213> ORGANISM: Artificial Sequence
<220> FEATURE:
<223> OTHER INFORMATION: Affibody ZEGFR:1907
```

```
<400> SEQUENCE: 18

Ala Glu Ala Lys Tyr Ala Lys Glu Met Trp Ala Ala Trp Glu Glu Ile
1               5                   10                  15

Arg Asn Leu Pro Asn Leu Thr Gly Trp Gln Met Thr Ala Phe Ile Ala
            20                  25                  30

Lys Leu Val Asp Asp Pro Ser Gln Ser Ser Glu Leu Leu Ser Glu Ala
            35                  40                  45

Lys Lys Leu Asn Asp Ser Gln Ala Pro Lys
50                  55
```

ACTIVATABLE TWO-COMPONENT PHOTOSENSITIZERS

CROSS REFERENCE TO RELATED APPLICATIONS

This application is a divisional of U.S. patent application Ser. No. 15/527,061, filed May 16, 2017, now U.S. Pat. No. 10,434,177, issued on Oct. 8, 2019, which is a national phase of International Patent Application No. PCT/US2015/061051, filed Nov. 17, 2015, which claims the benefit of U.S. Provisional Patent Application No. 62/123,489, filed Nov. 17, 2014, each of which is incorporated herein by reference in its entirety.

STATEMENT REGARDING FEDERAL FUNDING

This invention was made with government support under Grant No. 1R01EB017268, awarded by the National Institutes of Health. The government has certain rights in this invention.

The Sequence Listing associated with this application is filed in electronic format via EFS-Web and is hereby incorporated by reference into the specification in its entirety. The name of the text file containing the Sequence Listing is 1904760_ST25.txt. The size of the text file is 32,183 bytes, and the text file was created on Sep. 5, 2019.

Compositions useful in photodynamic therapy are provided, as well as related methods.

Photodynamic therapy is one of the least invasive and most site-specific treatments for cancer, which utilizes the light-inducible toxicity of photosensitizers to reduce cancer development. When being exposed to light of corresponding wavelength(s), a photosensitizer is able to produce reactive oxygen species (ROS) that interfere with many key processes in cell metabolism to cause cell necrosis and/or apoptosis, and to eventually result in destruction of the target tissues. In particular, the minimal invasion and off-site toxicity of photodynamic therapy offers great alternatives in treatment for localized superficial malignant and premalignant tumors.

Conventional photosensitizers show the disadvantage of lack of tumor selectivity, which results in serious off-target damage to normal tissues and limits its applications in oncologic therapy. Researchers have recently tried to improve tumor specificity by conjugating photosensitizers to tumor-associating moieties (3rd generation photosensitizer). For example, the photosensitizer has been coupled to monoclonal antibodies (mAbs) specific to tumor-associated antigens, so that photosensitizer-mAbs can be selectively delivered to the tumor site. However, the large size of antibody results in slow clearance rate and limited tissue penetration. Moreover, the highly specific antigen recognition by mAbs is often compromised by the high ratio of photosensitizer substitution, which alters the overall charge and bio-distribution of these conjugates.

To reduce nonspecific phototoxicity to nearby normal tissue, one approach is to develop photosensitizers that can only be activated for ROS generation with the presence of both light illumination and cell-specific targeting. The cell-targeting step provides a controllable photodynamic therapy by guiding ROS generation and restraining damage to abnormal tissues. Therefore, the damage to the surrounding non-targeted tissue is minimized due to low cytotoxicity of inactive photosensitizer. Spring B. Q., et al. reported an activatable photoimmunetherapy for targeting A431 cancer cell, in which multiple self-quenching photosensitizer were conjugated to antibody against EGFR. Upon binding, the phototoxicity and fluorescence of photosensitizer are activated by lysosomal proteolysis (Spring B. Q., et al. Selective treatment and monitoring of disseminated cancer micrometastases in vivo using dual-function, activatable immunoconjugates. Proc. Natl. Acad. Sci. U.S.A. 111, E933-E942 (2014)) with 7-fold enhancement. Efficient, safe and effective photodynamic therapies are needed. Improvements to photosensitizers toward higher ROS-generating efficiency, better photostability, specificity and greater versatility are urgently needed.

SUMMARY

To address these issues, the present invention includes activatable genetically encoded dye-protein two-component photosensitizers. Upon near infrared illumination, an exemplary di-iodide modified malachite green fluorogen (MG2I) bound by a fluorogen-activating protein ($FAP_{dL5}$) is able to generate singlet oxygen, which induces acute cytotoxicity and leads to cell death. The utility of the two-component photosensitizer described herein is demonstrated by effective and specific cell killing properties with FAP genetically targeted to different cellular compartments, and has been successfully used to photo-ablate heart functions of larval/adult zebrafish. In another example, a FAP-tagged affinity probe was applied in the system to selectively kill cancer cells. In vivo study has shown that compounds and methods described herein can effectively reduce A431 tumor growth in nude mice. Overall, the targeted photodynamic therapy strategy and design of the two-component photosensitizer system allows for its application in tissues and in vivo visualization during photodynamic therapy due to near infrared absorption and fluorescent readout. It can also facilitate the selection of stable cells and transgenic animals, which are primed for imaging, photoablation or photosensitization studies, depending on the dye and light-dose employed in the study.

According to one aspect of the invention, a heavy atom-modified malachite green derivative is provided, having the structure:

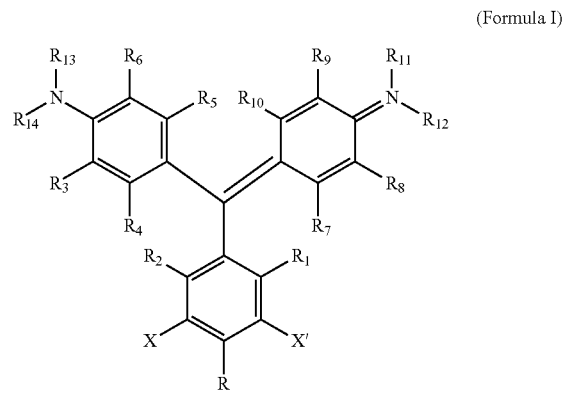

(Formula I)

where X and X' are, independently, heavy atoms, R1, R2, R3, R4, R5, R6, R7, R8, R9, and R10 are, independently, H or F, R11, R12, R13 and R14 are, independently, methyl, H, aziridine or azetidine, wherein when R11, R12, R13, and/or R14 are aziridine or azetidine, R11 and R12 form a single ring and/or R13 and R14 form a single ring, and where R is selected from —H, —OH, —COO⁻, —SO₃⁻, —PO₄⁻, —NO$_2$, —NH$_2$, —N(CH$_3$)(R15), —OR16, alkyl, ether, polyether, PEG$_{1-30}$, —(C$_1$-C$_4$ alkyl)-R17, heterocyles containing N, S or O atoms, substituted acetylenic groups, cyano, and carbohydrate groups, wherein R15 and R16 are: straight- or branched-chain alkyl; straight or branched-chain C$_{1-6}$ alkyl; straight-chain or branched poly(C$_1$-C$_4$ alkyl amide); straight-chain or branched poly(C$_1$-C$_4$ alkyl amide) having from 2 to 6 amide moieties; poly(C$_1$-C$_4$ alkylene glycol); poly(C$_1$-C$_4$ alkylene glycol) having from 2 to 30 or from 2-10 C$_1$-C$_4$ alkylene glycol moieties; straight-chain or branched poly(C$_1$-C$_4$ alkyl amide):poly(C$_1$-C$_4$ alkylene glycol) diblock copolymer; straight-chain or branched poly(C$_1$-C$_4$ alkyl amide):poly(C$_1$-C$_4$ alkylene glycol) diblock copolymer having from 2 to 6 amide moieties and from 2 to 10 C$_1$-C$_4$ alkylene glycol moieties; sulfonyl or bis-sulfonyl-terminated straight-chain or branched poly(C$_1$-C$_4$ alkyl amide), optionally having from 2 to 6 amide moieties; bis-taurine branched poly(C$_1$-C$_4$ alkyl amide), optionally having from 2 to 6 amide moieties; ethyl butyrate; C$_{1-6}$ alkyl C$_{1-6}$ alkanoate; —(CH$_2$)$_n$—C(O)—O—(CH$_2$)$_m$—CH$_3$, where n=1-4 and m=0-3, and wherein R17 is selected from H, —OH, —COO$^-$, —SO$_3^-$, —PO$_4^-$, —NO$_2$, or —NH$_2$. In one aspect, R1, R2, R3, R4, R5, R6, R7, R8, R9, and R10 are H. In another aspect, X and X' are independently Br, I, As, Se, Ga, Ge, or Sb, for example X and X' are independently Br or I, or X and X' are I. In another aspect, R11, R12, R13 and R14 are, independently, methyl or H, or R11, R12, R13 and R14 are methyl. In yet another aspect, R is —OR16, and R16 is ethylbutyrate. In another aspect, the heavy atom-modified malachite green derivative has the structure:

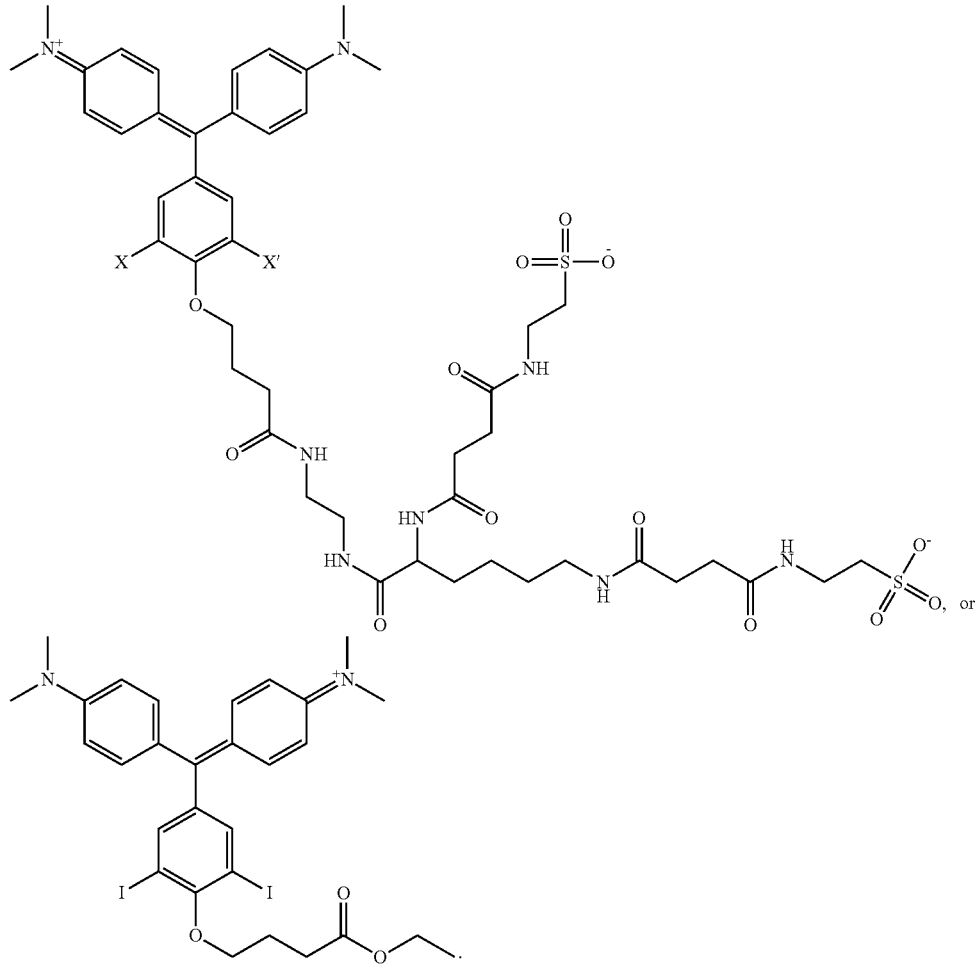

In another aspect, a method of targeting and killing cells is provided, comprising: contacting cells with a targeting activator composition comprising a targeting moiety that selectively binds a target compound of the cell, and an activator moiety that selectively binds a heavy atom-modified malachite green derivative according to any aspect described herein, having an excitation wavelength so that the heavy atom-modified malachite green derivative produces singlet oxygen when bound by the targeting activator and exposed to light at the excitation wavelength; contacting cells with the heavy atom-modified malachite green derivative; and exposing the cells to light at an excitation wavelength of the targeting activator-bound heavy atom-modified malachite green derivative. The light can be produced by any light-emitting device, such as a lamp, a light-emitting diode, or a laser, as are broadly known by those of skill in the art. According to one aspect, the activator moiety is fusion protein of an scFv activator moiety and an affibody targeting moiety. In one aspect, the scFv is an L5-MG scFv peptide, optionally SEQ ID NOS: 1-4. In another aspect, the targeting moiety is selective for (binds selectively to in the context of the described use) an epidermal growth factor receptor, for example, HER1 (human epidermal growth factor receptor 1) or HER2 (human epidermal growth factor receptor 2). In one aspect, the targeting activator comprises a sequence selected from SEQ ID NOS: 1-4, 10-15, 17 and 18.

According to a further aspect of the invention, a kit is provided, comprising: a first vessel containing the heavy atom-modified malachite green derivative according to any aspect described herein; and a targeting activator composition in the first vessel or in a second vessel, containing comprising a targeting moiety that selectively binds a target compound of a cell, and an activator moiety that selectively binds a heavy atom-modified malachite green derivative having an excitation wavelength so that the heavy atom-modified malachite green derivative produces singlet oxygen when bound by the targeting activator and exposed to light at the excitation wavelength in a pharmaceutically-acceptable excipient. According to one aspect, the activator moiety is fusion protein of an scFv activator moiety and an affibody targeting moiety. In one aspect, the scFv is an L5-MG scFv peptide, optionally SEQ ID NOS: 1-4. In another aspect, the targeting moiety is selective for (binds selectively to in the context of the described use) an epidermal growth factor receptor, for example, HER1 (human epidermal growth factor receptor 1) or HER2 (human epidermal growth factor receptor 2). In one aspect, the targeting activator comprises a sequence selected from SEQ ID NOS: 1-4, 10-15, 17 and 18.

In another aspect, a method of targeting and killing cells in a patient is provided, comprising: administering to the patient an effective amount of a targeting activator composition comprising a targeting moiety that selectively binds to targeted cells, and an activator moiety that selectively binds the heavy atom-modified malachite green derivative according to any aspect described herein, having an excitation wavelength so that the heavy atom-modified malachite green derivative produces singlet oxygen when bound by the targeting activator and exposed to light at the excitation wavelength; administering to the patient an effective amount of the heavy atom-modified malachite green derivative; and exposing the cells to light at an excitation wavelength of the targeting activator-bound heavy atom-modified malachite green derivative, thereby killing the cells. According to one aspect, the activator moiety is fusion protein of an scFv activator moiety and an affibody targeting moiety. In one aspect, the scFv is an L5-MG scFv peptide, optionally SEQ ID NOS: 1-4. In another aspect, the targeting moiety is selective for (binds selectively to in the context of the described use) an epidermal growth factor receptor, for example, HER1 (human epidermal growth factor receptor 1) or HER2 (human epidermal growth factor receptor 2). In one aspect, the targeting activator comprises a sequence selected from SEQ ID NOS: 1-4, 10-15, 17 and 18.

BRIEF DESCRIPTION OF THE DRAWINGS

FIGS. 2A and 2B provide exemplary peptide sequences for biosensor-activating scFvs (SEQ ID NOS: 1-4). Hyphens designate the core sequences. Additional FAPs are provided in FIG. 1B (SEQ ID NOS: 5-7).

Figure 3D:
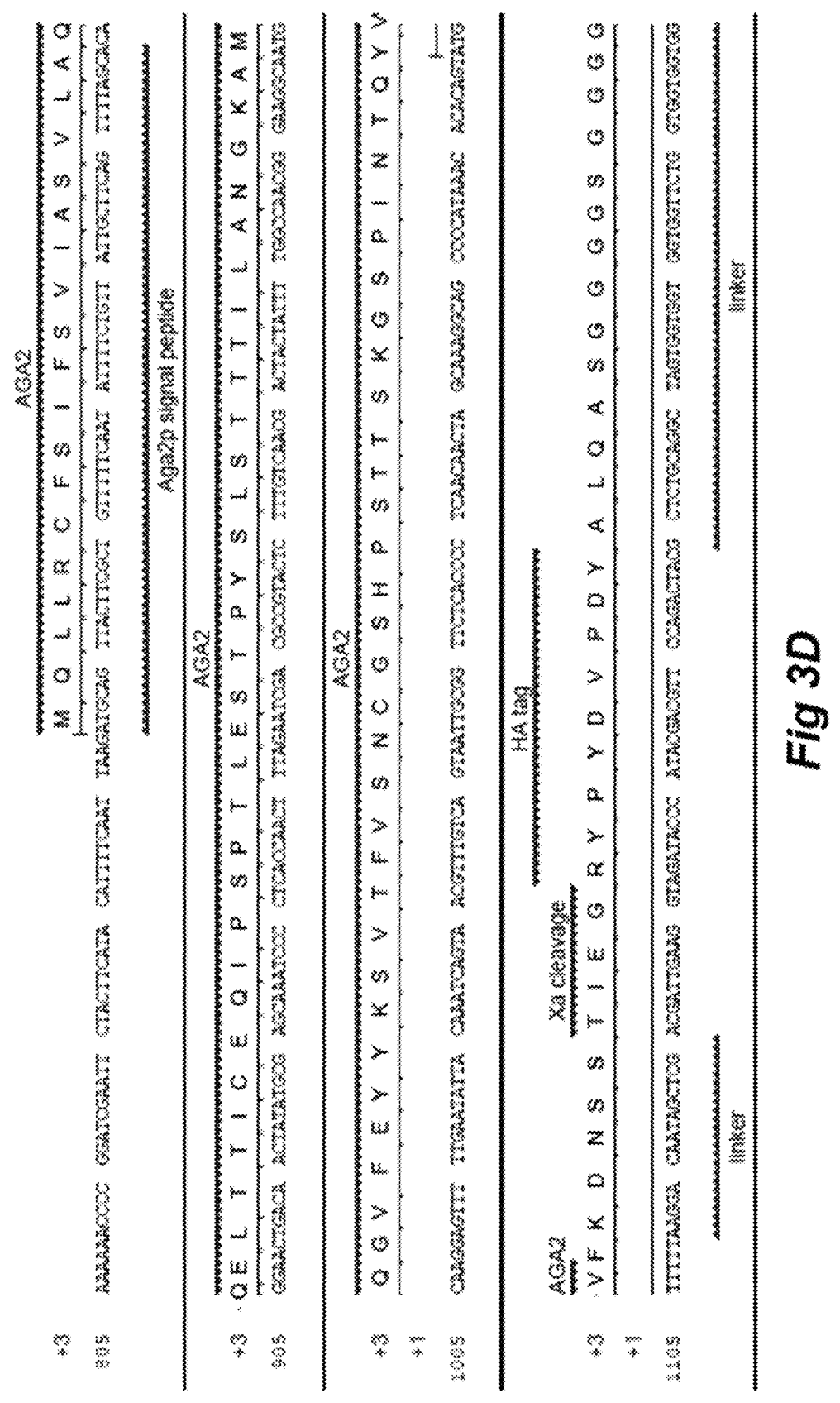

FIG. 3A depicts the DNA sequence of a construct encoding the L5-MG E52D pPNL6 fusion protein (SEQ ID NO: 8). FIGS. 3D and 3E together depict region of the construct encoding L5-MG E52D mapped onto the nucleotide sequence of the relevant portion of pPNL6 L5-MG E52D (SEQ ID NO: 9).

FIG. 7A) KD measurement of MG-dL5 and MG2I-dL5, FIG. 7B) absorption spectra of 1 µM MG2I and MG2I with 5 µM dL5 (shorter wavelength absorption peak), FIG. 7C): fluorescence quantum yield measurement of MG2I-dL5 (squares) using Cy5 as standard (circles).

FIGS. 16A and 16B provide sequences of AffiFAP peptides as described below (SEQ ID NOS: 10-15).

FIG. 18 shows the selective killing of SKBR3 cancer cells. 100 nM HER2 conjugated dL5 was first added to the cells following by 100 nM MG2I.

DETAILED DESCRIPTION

Figure 1A:
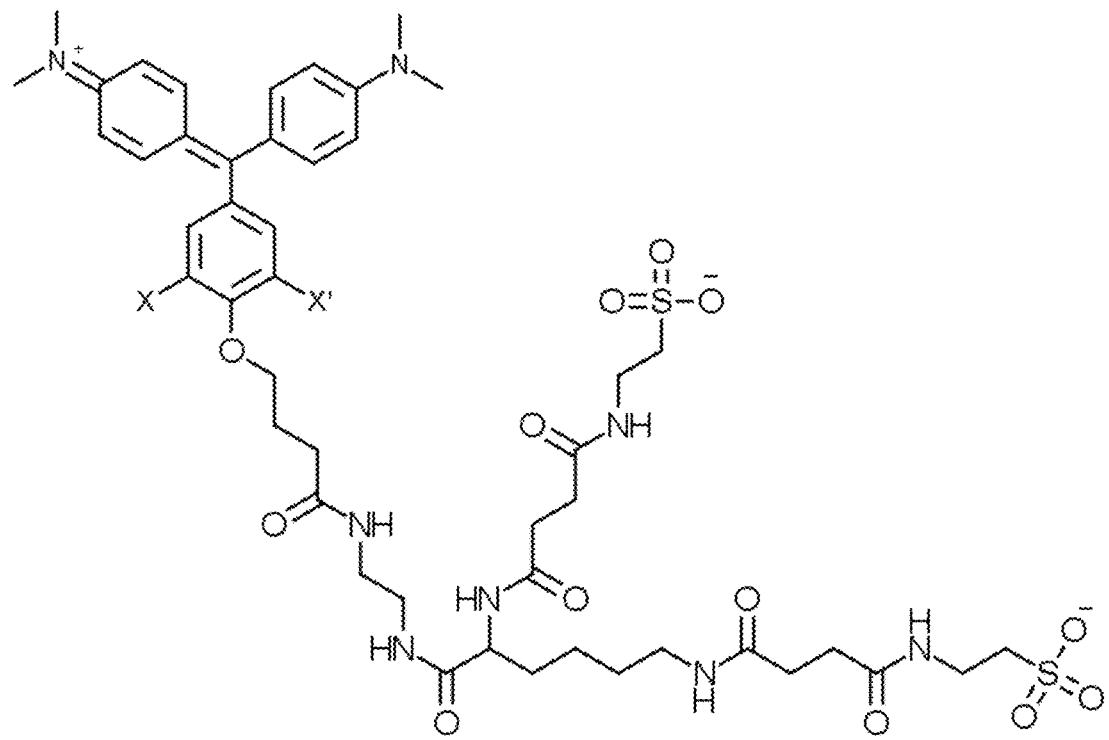
FIGS. 1A and 1B provide two aspects of a heavy atom-modified malachite green derivative, as descried herein.

Other than in the operating examples, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

For definitions provided herein, those definitions refer to word forms, cognates and grammatical variants of those words or phrases.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer.

A polymer "comprises" or is "derived from" a stated monomer if that monomer is incorporated into the polymer. Thus, the incorporated monomer that the polymer comprises is not the same as the monomer prior to incorporation into the polymer, in that at the very least, during incorporation of the monomer, certain groups, e.g. terminal groups, that are modified during polymerization are changed, removed, and/or relocated, and certain bonds may be added, removed, and/or modified. An incorporated monomer is referred to as a "residue" of that monomer. A polymer is said to comprise a specific type of linkage if that linkage is present in the polymer. Unless otherwise specified, molecular weight for polymer compositions refers to weight average molecular weight ($M_W$). As an example, the molecular weight of poly(ethylene glycol), having an average of 11 ethylene glycol residues, is expressed in terms of $M_W$. A "moiety" is a portion of a molecule, compound or composition, and includes a residue or group of residues within a larger polymer, for example as described below.

"Alkyl" refers to straight, branched chain, or cyclic hydrocarbon groups including from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Hydrocarbon" refers to a compound, group or moiety solely consisting of C and H atoms.

"Alkylene" and "substituted alkylene" refer to divalent alkyl and divalent substituted alkyl, respectively, including, without limitation, ethylene (—CH$_2$—CH$_2$—). "Optionally substituted alkylene" refers to alkylene or substituted alkylene. A polyether is a polymer comprising a plurality of ether groups, such as poly(alkylene oxides), comprising the moiety —[O—R—]n, in which n is an integer of from 2 to 100 or greater, for example 2 to 100, or 5-20, or from 2 to any integer less than 25. As would be recognized for polyethers, as with any polymer composition referenced herein, n, or like references, is calculated in reference to a polydisperse population of molecules, with n being representative of the average number of units of a referenced moiety, determined by reference to the $M_W$ of the polyether or polymer composition. The population of molecules has a dispersity (dispersity, calculated by dividing the weight average molecular weight by the number average molecular weight) within tolerances acceptable for production of a composition as described herein, for example for gas-separation purposes.

"Aryl," alone or in combination refers to an aromatic monocyclic or bicyclic ring system such as phenyl or naphthyl. "Aryl" also includes aromatic ring systems that are optionally fused with a cycloalkyl ring. A "substituted aryl" is an aryl that is independently substituted with one or more substituents attached at any available atom to produce a stable compound, wherein the substituents are as described herein. "Optionally substituted aryl" refers to aryl or substituted aryl. "Arylene" denotes divalent aryl, and "substituted arylene" refers to divalent substituted aryl. "Optionally substituted arylene" refers to arylene or substituted arylene. As used herein, a "phenol" group is hydroxyphenyl, for example a peptide backbone comprising a hydroxyphenyl group.

A "polyether" may be any poly(alkylene glycol), and in one aspect, a poly($C_2$-$C_6$ alkylene glycol), having the structure —[R1—O]$_n$—, where R1 is linear or branched alkylene, such as a $C_2$-$C_8$ alkylene, or mixtures of two or more different alkylenes, such as $C_2$-$C_8$ alkylenes. n can vary, depending on the ultimate use of the composition, for example from 2 to 100, from 2 to 50, from 2 to 25, from 5 to 20, or from 8 to 15.

A "heavy atom-modified malachite green derivative" is a composition having the structure:

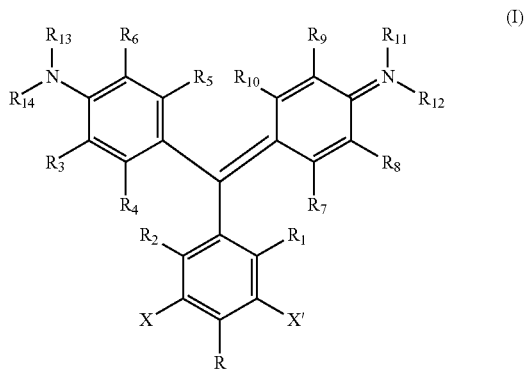

(I)

where X and X' are, independently, heavy atoms. By "heavy atoms" it is meant an atom that produces the heavy atom effect on fluorescence (See, e.g., Guilbault, G. G., Ed., *Practical Fluorescence*, Second Edition, Marcel Dekker, Inc. New York, N.Y. (1990), pp. 88-92). Specifically, heavy atoms have the generalized effect of decreased quantum yield, and an increase in intersystem crossing. Examples of such heavy atoms include the halogens Br, and I, and other atoms, such as As, Se, Ga, Ge, and Sb. In one aspect, the heavy atom is Br or I, and in another, X and X' are both I.

R1, R2, R3, R4, R5, R6, R7, R8, R9, and R10 are, independently H or F, in any combination or permutation. F at one or more of R1, R2, R3, R4, R5, R6, R7, R8, R9, and R10 has the effect of at least shifting the absorbance and excitation spectra of the composition. In one aspect, R1, R2, R3, R4, R5, R6, R7, R8, R9, and R10 are all H. Other examples are illustrated in the following table:

TABLE 1

| R1 | R2 | R3 | R4 | R5 | R6 | R7 | R8 | R9 | R10 |
|----|----|----|----|----|----|----|----|----|-----|
| F  | F  | H  | H  | H  | H  | H  | H  | H  | H   |
| H  | H  | H  | F  | H  | H  | F  | H  | H  | H   |
| H  | H  | H  | F  | H  | F  | F  | H  | F  | H   |
| H  | H  | H  | F  | F  | H  | F  | F  | H  | H   |
| H  | H  | F  | H  | H  | H  | H  | F  | H  | H   |

The following provides properties of various fluorinated malachite green derivatives.

TABLE 2

| Fluorinated position | y band abs max (nm) | x band abs max (nm) | +dL5 fluor ex (nm) | +dL5 fluor em (nm) |
|---|---|---|---|---|
| None (Standard) | 466 | 606 | 636 (482) | 668 |
| R1, R2-2F | 439 | 630 | 678 | 712 |
| R1, R2, X, X'-4F | 430 | 652 | 712 | 750 |
| R4, R7-2F | 480 | 618 | 644 | 678 |
| R4, R6, R7, R9-4F | 516 | 628 | 644 (530) | 686 |
| R4, R5, R7, R8-4F | 504 | 636 | none | none |
| R3, R8 | 510 | 630 | none | none |
| R1, R2-2F, X, X'-2I | ~430 | ~652 | ~712 | ~750 (expected) |
| X, X'-2I | 440 | 628 | 666 | 693 |
| X, X'-2F | 440 | 630 | 678 | 712 |

Fluorinations on MG have caused various red shifts of the x band, from 10 to 80 nm. While the shift of y band depends on the fluorinated position, a blue shift with decreased intensity is observed when fluorine substitution is on the phenyl ring. If hydrogen of the diamino ring is replaced with fluorine, the y band is red shifted with an increase of intensity, and the x and y band are brought closer. MG-4F (R1, R2, X, X'=F) ester has an emission maximum at 750 nm when bound with dL5.

R11, R12, R13 and R14 are, independently, methyl, H, aziridine or azetidine. Where R11, R12, R13, and/or R14 are aziridine

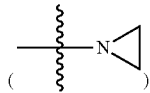

or azetidine

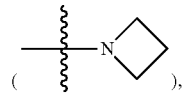

R11 and R12 form a single ring and/or R13 and R14 form a single ring.

R is selected from —H, —OH, —COO⁻, —SO$_3^-$, —PO$_4^-$, —NO$_2$, —NH$_2$, —N(CH$_3$)(R15), —OR16, alkyl, ether, polyether, PEG$_{1-30}$, —(C$_1$-C$_4$ alkyl)-R17, heterocycles containing N, S or O atoms, substituted acetylenic groups, cyano, and carbohydrate groups, wherein R15 and R16 are: straight- or branched-chain alkyl; straight or branched-chain C$_{1-6}$ alkyl; straight-chain or branched poly(C$_1$-C$_4$ alkyl amide); straight-chain or branched poly(C$_1$-C$_4$ alkyl amide) having from 2 to 6 amide moieties; poly(C$_1$-C$_4$ alkylene glycol); poly(C$_1$-C$_4$ alkylene glycol) having from 2 to 30, e.g., from 2-10 C$_1$-C$_4$ alkylene glycol moieties; straight-chain or branched poly(C$_1$-C$_4$ alkyl amide):poly(C$_1$-C$_4$ alkylene glycol) diblock copolymer; straight-chain or branched poly(C$_1$-C$_4$ alkyl amide):poly(C$_1$-C$_4$ alkylene glycol) diblock copolymer having from 2 to 6 amide moieties and from 2 to 10 C$_1$-C$_4$ alkylene glycol moieties; sulfonyl or bis-sulfonyl-terminated straight-chain or branched poly(C$_1$-C$_4$ alkyl amide), optionally having from 2 to 6 amide moieties; bis-taurine branched poly(C$_1$-C$_4$ alkyl amide), optionally having from 2 to 6 amide moieties; ethyl butyrate; C$_{1-6}$ alkyl C$_{1-6}$ alkanoate; —(CH$_2$)$_n$—C(O)—O—(CH$_2$)$_m$—CH$_3$, where n=1-4 and m=0-3, wherein R17 is selected from H, —OH, —COO⁻, —SO$_3^-$, —PO$_4^-$, —NO$_2$, or —NH$_2$.

Non-limiting examples of the compound are structures (III) and (IV):

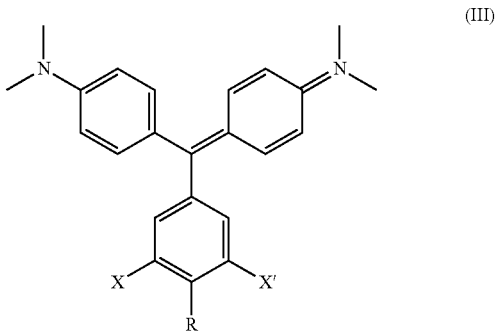

(III)

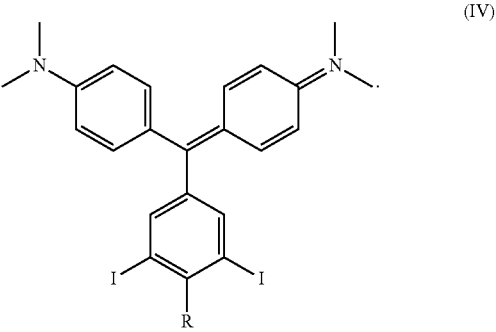

(IV)

Figure 1B:
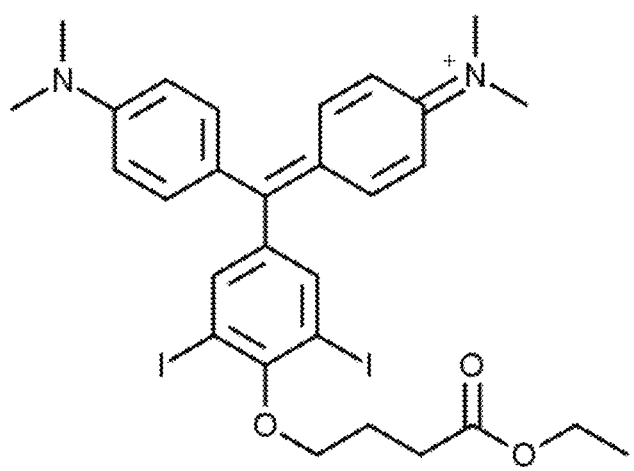
Figure 3B:
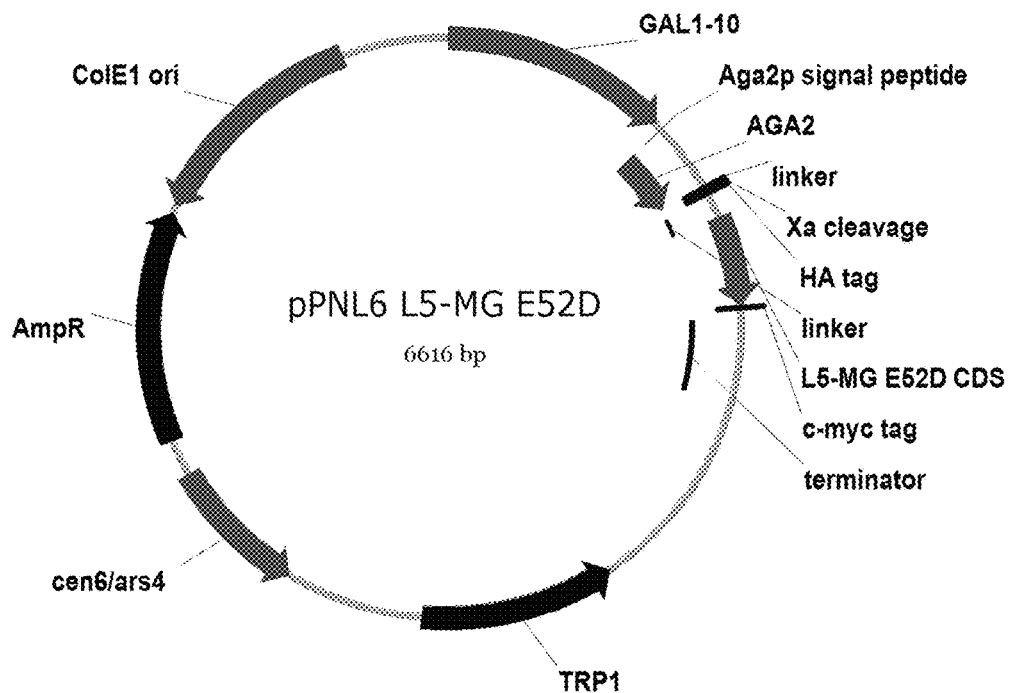
FIGS. 3B and 3C depict the construct pPNL6 L5-MG E52D.
Figure 3C:
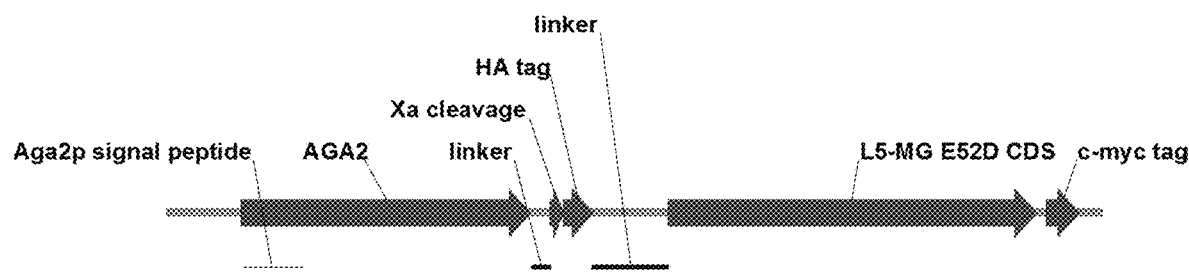
Figure 3E:
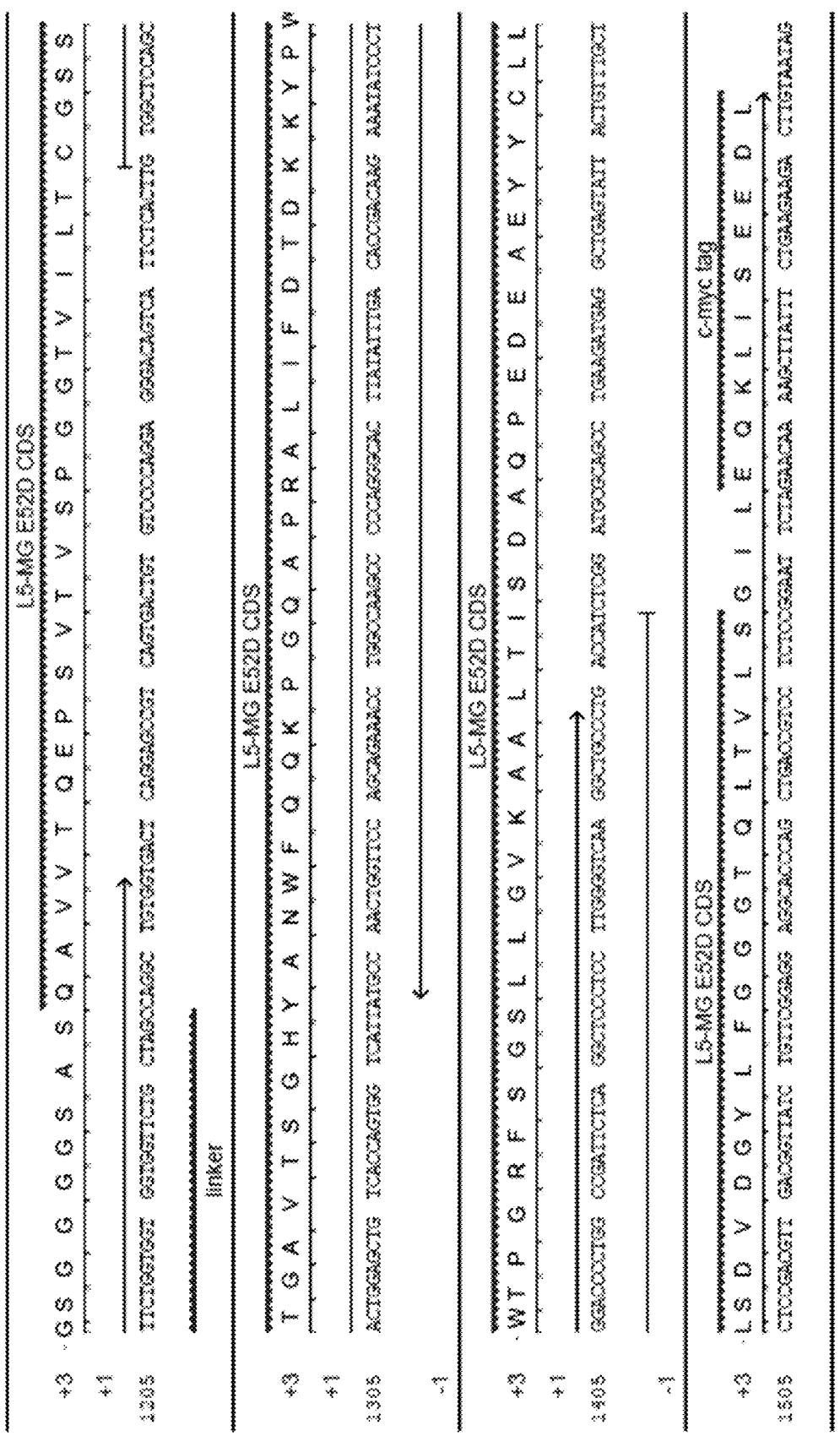

Non-limiting examples of additional compounds are shown in FIGS. 1A and 1B, wherein X and X' are, independently, heavy atoms, and in one aspect, X and X' are, independently, Br and/or I, and in another aspect, both X and X' are iodo.

Provided herein are methods of killing cells in vitro or in vivo, and compounds and compositions useful in killing cells. According to one aspect of the invention, a method of targeting and killing cells is provided. The method comprises contacting cells with a targeting activator composition comprising a targeting moiety that selectively binds a target compound of the cell, and an activator moiety that selectively binds a heavy atom-modified malachite green derivative having an excitation wavelength so that the heavy atom-modified malachite green derivative produces singlet oxygen when bound by the targeting activator and exposed to light at the excitation wavelength; contacting cells with the heavy atom-modified malachite green derivative; and exposing the cells to light at an excitation wavelength of the targeting activator-bound heavy atom-modified malachite green derivative. The heavy atom-modified malachite green derivative is any heavy atom-modified malachite green derivative.

In another aspect, a method of targeting and killing cells in a patient is provided, for, e.g., treatment of cancer, hyperplasia, autoimmune diseases, immune disorders, and infections.

As used herein, a "cell" may be autologous, allogeneic, or xenogeneic, such as cancer cells, immune cells, bacteria cells, fungal cells, parasite cells, and viral-infected cells.

In the methods described herein for targeting and killing cells, the targeted activator and the heavy atom-modified malachite green derivative is used/administered in an amount effective to selectively kill the targeted cells. For each specific targeted activator and heavy atom-modified malachite green derivative, the effective amounts may vary, and amounts/dosages, as with any drug product, are limited by minimum effective dosage and maximum safe dosage. The effective range for the targeted activator and heavy atom-modified malachite green derivative ranges from 1 pM (picomolar, that is picomoles liter$^{-1}$) and 10 mM (millimolar), for example, between 1 nM (nanomolar) and 1 mM, or from 100 µM (micromolar) to 1 mM, including increments therein, such as 100 µM, 200 µM, 250 µM, 300 µM, 400 µM, 500 µM, 600 µM, 700 µM, 750 µM, 800 µM, 900 µM or 1 mM. The amount of targeted activator and heavy atom-modified malachite green derivative may be the same or different. In one aspect, the targeted activator and heavy atom-modified malachite green derivative are combined prior to administration to the patient or contacting with cells.

When administering to cells in vitro, the targeting activator is added to the culture, and then is optionally washed from the cells by any method. The heavy atom-modified malachite green derivative is then added to the culture and also is optionally washed from the cells by any method. The cells are then exposed to light within the excitation spectrum of the bound heavy atom-modified malachite green derivative, at an intensity and for a duration effective to kill the targeted cells, preferably with minimal impact on non-targeted cells. The timing of each addition, duration of contact between the cells and the administered compositions, and of the exposure to a source of the light is such that efficacy of the method is retained and can vary greatly.

When administering to a patient, the compositions are provided in a pharmaceutically-acceptable carrier or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms for delivery of drug products include: intravenous, intramuscular, or intraperitoneal solutions, oral tablets or liquids, topical ointments or creams and transdermal devices (e.g., patches). Although virtually any delivery route may prove useful for the compounds and compositions described herein, parenteral delivery is contemplated. In one embodiment, the compound is a sterile solution comprising the active ingredient (that is, the targeted activator and heavy atom-modified malachite green derivative), and a solvent, such as water, saline, lactated Ringer's solution, or phosphate-buffered saline (PBS). Additional excipients, such as polyethylene glycol, emulsifiers, salts and buffers may be included in the solution. In one embodiment, the composition is an injectable solution or gel, which is injected at a site in which cell targeting is desired, such as at the site of a tumor.

The heavy atom-modified malachite green derivative, may be provided as pharmaceutically acceptable salts. Pharmaceutically acceptable salts are, because their solubility in water is greater than that of the initial or basic compounds, particularly suitable for medical applications. These salts have a pharmaceutically acceptable anion or cation. In addition, exchange chromatography can be used to change the counterion of the composition. Suitable pharmaceutically acceptable acid addition salts include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine Pharmaceutically acceptable salts may be prepared from the described compounds by any useful method, as are well known in the chemistry and pharmaceutical arts.

The targeted activator and heavy atom-modified malachite green derivative may be administered to a patient once, twice, or multiple times, for example, as is needed to effectively treat the patient. More than one different targeted activators, having different targeting moieties, but the same or different activator moieties, may be administered at the same time or at different times. Using more than one targeted activators with different targeting moieties allows targeting of more than one marker on cells in a patient, thereby increasing efficacy and decreasing the ability of cancer cells to evade treatment. A benefit of the present therapy is that a large number of different targeting activators may be produced, with different targeting moieties targeting different determinants on the same or a different marker of/on a target cell. As such, a variety of progressions of or combination of targeting activators may be available for different therapies.

As indicated above, in one aspect, the targeting activator is first administered to a patient, followed by administration of the heavy atom-modified malachite green derivative to the patient. In another aspect, the targeted activator and heavy atom-modified malachite green derivative are pre-combined before administration to a patient.

According to another aspect of the invention, a "kit" is provided. A kit comprises packaging suitable for, for example: using, storing, and distributing elements of a kit. Packaging includes boxes (e.g., plastic, metal, and/or cardboard, etc.), containers, pouches (e.g., plastic, paper, and/or foil/Mylar), tubes, etc. Elements of the kit can be in any form. Chemical compounds, such as the targeting activator and/or the heavy atom-modified malachite green derivative can be shipped in liquid, dry, lyophilized, crystalline, glassified, or any suitable form. Chemical compounds of the kit are typically distributed in a vessel, which is any suitable container for shipping, storing and optionally using the compound, such as a bottle, flask, vial, test tube, microcentrifuge tube, medical/dosing syringe, intravenous (IV) bag, etc.

A targeted activator is a divalent binding composition comprising an activator moiety (activator) capable of binding the malachite green derivative such that when the malachite green derivative is bound by the targeted activator and illuminated with light within the excitatory spectrum for the derivative, wavelength, an ROS, namely singlet oxygen, is produced. The targeted activator also comprises a targeting moiety for binding to a target, such as a compound or marker characteristic of a cancerous cell; a viral, bacterial, fungal, or parasite antigen; a receptor; a cell-bound immunoglobulin, a cluster of differentiation (CD) marker/antigen, etc. Both the activator, and the targeting moiety may be any type of binding reagent, such as, without limitation, antibodies (polyclonal or monoclonal), antibody fragments, antibody mimetics such as affibodies, affilins, affimers, affitins, alphabodies, anticalins, avimers, DARPins, fynomers, monobodies, nucleic acid ligands (e.g., aptamers), engineered proteins, antigens, epitopes, haptens, or any target-specific binding reagent. Further, in one aspect, the targeted activator is a single fusion protein, comprising both the activator moiety and the targeting moiety, as shown in the examples below, combining the scFv FAP with the targeting affibody in a single fusion protein. Alternately, the activator moiety may be linked to the targeting moiety by any effective chemistry, or even by affinity.

In one embodiment, the activator moiety is an scFv fragment, such as an L5-MG scFv fragment of one of SEQ ID NOS: 1-4 (collectively, L5-MG scFv peptides, see, FIG. 2A), or tandem or multiple repeats thereof, and optionally further comprising an amino acid sequence of the targeting moiety (also referred to as a selectivity component). Other scFv fragments are shown in FIG. 2B (SEQ ID NOS: 5-7). Tandem or multiple iterations of the activator and, when present, the targeting moiety may be either directly linked via a peptide bond, or may comprise an intervening linker between the repeats which does not substantially impact the binding and activating function of the activator and, when present, the targeting moiety. Examples of suitable linkers are short peptide sequences encoded contiguously with the activator and, optionally, the targeting moiety, such as G4S (GGGGS, SEQ ID NO: 16). In another embodiment, the activator comprises a single-chain antibody, and in another, the activator comprises an engineered combination of linked antibody heavy and/or light chain components comprising an antibody antigen binding site (paratope).

In one aspect, the activator moiety is covalently attached to the targeting moiety. The activator can be covalently attached to the targeting moiety using any of a variety of standard techniques. For example, the activator may be directly attached to the targeting moiety by forming a chemical bond between one or more reactive groups on the two molecules. For example, a thiol reactive group on the activator is attached to a cysteine residue (or other thiol containing molecule) on the targeting moiety. Alternatively, the activator moiety may be attached to the targeting moiety via an amino group on the targeting moiety. In another embodiment, the activator and targeting moiety are presented on a contiguous fusion protein. In other embodiments, the activator is attached to the targeting moiety via a linker group. Suitable linkers include, for example, chemical groups, an amino acid or chain of two or more amino acids, a nucleotide or chain of two or more polynucleotides, polymer chains, and polysaccharides. In one example, the activator is attached to the targeting moiety using a linker having a maleimide moiety. Linkers may be, for example, homofunctional (containing reactive groups of the same type), heterofunctional (containing different reactive groups), or photoreactive (containing groups that become reactive on illumination). A variety of photoreactive groups are known, for example, groups in the nitrene family.

One or more activators may be attached at one or more locations on the targeting moiety. For example, two or more molecules of the same activator may be attached at different locations on a single targeting moiety molecule. Alternatively, two or more different activators may be attached at different locations on a single targeting moiety molecule. For example, 2, 3, 4, 5, 6, 7, 8, 9, 10 or more activators are attached at different sites on the targeting moiety. The one or more activators may be attached to the targeting moiety so as to maintain the activity of the activators and the targeting moiety. In certain embodiments, the activator further comprises a moiety that is specific for the targeting moiety. For example, the activator may be linked to a hapten, an antibody fragment or other binding reagent, etc. that is specific for the targeting moiety.

In one aspect, the activator is a binding reagent, binding partner, ligand, FAP, or the like that interacts in any manner with the malachite green derivative, such as by binding the malachite green derivative, to cause the malachite green derivative to produce singlet oxygen. Optimally, absent binding of the activator to the malachite green derivative, the malachite green derivative will not produce singlet oxygen, or produce singlet oxygen insubstantially when not bound to the activator. It should be recognized that there may be low-level singlet oxygen production in the absence of binding of the malachite green derivative by the activator, but that background production should be significantly less than the level of production obtained when the malachite green derivative is bound by the activator. Preferably, the "gain" in singlet oxygen production of activator-bound malachite green derivative to non-activator-bound malachite green derivative is at least 10-fold, 100-fold, 1000-fold, 10,000-fold, or even greater. In an optimal embodiment, the malachite green derivative will not produce singlet oxygen unless bound by the activator, or, as is more likely in the real world, will not substantially produce singlet oxygen unless bound by the activator. In practical use, there will be a certain level of background singlet oxygen production, though it is preferably insubstantial.

As described in the examples herein, one non-limiting embodiment of the activator is an FAP (fluorogen activating peptide), a peptide produced by any useful means that binds to the malachite green derivative compound so as to increase the production of singlet oxygen by the derivative at a given excitatory wavelength and intensity. One embodiment of the FAP is an scFv fragment, obtained from a yeast cell surface display library, and which activates the acceptor so that it fluoresces. The use of a yeast display library, and identification of a specific clone that expresses an FAP, permits directed evolution of the specific clone to produce derivatives with more desirable activity in a given malachite green derivative. An example of that is described below in relation to parent scFV L5-MG and evolved derivatives FAPs L5-MG E52D, L5-MG L91S, and L5-MG E52D L91S.

As would be readily evident to those of ordinary skill in the art, there are a multitude of methods for generating suitable activators and targeting moieties. Selection and evolution using yeast display libraries is an effective mechanism for generating useful FAPs, as indicated by the development of scFV L5-MG and evolved derivatives FAPs L5-MG E52D, L5-MG L91S, and L5-MG E52D L91S. Further details regarding preparation of and development of these polypeptides are provided in WO 2008/092041. It should be evident that activators can be peptides, but also can be other molecules, such as nucleic acids and derivatives thereof, such as aptamers. Molecular libraries, such as libraries of small molecules, natural molecules, synthetic molecules, etc., also can readily be screened for activation of the acceptor by simply exposing the malachite green derivative to a compound and determining if the compound can effectively activate the malachite green derivative as described herein. The malachite green derivative may be screened against libraries of random polypeptides, or libraries of binding agents, such as scFv fragments or other antibody fragments. Expression libraries of protein/peptide fragments or aptamers, expressed by bacteria, yeast, phage, etc. can be screened by colony fluorescence, fluorescence-activated cell sorting (FACS) or by affinity to surface-bound malachite green derivative and subsequent amplification of retained phage, cells, etc. The growth, propagation, selection, and mutation of display/expression libraries is well known. Many commercial display/expression libraries are available and use thereof are well within the skill of the ordinary artisan.

International Patent Application Publication No. WO 2008/092041, incorporated herein by reference in its entirety, describes in detail not only the preparation of the L5-MG FAP, but a large number of other methods by which activators (selectivity component as described in that publication) are selected, evaluated and used. In that reference, a yeast cell surface display library of recombinant human scFvs, obtained from Pacific Northwest National Laboratory was obtained and clones were initially sorted by one or more rounds of FACS, isolating cells that activate a desired fluorogen. Later, the FACS-screened cells were further enriched by affinity selection or further cell sorting.

The activator may be any molecule, compound or composition which is capable of selectively interacting with the malachite green derivative to cause the malachite green derivative to produce singlet oxygen. Non-limiting examples of the activator include: polypeptides, nucleic acids (such as oligonucleotides, cDNA molecules or genomic DNA fragments), carbohydrates, or other suitable organic or inorganic molecules.

The targeting moiety binds, interacts with, or duplicates one or more components of a cell or organism. Exemplary target molecules for the targeting moiety include, for example, molecules involved in tissue differentiation and/or growth, cellular communication, cell division, cell motility, cancer cell markers and other cellular functions that take place within or between cells, including regulatory molecules such as growth factors, cytokines, morphogenetic factors, neurotransmitters, and the like. In certain embodiments, target molecules may be bone morphogenic protein, insulin-like growth factor (IGF), and/or members of the hedgehog and Wnt polypeptide families.

The activator and targeting moiety may be part of a bifunctional compound, such as a fusion (chimeric) protein, or a combination of mono-functional components, such as a cross-linked composition in which an activator is linked by a linking group to a targeting moiety. The activator and targeting moiety may be similar chemical entities, as in the case of a bifunctional chimeric protein, two linked scFv fragments or an scFv activator linked to a protein, antibody or other polypeptide. They also may be different chemical entities, as in the case of the activator being a polypeptide, such as an scFv fragment, and the targeting moiety is a nucleic acid, such as an aptamer, a template imprinted material, a metabolite, a lipid, a polysaccharide, a virion, etc.

In certain embodiments, the activator and/or the targeting moiety are an antibody or an antibody fragment. For example, activators may be monoclonal antibodies, or derivatives or analogs thereof, including without limitation: Fv fragments, single chain Fv (scFv) fragments, Fab' fragments, F(ab')$_2$ fragments, single domain antibodies, camelized antibodies and antibody fragments, humanized antibodies and antibody fragments, and multivalent versions of the foregoing; multivalent activators including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule.

In one embodiment, the activator and/or the targeting moiety is an antibody. Preparation of antibodies may be accomplished by any number of well-known methods for generating monoclonal antibodies. These methods typically include the step of immunization of animals, typically mice; with a desired immunogen (e.g., a desired target molecule-or fragment thereof). Once the mice have been immunized, and preferably boosted one or more times with the desired immunogen(s), monoclonal antibody-producing hybridomas may be prepared and screened according to well-known methods (see, for example, Kuby, Janis, IMMUNOLOGY, Third Edition, pp. 131-139, W. H. Freeman & Co. (1997), for a general overview of monoclonal antibody production).

Production of antibodies and other binding reagents have become extremely robust. In vitro methods that combine antibody recognition and phage display techniques allow one to amplify and select antibodies or other binding reagents with very specific binding capabilities. These methods typically are much less cumbersome than preparation of hybridomas by traditional monoclonal antibody preparation methods. Binding epitopes range in size from small organic compounds such as bromo uridine and phosphotyrosine to oligopeptides on the order of 7-9 amino acids in length.

In one aspect, the activator and/or the targeting moiety is an antibody fragment. Selection and preparation of antibody fragments may be accomplished by any number of well-known methods. Phage display, bacterial display, yeast display, mRNA display and ribosomal display methodologies may be utilized to identify and clone desired antibody fragments. Recombinant technology may be used to generate antibody fragment activators that are specific for a desired target molecule, including, for example, Fab fragments, Fvs with an engineered intermolecular disulfide bond to stabilize the $V_H$-VL pair, scFvs, or diabody fragments.

In certain embodiments, the activator comprises a polypeptide sequence having at least about 85%, at least about 90%, at least about 95%, about 96%, about 97%, about 98%, about 99% or about 100% sequence identity to any of the polypeptide sequences of FIG. 2A. Vectors to produce the activator may be prepared as described in WO 08/092041, with the nucleic acid encoding the polypeptide of FIG. 2A or other activator sequences inserted in frame between flanking HA and c-myc epitopes of the pPNL6 plasmid and its homologs (for example, SEQ ID NO: 9 in FIGS. 3A-3E), and used to transfect host cells as described herein and in WO 08/092041.

Production of scFv antibody fragments using display methods, including phage, bacterial, yeast, ribosomal and mRNA display methods can be employed to produce the activator and/or targeting moiety, as described herein. As described below, yeast display methods were used to produce an activator described below. Yeast display methods are described, for example, in Boder, et al. (2000) Proc. Natl. Acad. Sci USA 97:10701-5; Swers, et al. (2004) Nucl. Acids. Res. 32:e36; and Yeast Display scFv Antibody Library User's Manual, Pacific Northwest National Laboratory, Richland, Wash. 99352, Revision Date: MF031112.

Ribosome display also is a useful method for producing the activator and/or the targeting moiety. Ribosome display is a technique used to perform in vitro protein evolution to create proteins that can bind to a desired ligand. The process results in translated proteins that are associated with their mRNA progenitor which is used, as a complex, to bind to an immobilized ligand in a selection step. The mRNA encodes random polypeptides, and the diversity can far exceed that of phage and yeast display systems. The mRNA-protein hybrids that bind well to a ligand are then reverse transcribed to cDNA and their sequence amplified via PCR. The end result is a nucleotide sequence that can be used to create tightly binding proteins. (see, e.g., Hanes J, Plückthun A (1997) *Proc Natl Acad Sci USA* 91:4937-4942; He M, Taussig M J (1997) *Nucleic Acids Res* 25:5132-5134; and In Vitro Protein Expression Guide, PROMEGA (2005), pp-29-33, Chapter 6, Ribosome Display))

Ribosome display either begins with a DNA sequence or naive library of sequences coding for a specific protein. The sequence is transcribed, and then translated in vitro into protein. However, the DNA library coding for a particular library of binding proteins is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. What results is a complex of mRNA, ribosome, and protein which can bind to surface-bound ligand. This complex is stabilized with the lowering of temperature and the addition of cations such as $Mg^{2+}$.

During the subsequent binding, or panning, stages, the ribosome complex is introduced to surface-bound ligand. This can be accomplished several ways, for example using an affinity chromatography column with a resin bed containing ligand, a 96-well plate with immobilized surface-bound ligand, or magnetic beads that have been coated with ligand. The complexes that bind well are immobilized. Subsequent elution of the binders via high salt concentrations, chelating agents, or mobile ligands which complex with the binding motif of the protein allow dissociation of the mRNA. The mRNA can then be reverse transcribed back into cDNA, undergo mutagenesis, and iteratively fed into the process with greater selective pressure to isolate even better binders.

As it is performed entirely in vitro, there are two main advantages of ribosomal display methods over other selection technologies. First, the diversity of the library is not limited by the transformation efficiency of bacterial cells, but only by the number of ribosomes and different mRNA molecules present in the test tube. Second, random mutations can be introduced easily after each selection round, as no library must be transformed after any diversification step. This allows facile directed evolution of binding proteins over several generations.

In certain display methods, such as phage and yeast display, a library of $V_H$ and $V_L$ chains are prepared from mRNA of B-cells either naïve or immunized animals (such as a mouse, rabbit, goat or other animal), or even from polyclonal or monoclonal hybridoma. The mRNA is reverse-transcribed by known methods using either a polyA primer or murine immunoglobulin-specific primer(s), typically specific to sequences adjacent to the desired VH and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In display vectors, the $V_H$-linker-$V_L$ sequence is cloned into a surface protein (e.g., for M13, the surface proteins g3p (pHI) or g8p, most typically g3p). Display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacteria cells is the Recombinant Phage Antibody System (RPAS), commercially available from GE Healthcare, Piscataway, N.J., and the pSKAN Phagemid Display System, commercially available from MoBiTec (Boca Scientific, Boca Raton, Fla.). Phage display systems, their construction and screening methods are described in detail in, among others, U.S. Pat. Nos. 5,702,892, 5,750,373, 5,821,047 and 6,127,132, each of which are incorporated herein by reference in their entirety.

Typically, once a population of clones, such as phage, yeast, bacteria, ribosomes, etc., are produced that display a desired polypeptide, such as an antibody fragment, epitope specific clones are selected by their affinity for the desired immunogen and, optionally, their lack be used for physically separating immunogen-binding clones from non-binding clones. Typically the immunogen is fixed to a surface and the clones are contacted with the surface. Non-binding clones are washed away while binding clones remain bound. Bound clones are eluted and propogated to amplify the selected clones. A number of iterative rounds of affinity selection typically are used, often increasingly higher stringency washes, to amplify immunogen binding clones of increasing affinity. Negative selection techniques also may be used to select for lack of binding to a desired target. In that case, un-bound (washed) clones are amplified. In the context of the present invention, fluorescence of bound dyedron can be used as a selectable marker for identifying clones. High throughput methods, such as FACS, may initially be employed to select clones, followed, optionally by detection of fluorescence in plated colonies by fluorescent imaging techniques.

Although it is preferred to use spleen cells and/or B-lymphocytes from animals preimmunized with a desired immunogen as a source of cDNA from which the sequences of the $V_H$ and $V_L$ chains are amplified by RT-PCR, naive (un-immunized with the target immunogen) splenocytes and/or B-cells may be used as a source of cDNA to produce a polyclonal set of VH and $V_L$ chains that are selected in vitro by affinity, typically by the above-described phage display (phagemid) method. When naive B-cells are used, during affinity selection, the washing of the first selection step typically is of very high stringency so as to avoid loss of any single clone that may be present in very low copy number in the polyclonal phage library. By this naive method, B-cells may be obtained from any polyclonal source, B-cell or splenocyte cDNA libraries also are a source of cDNA from which the VH and $V_L$ chains may be amplified. For example, suitable murine and human B-cell, lymphocyte and splenocyte cDNA libraries are commercially available.

The activator and/or the targeting moiety do not have to originate from biological sources, such as from naive or immunized immune cells of animals or humans. The activator and/or the targeting moiety may be screened from a combinatorial library of synthetic peptides. One such method is described in U.S. Pat. No. 5,948,635, incorporated herein by reference, which described the production of phagemid libraries having random amino acid insertions in the pill gene of M13. These phage may be clonally amplified by affinity selection as described above.

Panning in a culture dish or flask is one way to physically separate binding clones from non-binding clones Panning may be carried out in 96 well plates in which desired immunogen structures have been immobilized. Functionalized 96 well plates, typically used as ELISA plates, may be purchased from Pierce of Rockwell, Ill. Other affinity methods for isolating clones having a desired specificity include affixing a target molecule to beads. The beads may be placed in a column and clones may be bound to the column, washed and eluted according to standard procedures. Alternatively, the beads may be magnetic so as to permit magnetic separation of the binding particles from the non-binding particles. The immunogen also may be affixed to a porous membrane or matrix, permitting easy washing and elution of the binding clones.

In certain embodiments, it may be desirable to increase the specificity of the activator for a given target molecule or reporter molecule using a negative selection step in the affinity selection process. For example, activator-displaying clones may be contacted with a surface functionalized with molecules distinct from the target molecule or reporter molecule. Clones are washed from the surface and non-binding clones are grown to clonally expand the population of non-binding clones thereby deselecting clones that are not specific for the desired target molecule. In certain embodiments, random synthetic peptides may be used in the negative selection step. In other embodiments, one or more immunogens having structural similarity to the malachite green derivative may be used in the negative selection step.

In certain embodiments, it may be desirable to mutate the binding region of the activator and/or targeting moiety and select for activators and/or targeting moieties with superior binding characteristics as compared to the un-mutated activator. This may be accomplished by any standard mutagenesis technique, such as by PCR with Taq polymerase under conditions that cause errors. In such a case, the PCR primers could be used to amplify scFv- or binding reagent-encoding sequences of (e.g.) phagemid plasmids under conditions that would cause mutations.

The PCR product may then be cloned into a (e.g.) phagemid vector and screened for the desired specificity, as described above. Mutants may be generated and isolated from a library by screening using, for example, alanine scanning mutagenesis and the like, by linker scanning mutagenesis; by saturation mutagenesis; by PCR mutagenesis; or by random mutagenesis. Linker scanning mutagenesis, particularly in a combinatorial setting, is an attractive method for identifying activators.

In other embodiments, the activators and/or targeting moieties may be modified to make them more resistant to cleavage by proteases. For example, the stability of the activators of the present invention that comprise polypeptides may be increased by substituting one or more of the naturally occurring amino acids in the (L) configuration with D-amino acids. In various embodiments, at least 1%, 5%, 10%, 20%, 50%, 80%, 90% or 100% of the amino acid residues of the activators may be of the D configuration. The switch from L to D amino acids neutralizes the digestion capabilities of many of the ubiquitous peptidases found in the digestive tract. Alternatively, enhanced stability of the activators of the invention may be achieved by the introduction of modifications of the traditional peptide linkages. For example, the-introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of the activators may be achieved by intercalating one or more dextrorotatory amino acids (such as, dextrorotatory phenylalanine or dextrorotatory tryptophan) between the amino acids of the activator, hi exemplary embodiments, such modifications increase the protease resistance of the activators without affecting their activity or specificity of interaction with a desired target molecule or reporter molecule.

In certain embodiments, the antibodies or variants thereof, may be modified to make them less immunogenic if and when administered to a subject. For example, if the subject is human, the antibody may be "humanized"; where the complementarity determining region(s) of the hybridoma-derived antibody has been transplanted into a human monoclonal antibody, for example as described in U.S. Pat. No. 6,407,213. Also, transgenic mice, or other mammals, may be used to express humanized antibodies. Such humanization may be partial or complete.

In another embodiment, the activator is a Fab fragment. Fab antibody fragments may be obtained by proteolysis of an immunoglobulin molecule using the protease papain. Papain digestion yields two identical antigen-binding fragments, termed "Fab fragments", each with a single antigen-binding site, and a residual "Fc fragment". In still another embodiment, the activator is a F(ab')2 fragment. $F(ab')_2$ antibody fragments may be prepared from IgG molecules using limited proteolysis with the enzyme pepsin.

In still other embodiments, the activator may be an aptamer, also known as a nucleic acid ligand. Aptamers are oligonucleotides that are selected to bind specifically to a desired molecular structure. Aptamers typically are the products of an affinity selection process similar to the affinity selection of phage display (also known as in vitro molecular evolution). The process involves performing several tandem iterations of affinity separation, e.g., using a solid support to which the desired immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids and phosphorothioate nucleic acids. Aptamers, may be prepared using the "SELEX" methodology which involves selection of nucleic acid ligands which interact with a target in a desirable manner combined with amplification of those selected nucleic acids. The SELEX process is described in U.S. Pat. Nos. 5,475,096 and 5,270,163 and International Application No. WO 91/19813.

The SELEX process provides a class of products which are nucleic acid molecules, each having a unique sequence, and each of which has the property of binding specifically to a desired target compound or molecule. In various embodiments, target molecules may be, for example, proteins, carbohydrates, peptidoglycans or small molecules. SELEX methodology can also be used to target biological structures, such as cell surfaces or viruses, through specific interaction with a molecule that is an integral part of that biological structure.

The basic SELEX method has been modified to achieve a number of specific objectives. For example, U.S. Pat. No. 5,707,796 describes the use of the SELEX process in conjunction with gel electrophoresis to select nucleic acid molecules with specific structural characteristics, such as bent DNA. U.S. Pat. No. 5,580,737 describes a method for identifying highly specific nucleic acid ligands able to discriminate between closely related molecules, termed CounterSELEX. U.S. Pat. No. 5,567,588 describes a SELEX-based method which achieves highly efficient partitioning between oligonucleotides having high and low affinity for a target molecule. U.S. Pat. Nos. 5,496,938 and 5,683,867 describe methods for obtaining improved nucleic acid ligands after SELEX has been performed.

In certain embodiments, nucleic acid ligands as described herein may comprise modifications that increase their stability, including, for example, modifications that provide increased resistance to degradation by enzymes such as endonucleases and exonucleases, and/or modifications that enhance or mediate the delivery of the nucleic acid ligand (see, e.g., U.S. Pat. Nos. 5,660,985 and 5,637,459). Examples of such modifications include chemical substitutions at the ribose and/or phosphate and/or base positions, hi various embodiments, modifications of the nucleic acid ligands may include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications may also include 3' and 5' modifications such as capping. In exemplary embodiments, the nucleic acid ligands are RNA molecules that are 2'-fluoro (2'-F) modified on the sugar moiety of pyrimidine residues.

The activators and/or targeting moiety may be template imprinted material. Template imprinted materials are structures which have an outer sugar layer and an underlying plasma-deposited layer. The outer sugar layer contains indentations or imprints which are complementary in shape to a desired target molecule or template so as to allow specific interaction between the template-imprinted structure and the target molecule to which it is complementary. Template imprinting can be utilized on the surface of a variety of structures, including, for example, medical prostheses (such as artificial heart valves, artificial limb joints, contact lenses and stents), microchips (preferably silicon-based microchips) and components of diagnostic equipment designed to detect specific microorganisms, such as viruses or bacteria. Template-imprinted materials are discussed in U.S. Pat. No. 6,131,580, which is hereby incorporated by reference in its entirety.

In certain embodiments, an activator may contain a tag or handle which facilitates its isolation, immobilization, identification, or detection and/or which increases its solubility. In various embodiments, the tag may be a polypeptide, a polynucleotide, a carbohydrate, a polymer, or a chemical moiety and combinations or variants thereof. In certain embodiments, exemplary chemical handles, include, for example, glutathione S-transferase (GST); protein A, protein G, calmodulin-binding peptide, thioredoxin, maltose binding protein, HA, myc, poly arginine, poly His, poly His-Asp or FLAG tags. Additional exemplary tags include polypeptides that alter protein localization in vivo, such as signal peptides, type III secretion system-targeting peptides, transcytosis domains, nuclear localization signals, etc.

In another embodiment, an activator and/or targeting moiety may be modified so that its rate of traversing the cellular membrane is increased. For example, the activator may be attached to a peptide which promotes "transcytosis," e.g., uptake of a polypeptide by cells. The peptide may be a portion of the HIV transactivator (TAT) protein, such as the fragment corresponding to residues 37-62 or 48-60 of TAT, portions which have been observed to be rapidly taken up by a cell in vitro (Green and Loewenstein, (1989) Cell 55:1179-1188). Alternatively, the internalizing peptide may be derived from the Drosophila antennapedia protein, or homologs thereof. The 60 amino acid long homeodomain of the homeo-protein antennapedia has been demonstrated to translocate through biological membranes and can facilitate the translocation of heterologous polypeptides to which it-is coupled. Thus, activators may be fused to a peptide consisting of about amino acids 42-58 of Drosophila antennapedia or shorter fragments for transcytosis (Derossi et al. (1996) and J Biol Chem 271:18188-18193). The transcytosis polypeptide may also be a non-naturally-occurring membrane-translocating sequence (MTS), such as the peptide sequences disclosed in U.S. Pat. No. 6,248,558.

In one aspect, the activator/targeting moiety is bivalent, comprising both the activator and targeting moiety in one contiguous polypeptide sequence in the form of a fusion (chimeric) protein comprising any suitable polypeptide activator and targeting moiety. As above, the fusion protein may comprise at least one domain which increases its solubility and/or facilitates its purification, identification, detection, targeting and/or delivery. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, and targeting moieties, i.e. proteins specific for a target molecule, etc. In various embodiments, a polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. Linker sequences between an activator and/or targeting moiety polypeptide may be included in order to facilitate construction of the fusion protein or to optimize protein expression or structural constraints of the fusion protein. Exemplary, proof of concept fusion proteins are described below.

Generally, nucleic acid encoding activators and targeting moieties can be introduced into a host cell, such as by transfection or infection, and the host cell is cultured under conditions allowing expression of the activator. Methods of introducing nucleic acids into prokaryotic and eukaryotic cells are well known in the art. Suitable media for mammalian and prokaryotic host cell culture are well known in the art. In some instances, the nucleic acid encoding the subject polypeptide is under the control of an inducible promoter, which is induced once the host cells comprising the nucleic acid have divided a certain number of times. For example, where a nucleic acid is under the control of a beta-galactose operator and repressor, isopropyl beta-D-thiogalactopyranoside (IPTG) is added to the culture when the bacterial host cells have attained a density of about $OD_{600}$ 0.45-0.60. The culture is then grown for some more time to give the host cell the time to synthesize the polypeptide. Cultures are then typically frozen and may be stored frozen for some time, prior to isolation and purification of the polypeptide.

According to one aspect of the invention, the targeting moiety is an antibody mimetic—an engineered protein with binding specificity. Engineered protein targeting moietys may be affibodies, affilins, affimers, affitins, alphabodies, anticalins, avimers, DARPins, fynomers, monobodies. In one aspect, the targeting moiety is an affibody. Affibodies are small proteins originally based on the triple-alpha helix Z domain of *S. aureus* protein A. Affibodies are commercially available to many major targets, and are expressed in soluble, stable forms via any number of host cells/expression systems, and are selectable by affinity binding to a target compound, as with other binding reagents, and their binding is altered by altering their primary sequence according to broadly-known methods. Exemplary affibodies include:

```
her2 (Z_HER2:342):
                                      (SEQ ID NO: 17)
VENKFNKEMRNAYWEIALLPNLNNQQKRAFIRSLYDDP

SQSANLLAEAKKLNDAQAPK;

EGFR (Z_EGFR:1907):
                                      (SEQ ID NO: 18)
AEAKYAKEMWAAWEEIRNLPNLTGWQMTAFIAK

LVDDPSQSSELLSEAKKLNDSQAPK
```

Thus, a nucleotide sequence encoding all or part of an activator and targeting moiety may be used to produce a recombinant form of an activators and targeting moiety via microbial or eukaryotic cellular processes. Ligating the sequence into a polynucleotide construct, such as an expression vector, and transforming, infecting, or transfecting into hosts, either eukaryotic (yeast, avian, insect or mammalian) or prokaryotic (bacterial cells), are standard procedures. Similar procedures, or modifications thereof, may be employed to prepare recombinant polypeptides by microbial means or tissue-culture technology in accord with the subject invention.

By "expression" it is meant the overall flow of information from a gene (without limitation, a functional genetic unit for producing a gene product, typically encoded on DNA or RNA, for some viruses, and comprising a transcriptional promoter, and other cis-acting elements, such as response elements and/or enhancers, an expressed sequence that typically encodes a protein (open-reading frame or ORF) or functional/structural RNA, and a polyadenylation sequence), to produce a gene product (typically a protein, optionally post-translationally modified or a functional/structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected of transduced into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene. All nucleotide sequences described herein are provided in a 5'-to-3' direction and all amino acid sequences described herein are provided in an N-terminal-to-C-terminal direction.

Other embodiments of nucleic acid sequences encoding the activator and targeting moiety, as well as vectors, host cells, cultures thereof, and methods of making fusion proteins are described below or in WO 2008/092041. A nucleic acid encoding an activator and/or targeting moiety can be operably linked to a bacterial promoter, e.g., the anaerobic *E. coli*, NirB promoter or the *E. coli* lipoprotein lip; *Salmonella* pagC promoter, *Shigella* ent promoter, the tet promoter of Tn10, or the ctx promoter of *Vibrio cholera*. Any other promoter can be used. The bacterial promoter can be a constitutive promoter or an inducible promoter. A signal peptide sequence may be added to the construct, such that the activator is secreted from cells. Such signal peptides are well known in the art. In one embodiment, the phage T5 promoter that is recognized by *E. coli* RNA polymerase is used together with a lac operator repression module to provide tightly regulated, high level expression or recombinant proteins in *E. coli*. In this system, protein expression is blocked in the presence of high levels of lac repressor. A huge variety of methods and genetic constructs are available commercially and are otherwise known by or available to those of ordinary skill in the art, for production of recombinant proteins and polypeptides. In vitro protein synthesis using, e.g., eukaryotic lysates, such as rabbit reticulocyte lysates, rabbit oocyte lysates, human cell lysates, insect cell lysates and wheat germ extracts or even synthetic methods, as are broadly known, can be employed to produce the polypeptides described herein.

Plant expression vectors can be used. For example, viral promoters such as the 35S RNA and 19S RNA promoters of CaMV, or the coat protein promoter of TMV may be used; alternatively, plant promoters such as the small subunit of RUBISCO; or heat shock promoters, e.g., soybean hsp 17.5-E or hsp 17.3-B may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology., Academic Press, New York, Section VIII, pp. 421-463; and Grierson & Corey, 1988, Plant Molecular Biology, 2d Ed., Blackie, London, Ch. 7-9. Alternately, insect systems can be employed to produce the polypeptides described herein. In one such system, Autographa californica nuclear polyhedrosis virus (AcNPV) is used as a vector to express foreign genes. The virus grows in *Spodoptera frugiperda* cells. In another embodiment of an insect system, the DNA encoding the subject polypeptide is cloned into the pBlueBacIII recombinant transfer vector (Invitrogen, San Diego, Calif.) downstream of the polyhedrin promoter and transfected into Sf9 insect cells (derived from *S. frugiperda* ovarian cells, available from Invitrogen, San Diego, Calif.) to generate recombinant virus. In another embodiment, the subject polypeptides are prepared in transgenic animals, such that in certain embodiments, the polypeptide is secreted, e.g., in the milk of a female animal.

Viral vectors, useful for introducing genetic material into a cell, are broadly known in the relevant arts, many of which are available commercially, may also be used for efficient in vitro introduction of a nucleic acid into a cell. Infection of cells with a viral vector has the advantage that a large proportion of the targeted cells can receive the nucleic acid. Additionally, polypeptides encoded by genetic material in the viral vector, e.g., by a nucleic acid contained in the viral vector, are expressed efficiently in cells that have taken up viral vector nucleic acid. Examples of useful viral vector systems include retrovirus, adenovirus and adeno-associated virus vectors are generally understood to be useful for the transfer of exogenous genes in vivo, particularly into mammals. These vectors provide efficient delivery of genes into cells, and the transferred nucleic acids typically are stably integrated into the chromosomal DNA of the host (see Miller, A. D. (1990) Blood 76:271).

Another viral gene delivery system utilizes adenovirus-derived vectors. Suitable adenoviral vectors derived from the adenovirus strain Ad type 5 d1324 or other strains of adenovirus (e.g., Ad2, Ad3, Ad7, etc.) are well known to those skilled in the art. Recombinant adenoviruses can be advantageous in certain circumstances in that they are capable of infecting non-dividing cells and can be used to infect a wide variety of cell types, including airway epithelium, endothelial cells, hepatocytes and muscle cells. Furthermore, the virus particle is relatively stable and amenable to purification and concentration, and, as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors. Most replication-defective adenoviral vectors currently in use and therefore favored by the present invention are deleted for all or parts of the viral E1 and E3 genes but retain as much as 80% of the adenoviral genetic material. Expression of the inserted genetic material can be under control of, for example, the EIA promoter, the major late promoter (MLP) and associated leader sequences, the E3 promoter, or exogenously added promoter sequences.

Yet another viral vector system useful for delivery of genetic material encoding the subject polypeptides is the adeno-associated virus (AAV). Adeno-associated virus is a naturally occurring defective virus that requires another virus, such as an adenovirus or a herpes virus, as a helper virus for efficient replication and a productive life cycle. It is also one of the few viruses that may integrate its DNA into non-dividing cells, and exhibits a high frequency of stable integration. Vectors comprising as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470 and Flotte et al. (1993) *J. Biol. Chem.* 268:3781-3790). Other viral vector systems may be derived from herpes virus, vaccinia virus, and several RNA viruses.

In addition to viral transfer methods, such as those illustrated above, non-viral methods can also be employed to cause expression of nucleic acids encoding the subject polypeptides, e.g. in a cell in vitro or in the tissue of an animal Most non-viral methods of gene transfer rely on normal mechanisms used by mammalian cells for the uptake and intracellular transport of macromolecules. Non-viral gene delivery systems may rely on endocytic pathways for the uptake of genetic material by the targeted cell. Exemplary gene delivery systems of this type include liposomal derived systems, polylysine conjugates, and artificial viral envelopes. For example, genetic material can be entrapped in liposomes bearing positive charges on their surface (e.g., lipofectins) and, optionally, which are tagged with antibodies against cell surface antigens of the target tissue (Mizuno et al. (1992) No Shinkei Geka 20:547-551; PCT publication WO 91/06309; Japanese patent application 1047381; and European patent publication EP-A-43075). For example, lipofection of papilloma-infected cells can be carried out using liposomes tagged with monoclonal antibodies against PV-associated antigen (see Viae et al. (1978) J Invest Dermatol 70:263-266; see also Mizuno et al. (1992) Neurol. Med. Chir. 32:873-876).

For example, the gene delivery system comprises an antibody or cell surface ligand which is cross-linked with a gene binding agent such as polylysine (see, for example, PCT publication WO93/04701). For example, genetic material can be used to transfect cells in vivo using a soluble polynucleotide carrier comprising an asialoglycoprotein conjugated to a polycation, e.g., polylysine (see U.S. Pat. No. 5,166,320). It will also be appreciated that effective delivery of the nucleic acid constructs via mediated endocytosis can be improved using agents which enhance escape of the gene from the endosomal structures. For instance, whole adenovirus or fusogenic peptides of the influenza HA gene product can be used as part of the delivery system to induce efficient disruption of DNA-comprising endosomes (Mulligan et al. (1993) Science 260-926; Wagner et al. (1992) Proc. Natl. Acad. ScL USA 89:7934; and Christiano et al. (1993) Proc. Natl. Acad. Sci. USA 90:2122).

EXAMPLES

MG/dL5 fluoromodule as one of the reported fluorogen-FAP complexes has a picomolar affinity and thousands-fold activation of fluorescence upon binding (Szent-Gyorgyi, C., et al. Fluorogen-activating single-chain antibodies for imaging cell surface proteins. *Nat Biotechnol.* 26, 235-240 (2008)). With rational design, fluorogen derivatives binding to FAP have revealed distinct applications in single molecule imaging (Saurabh, S., et al., *Multiplexed Modular Genetic Targeting of Quantum Dots*. ACS Nano, 2014), receptor tracking through pH sensitivity (Grover, A., et al. Genetically Encoded pH Sensor for Tracking Surface Proteins through Endocytosis. *Angew. Chem. Int. Ed.* 51, 4838-4842 (2012)) and protein detection as recombinant affinity probes (Saunders, M. J., et al., A Bifunctional Converter: Fluorescein Quenching scFv/Fluorogen Activating Protein for Photostability and Improved Signal to Noise in Fluorescence Experiments. *Bioconjug Chem,* 2014 and Gallo, E., et al., Fluorogen-activating scFv biosensors target surface markers on live cells via streptavidin or single-chain avidin. *Mol Biotechnol,* 2014. 56(7): 585-90).

The 3, 5-diiodo-4-hydroxybenzaldehyde, anthracene-9, 10-dipropionic acid disodium salt ADPA, were purchased from VWR international and Sigma-Aldrich, tetrasulfonated aluminum phthalocyanine AlPcS4 from frontier scientific, PEG-catalase, PEG-SOD, hoechst dye 33342, live/dead cell viability/cytotoxicity kit L-3224 and dihydroethidium (hydroethidine) D11347 were from Molecular Probes. Basic media was from Invitrogen. H NMR and C NMR data are recorded from Bruker Avance™ 300 MHz and 500 MHz. Mass spectra are obtained from Thermo-Fisher LCQ ESI/APCI Ion Trap. Final products are purified by silica, neutral alumina and reverse-phase chromatography, purity were tested by UPLC. Raw absorbance values of respective free dyes and dye-FAP complex were measured on a PerkinElmer Lambda45 spectrophotometer. Fluorogenic enhancement was measured in 96 well microplates on a Tecan Safire2 reader. Quantum yields were determined by comparing integrated spectra of MG2I-dL5 complexes with Cy5 in PBS7.4 on a Quantamaster monochromator fluorimeter (Photon Technology International).

Cell culture: HEK, A431 and SKBR3 cells (ATCC) were cultured in DMEM (Thermo Fisher) supplemented with 10% fetal bovine serum (FisherBrand). To construct cell lines expressing FAP in different cellular compartment, HEK cells were transfected with pcDNA plasmid using Lipofactamine 2000 (Invitrogen). The transfected cells were selected by G418 for two weeks and then sorted into clone for stable cell line. In pcDNA, L5 was cloned to PGFR-derived transmembrane domain for membrane surface localization, to nuclear localization signal for nucleus targeting and COX signal for mitochondrial labeling.

Determination of singlet oxygen quantum yield: PBS 7.4 solution contains 0.1 mM ADPA and optically matched samples are illuminated from a 660 nm LED source, at different time point, its fluorescence decrease at 374/402 nm was recorded, the data was then fitted into a linear plot, the $\psi_\Delta$ was then calculated from the slopes using the equation below.

$$-\frac{d[A]}{dt} = I_{ab}\Phi_{1O_2}\frac{k_r}{k_d}[A]$$

Dead/Live cell viability assay: 400 nM dye (MG/MG-2I) was pre-complex with cells for 30 mins. After illumination, the buffer was replaced with 2 µM calcein AM and 4 µM EthD-1 working solution. After 30 min incubation at room temperature, the two-color fluorescence cell viability test was conducted with the cells.

Cell killing experiment and cell death count: MG/MG2I was added to the cells 30 minutes before illumination (for A431 and SKBR3 cells, affibody conjugated FAP was added 1 hour prior to illumination). Microscope and light box are used as illumination source, different light dose are achieved by changing of light intensity or illumination time. For death cell counting, the medium was replaced with PBS containing 1 uM propidium iodide and 8 uM Hoechst right after illumination. After 30 min incubation, cells were counted and the death cell ratio is determined by the ratio of PI to Hoechst.

Dihydroethidium: In the presence of $O_2$, DHE is oxidized to 2-Hydroethidium (EOH) and intermediate products which bind to DNA giving rise to a fluorescent signal. The EOH fluorescence is measured at an excitation and emission wavelength of 488 and 567 nm, respectively. Cells were exposed to 2 µM dihydroethidium in 10 minutes prior to illumination.

Figure 4:
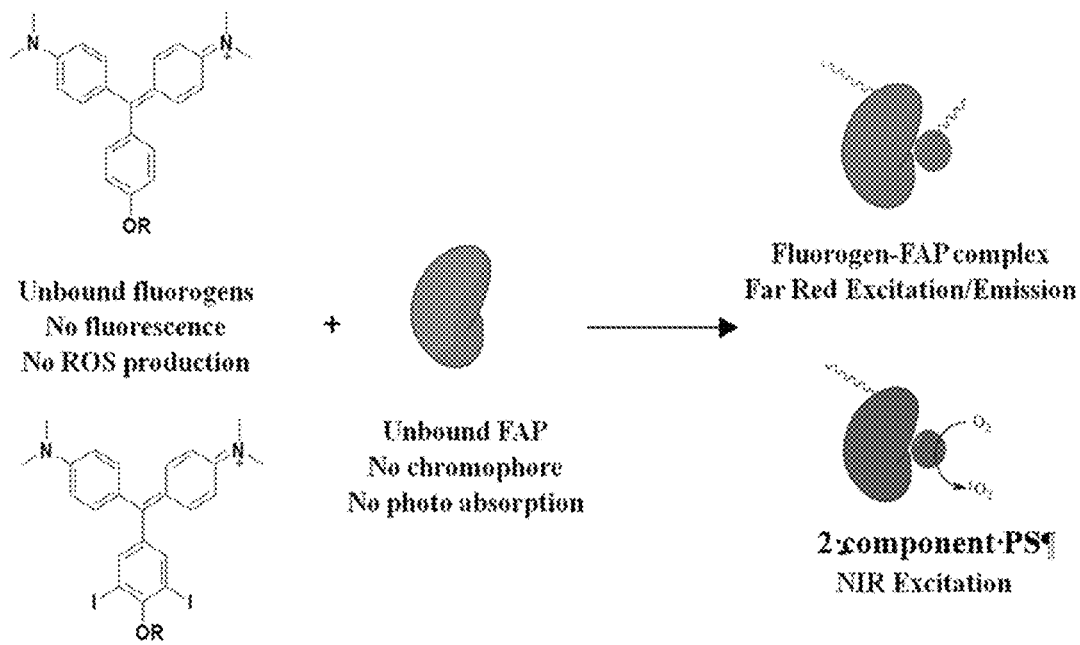
FIG. 4 shows the chemical structure of MG and MG2I ester, and the mechanism of the two-component photosensitizer described in the present invention.
Figure 5:
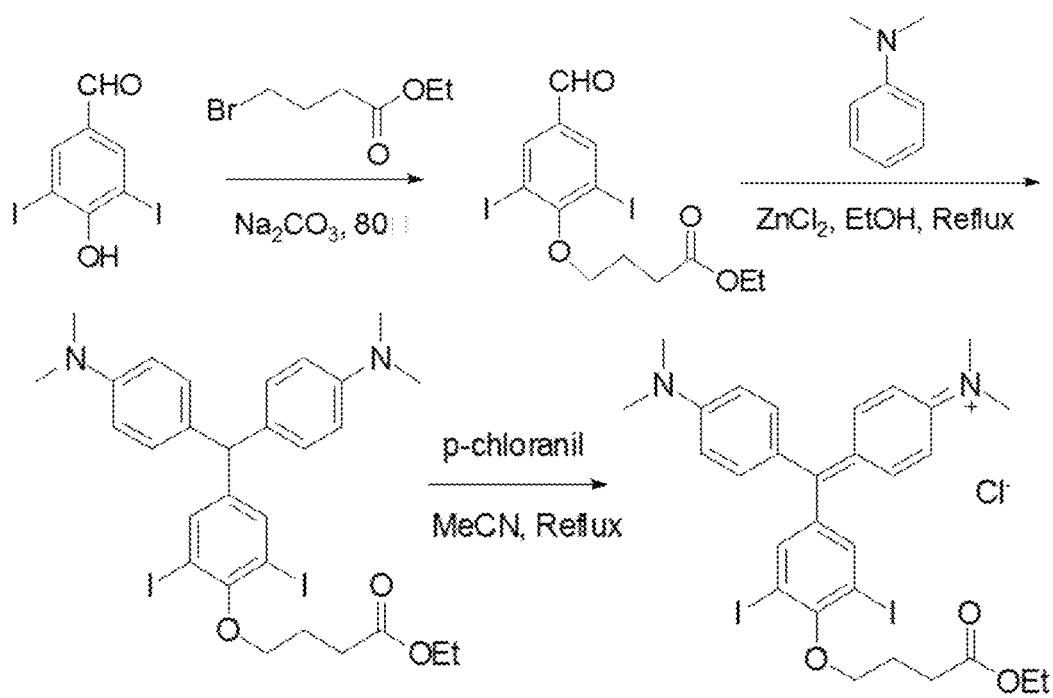
FIG. 5 depicts Scheme I, a method of Synthesis of MG2I, as described in the Examples.

Synthesis of MG2I: The approach herein was to design novel modifications to fluorogens which can greatly increase the triplet state lifetime of the molecules and thus create a ROS activatable photosensitizer. In one example, Methylium, bis[4-(dimethylamino)phenyl](4-(3-carboethoxypropyl)-3,5-diiodo-phenyl)-chloride (MG2I, FIG. 4), a derivative from MG ester, was synthesized as shown in Scheme 1 (FIG. 5).

(1) from Scheme 1: 10 mmol 3, 5-Diiodo-4-hydroxybenzaldehyde was dissolved in dry 5 ml DMF, added 1.1 eq of finely powdered $K_2CO_3$ and heated to 80° C. for 3 hours, the reaction mixture was cooled to room temperature and filtered the precipitate, The solvent was then removed under reduced pressure to afford the crude product, which was purified by column chromatography on silica gel using hexane/Ethyl acetate (4/1), yield: 94%. $^1$H NMR (300 MHz, CDCl$_3$): δ 9.82; (s, 1H), 8.38; (s, 2H), 4.17; (q, 2H), 4.11; (t, 2H), 2.72; (t, 2H), 2.58; (m, 2H), 1.29; (t, 3H), $^{13}$C NMR (100 MHz, CDCl$_3$): δ 188.1, 173.3, 162.7, 141.6, 135.4, 91.7, 72.4, 60.4, 80.6, 25.3, 14.4, MS (EI): m/z (%): 488.2.

5 mmol of Ethyl 4-(2,6-diiodo-4-formylphenoxy)butanoate and 10 mmol N,N-dimethylaniline were dissolved in 50 ml dry EtOH, 5 mmol $ZnCl_2$ were added to the solution, it was heated to reflux for 2 days. After the reaction is finished, the reaction mixture was dried under reduced pressure, purified with silica gel (Eluent: Ethyl acetate/Hexane: 1/1), yield: 65%. $^1$H NMR (300 MHz, CDCl$_3$): δ 7.55; (s, 2H), 6.96; (d, 4H), 6.69; (d, 4H), 5.25; (s, 1H), 4.19; (q, 2H), 4.03; (t, 2H), 2.96; (s, 12H), 2.71; (t, 2H), 2.26; (m, 2H), 1.3; (t, 2H), $^{13}$C NMR (100 MHz, CDCl$_3$): δ155.6, 149.4, 145.7, 140.7, 131.5, 129.8, 112.8, 90.7, 71.9, 60.5, 53.7, 40.9, 31.2, 25.5, 14.4, MS (EI): m/z (%): 712.3.

1 mmol MG[H]-2I ester was dissolved in MeCN and heated to reflux, 1.1 mmol p-chloranil was dissolved in hot MeCN and added to the reaction, it was allowed to further reflux for 2-3 hours. The reaction mixture was dried under reduced pressure, purified with silica gel (Eluent: CHCl$_3$: MeOH (4:1)), yield: 90%. $^1$H NMR (300 MHz, CDCl$_3$): δ

7.68; (s, 2H), 7.35; (d, 4H), 7.02; (d, 4H), 4.17; (m, 4H) 3.41; (s, 12H), 2.7; (t, 2H), 2.26; (m, 2H), 1.28; (t, 3H), $^{13}$C NMR (100 MHz, CDCl$_3$): δ 174.2, 171.7, 161.3, 157.2, 145, 140.6, 138.9, 128, 114.4, 91.3, 72.8, 61.6, 41.5, 30.9, 25.5, 14.6, MS (EI): m/z (%): 710.3.

Figure 6:
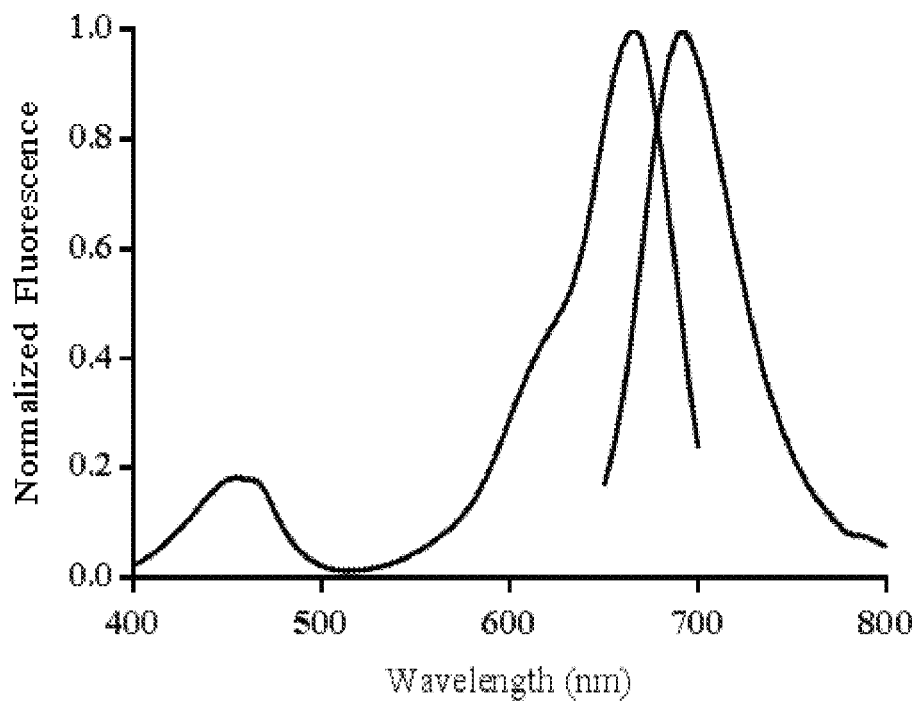
FIG. 6 shows normalized fluorescence spectrum of the MG2I-FAP complex.
Figure 7A:
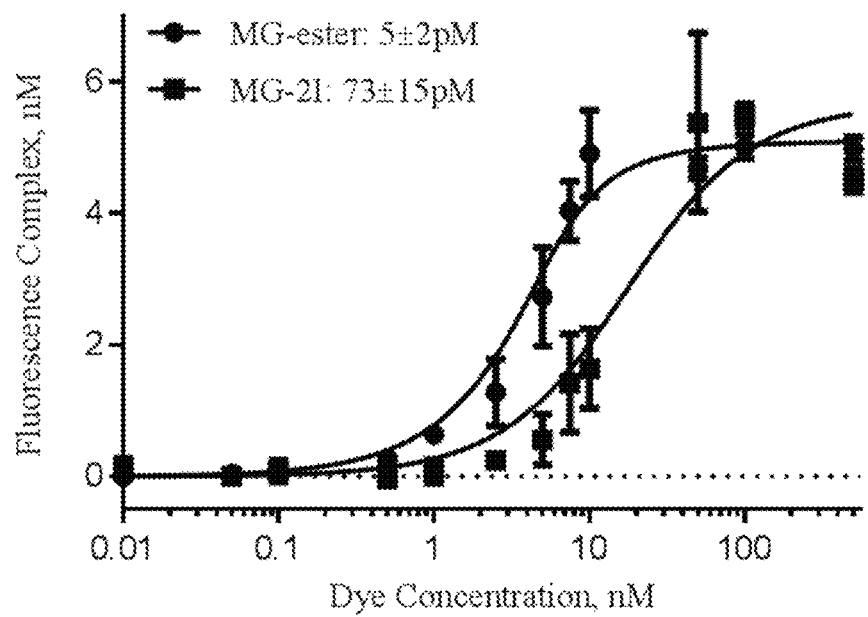
FIGS. 7A-7C.
Figure 7B:
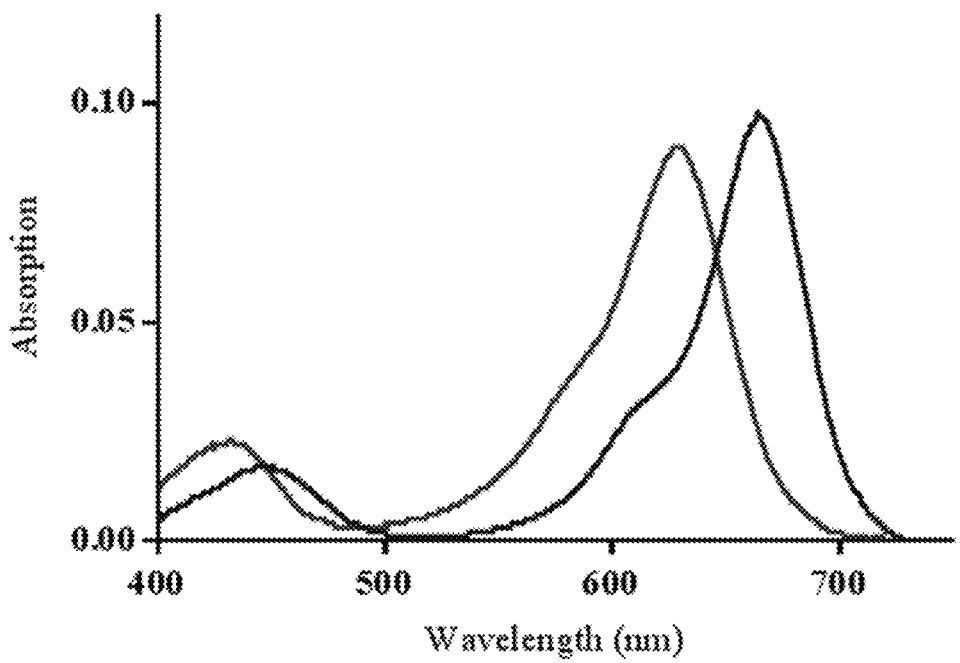
Figure 7C:
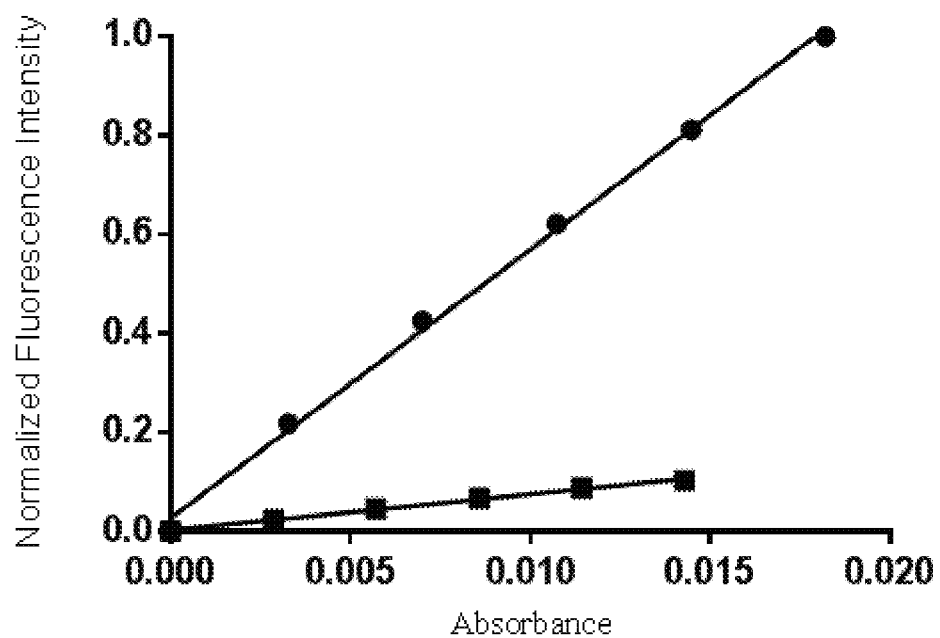

It is noted that heavy-atom substitutions, which are known to increase the spin-orbit coupling for efficient intersystem crossing, do not abolish FAP-fluorogen interactions and dramatically increase the rate of singlet oxygen generations. The iodination effect produces a 22 nm bathochromic shift of the x band of free MG while maintaining the FAP-fluorogen interactions. The iodination also renders the excitation maximum of MG2I-dL5 to 666 nm (compare to MG-dL5 at 633 nm), into the near infrared range (Table 1). The normalized fluorescence spectrum of the MG2I-FAP complex is provided in FIG. 6. FIGS. 7A-7C depict (FIG. 7A) K$_D$ measurement of MG-dL5 and MG2I-dL5, (FIG. 7B) absorption spectra of 1 μM MG2I and MG2I with 5 μM dL5 (shorter wavelength absorption peak), and (FIG. 7C) fluorescence quantum yield measurement of MG2I-dL5 (squares) using Cy5 as standard (circles).

Utilizing the concept, a series of halogenated malachite green derivatives can be made (examples include Br and I with directed FAP selection. Potential FAPs can be found that bind with these derivatives to form similar patterns with equivalent or better photosensitivity.

TABLE 3

Properties of FAP-Fluorogen

| Fluorogen | $\lambda_{Abs}$ (nm) (Fluorogen) | $\lambda_{ex}$ (nm) | $\lambda_{em}$ (nm) | K$_D$ (pM) | ε (10$^4$ M$^{-1}$cm$^{-1}$) | Φ$_F$ | Φ$_\Delta$ |
|---|---|---|---|---|---|---|---|
| MG | 606 | 633 | 668 | 5 | 10.3(9.18) | 0.123 | <0.005 |
| MG2I | 628 | 666 | 693 | 73 | 10.1(9.02) | 0.037 | 0.13 |

Figure 8:
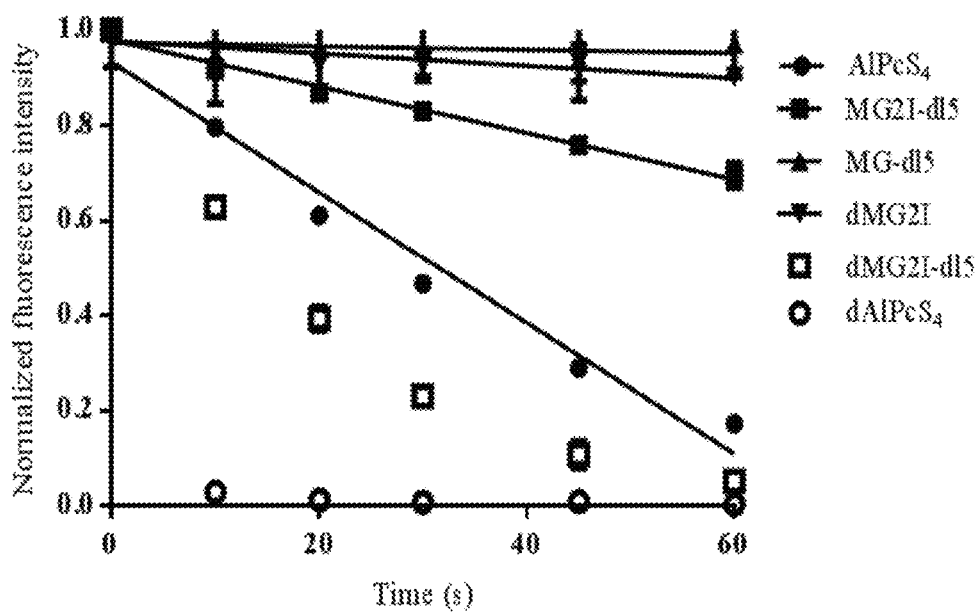
FIG. 8 shows singlet oxygen quantum yield measurement of MG2I-FAP complex.

To test the two-component FAP photosensitizer ability to generate singlet oxygen, anthracene-9, 10-dipropionic acid (ADPA), a commonly used singlet oxygen scavenger, was used. This was done by monitoring the fluorescence disappearance of ADPA at 374/402 nm. Aluminum phthalocyanine tetrasulfonate (AlPcS$_4$) was used as the standard for the measurement of $^1$O$_2$ generation ($\psi_\Delta$=0.34). Optically matched solutions of MG2I-dL5 and AlPcS$_4$ at 660 nm are compared and the singlet oxygen quantum yield of the two-component FAP photosensitizer is estimated to be 0.13 (FIG. 8). To further prove the generation of singlet oxygen, D$_2$O was used instead of H$_2$O; D$_2$O is known to greatly increase the lifetime of $^1$O$_2$ (4 μs to 52 μs), and has little effect toward other reactive oxygen species. In deuterated PBS buffer, the bleaching rate of ADPA by two-component FAP photosensitizer increased significantly. This confirmed the specific generation of singlet oxygen from the complex. Importantly, both the fluorescent quantum yield and the singlet oxygen quantum yield of free dyes are not detectable under normal excitation conditions, due to the very short excited state lifetime (<1 photosensitizer). This ensures that free dye is both non-fluorescent and non-photosensitizing, which is a substantial difference compared to other dye-targeting approaches (FIG. 4). Moreover, with near infrared excitation, this genetically encoded complex is accessible for a range of tumors and can also be used as tool for tumor visualization with fair fluorescence.

Figure 9A:
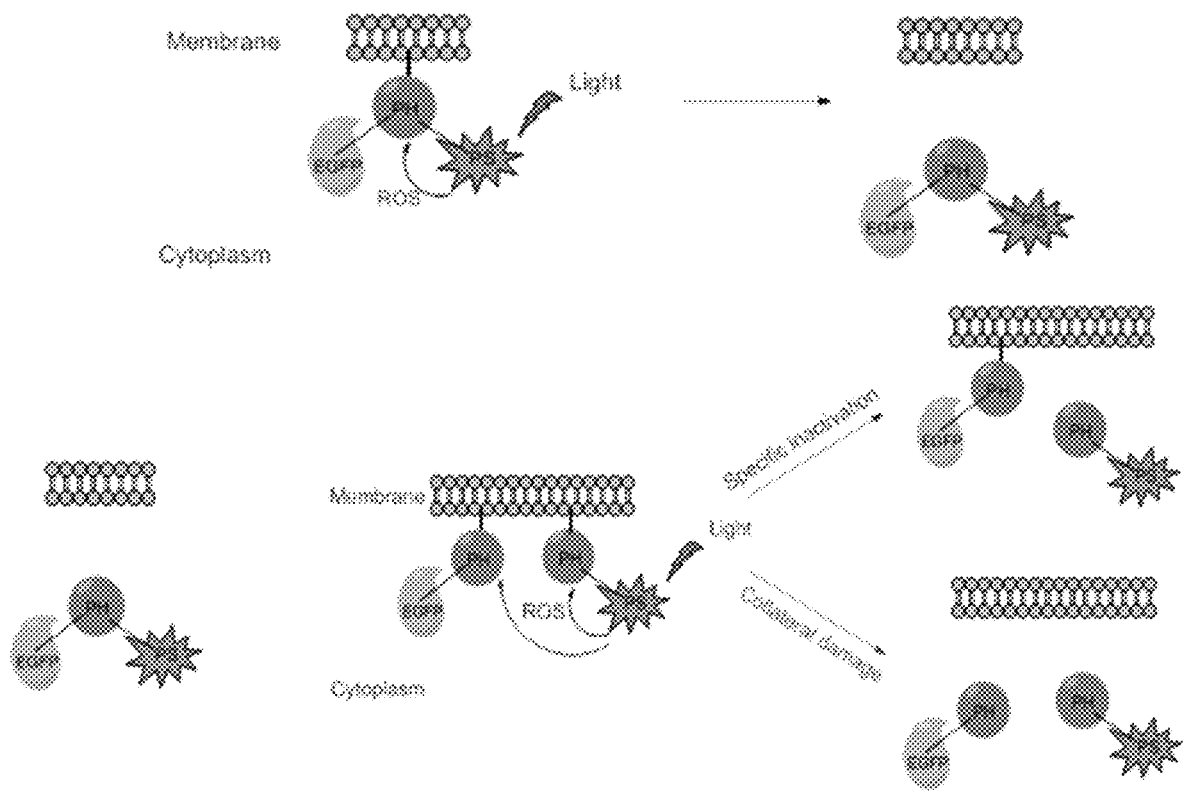
FIGS. 9A and 9B show FAP-TAPs mediated light-induced protein inactivation of the PLC M PH domain.
Figure 9B:
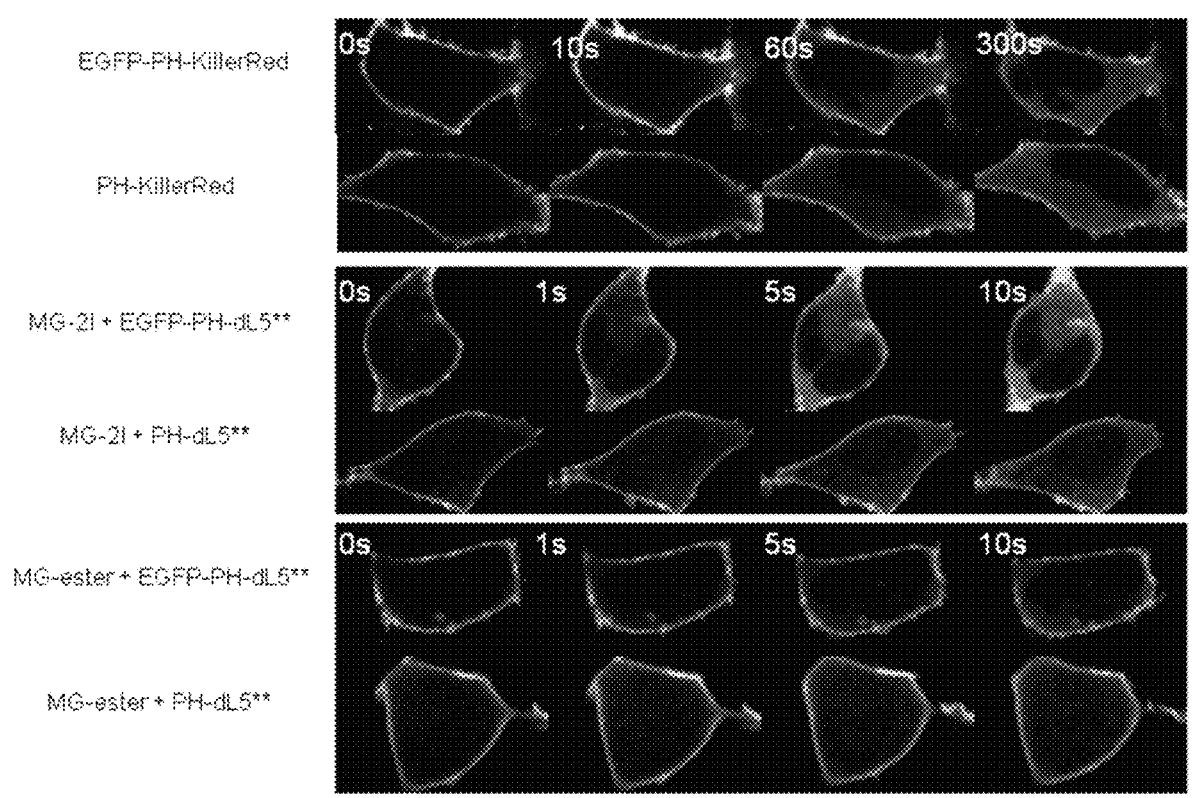

To assess FAP-TAPs utility for targeted protein inactivation, we compared release from the membrane of EGFP-PH-KillerRed and EGFP-PH-dL5 fusion proteins upon suitable illumination in HEK 293 cells. When the pleckstrin homology (PH) domain from PLC δ1 is inactivated by CALI, it translocates from the membrane to the cytoplasm, increasing the cytoplasmic/membrane EGFP signal (FIG. 9A). As shown in FIG. 9B, after 5 min illumination with 560 nm (60× objective, 2.03 W/cm$^2$), the cytoplasm-to-membrane signal ratio changed 37% under KillerRed-mediated CALI, similar to previous reports. The fluorescence of KillerRed is significantly bleached (>75%) after 1 min illumination. In contrast, MG2I-FAP illumination resulted in a 33% ratio change after 10 s of 640 nm laser illumination (60× objective, 2.07 W/cm$^2$). Further illumination of MG2I-FAP induced no EGFP ratio change but noticeable morphology change and minor photobleaching. The potential collateral damage was also assayed by co-expressing EGFP-PH with PH-KillerRed/PH-FAP. Although the timescales of illumination were ~30-fold different, both KillerRed and MG2I-FAP induced similar inactivation of EGFP-PH in proportion to the amount of target inactivation, indicating the MG2I-FAP are spatially restricted similarly to KillerRed under CALI conditions.

Figure 10:
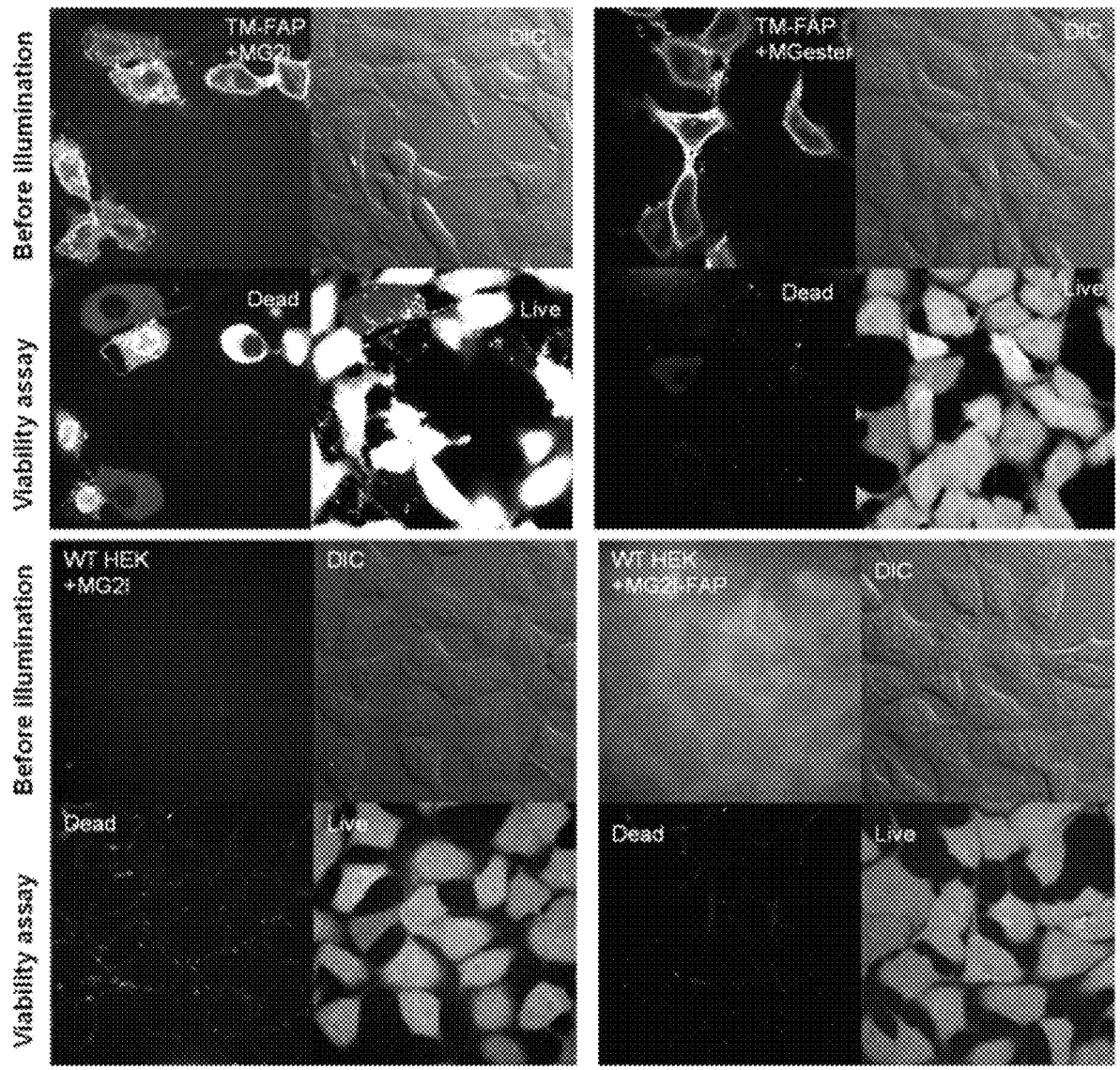
FIG. 10 shows the photosensitization of MG2I with membrane expressed dL5 (40× objective, 42 J/cm$^2$).
Figure 11:
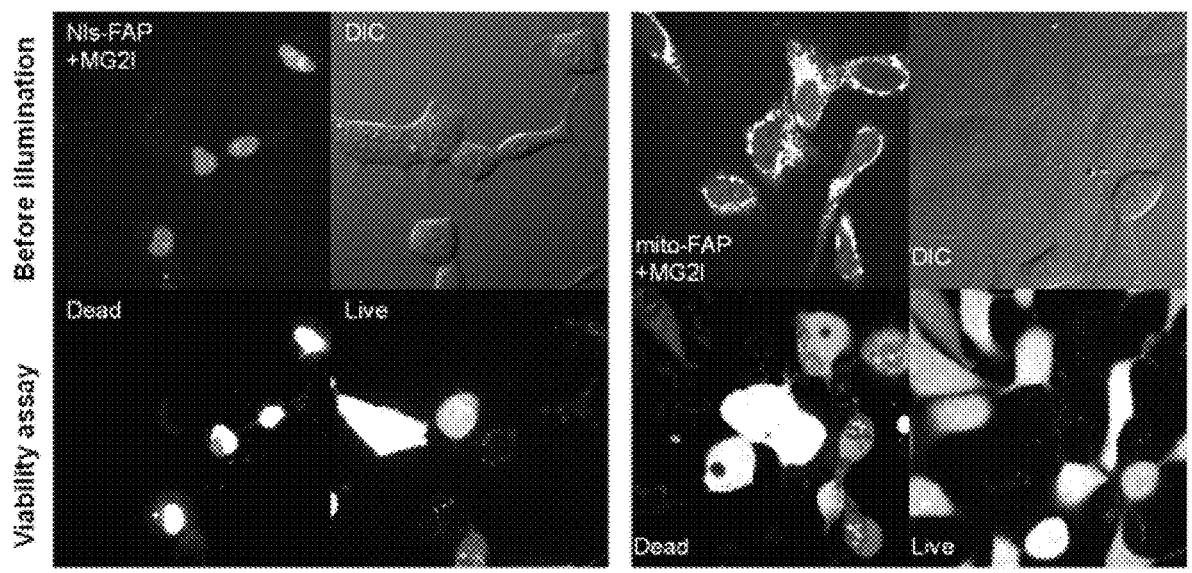
FIG. 11 illustrates the MG2I-FAP complex induced cellular death with FAP expressed in mitochondria (mito-dL5) and nucleus (nls-dL5) (640 nm, 40× objective, 120 J/cm$^2$).

The light induced cytotoxicity of two-component FAP photosensitizer on HEK cells, which were transfected to express FAP on cell surface, was tested. 400 nM MG2I/MG was added to the cell medium 30 minutes prior to illumination; 1 minute of continuous red light illumination from a confocal microscope was applied to cells (40× objective, 640 nm excitation, 0.76 W/cm$^2$). Only labeled cells that were treated with MG2I and exposed to illumination are stained dead within 30 minutes using LIVE/DEAD cell viability kit, while cells that are not labeled remain healthy (FIG. 10). The labeled cells begin to lose cell morphology with swelling and blistering within a very short period. This demonstrated selective killing effect from the two-component FAP photosensitizer. MG-dL5 and MG2I alone with wild-type HEK cells produced no observed light-induced cytotoxicity. Moreover, Non-targeting FAP photosensitizer also has little effect in destroying cells with the same light dose applied. Similar selective killing results were observed for mitochondrial- and nuclear-targeted FAP-transfected HEK cells (FIG. 11).

Figure 12:
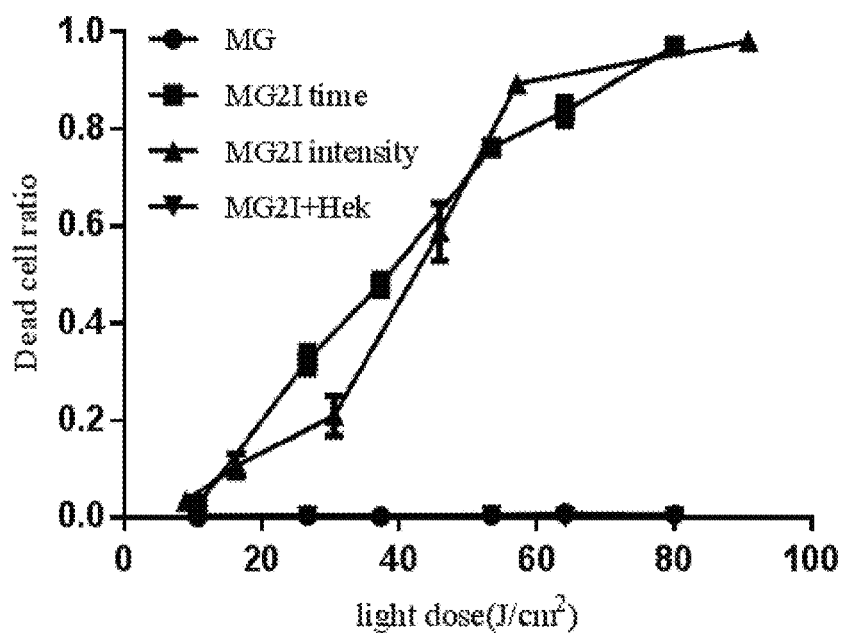
FIG. 12 shows dose dependent killing effect of membrane targeted MG2I-FAP.

Photosensitization of the MG2I-dL5 complex does not result in dramatic self-bleaching, allowing high-dose delivery and real time evaluation of drug uptake and efficacy of therapy. A light box was built with light-emitting diodes arrays (LED) that emit light at 660 nm (0.089 W/cm$^2$); the light distribution was examined to be almost homogeneous from a 96-well cy5 bleaching experiment and the temperature in the box stays around 35° C. up to 1 hour illumination. The light dose required to kill half of the cells using microscope or light box are around the same value, 50 J/cm$^2$. A light dose dependent killing effect (change of time or light intensity) was also only observed with cells expressing FAP treating with MG2I exposed under light box (FIG. 12).

While change of time gives a linear-like dose dependent response, change of light intensity implies a more complicated process. Our understanding is that cells have a threshold concentration of singlet oxygen buffering, so, when the amount of singlet oxygen generation exceeds the threshold, extended time with low intensity irradiation is going to destroy the cells as well.

Figure 13:
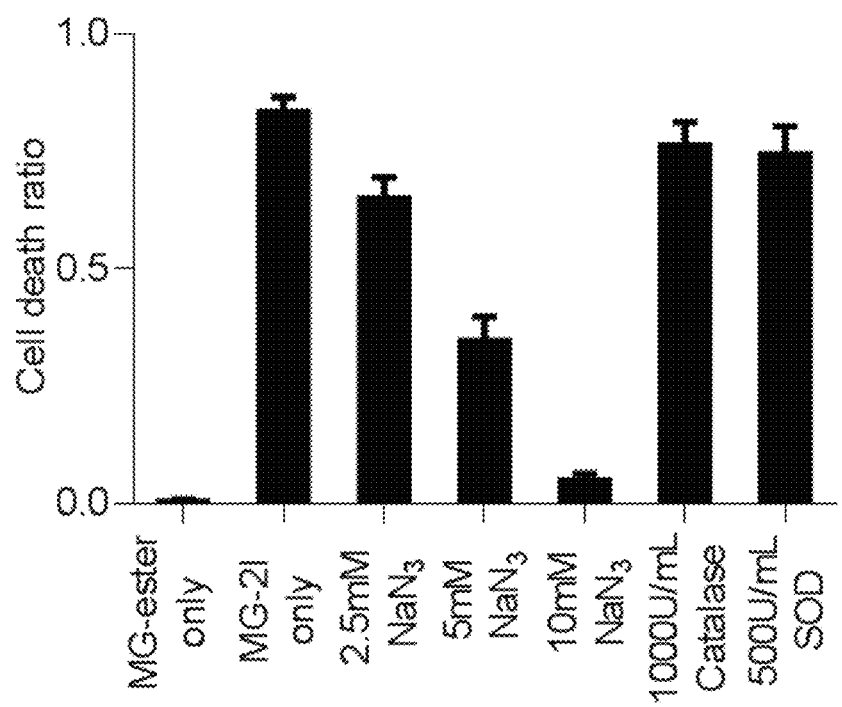
FIG. 13 shows singlet oxygen induced cellular phototoxicity effect that can be inhibited by sodium azide but not catalase nor superoxide dismutase.
Figure 14:
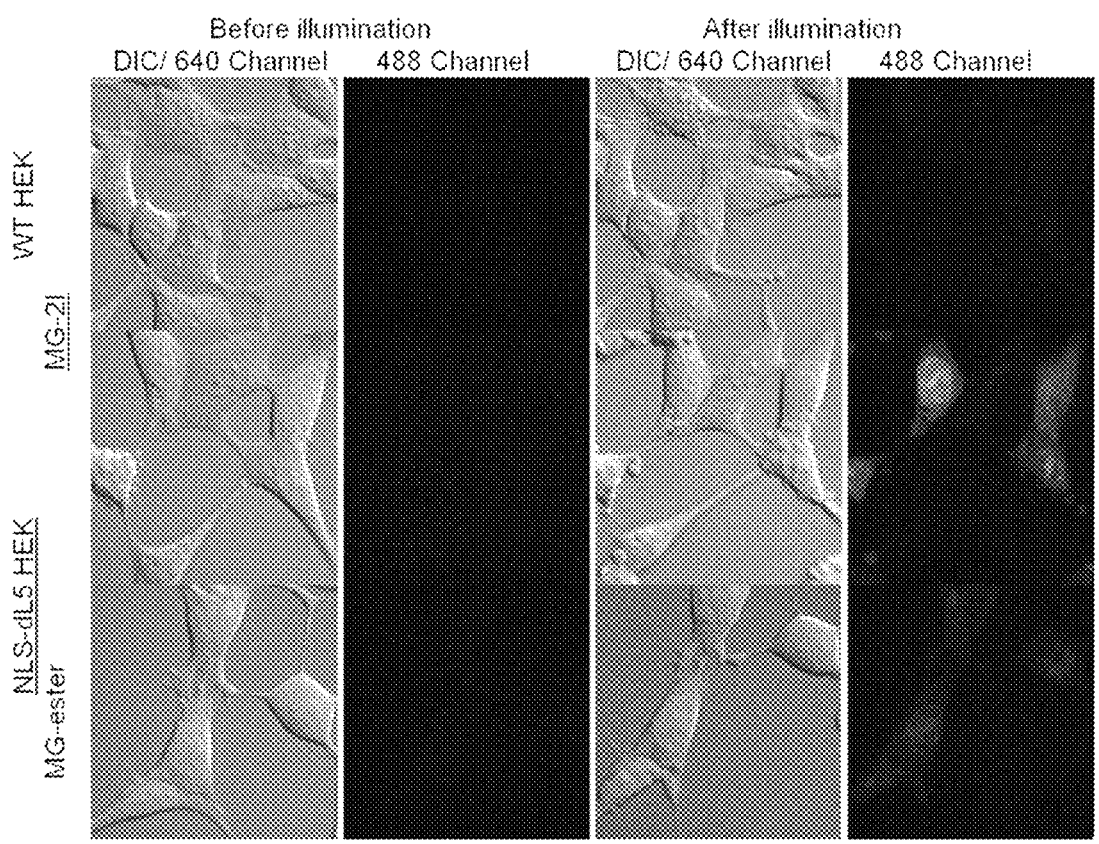
FIG. 14 illustrates nuclear ROS detection using DHE.

The cause of MG2I-dL5 induced cell cytotoxicity was further delineated by adding different ROS quenchers to the solutions. When looking at the effects at microscope scale, sodium azide (NaN$_3$) showed a dose-dependent inhibition of cellular death; at concentrations higher than 10 mM, the cytotoxicity effects in the same time frame were totally inhibited. Meanwhile, catalase up to 1000 U/mL has very little effect in rescuing cell death (FIG. 13). Since sodium azide is known to strongly quench singlet oxygen, catalase and SOD are more of superoxide-specific quenchers, the results suggest singlet oxygen is the dominating ROS that causes cellular toxicity towards cell death. Singlet oxygen is believed to first react with nearby organic molecules, and produce one of the many peroxide species as initial products; these generated precursory ROS will propagate to produce other reactive products, leading to cascade cytotoxicity in a wide physiological range. Hence, different ROS sensors can be used to identify the follow-up generation of ROS after photosensitization of the two-component FAP photosensitizer. Dihydroethidium (DHE) as a ROS sensor was chosen herein using HEK cells that were transfected with dL5 in the nucleus. DHE is cell permeable and can react with $O_2^-$ to form 2-hydroxyethidium, which can intercalate with DNA to provide fluorescence at 520/610 nm. Very specific and clear DHE signal increase has been seen only in MG2I-dL5 labeled cells (FIG. 14).

Two-Component FAP Photosensitizer (AffiFAP) Construction and Expression

Figure 15:
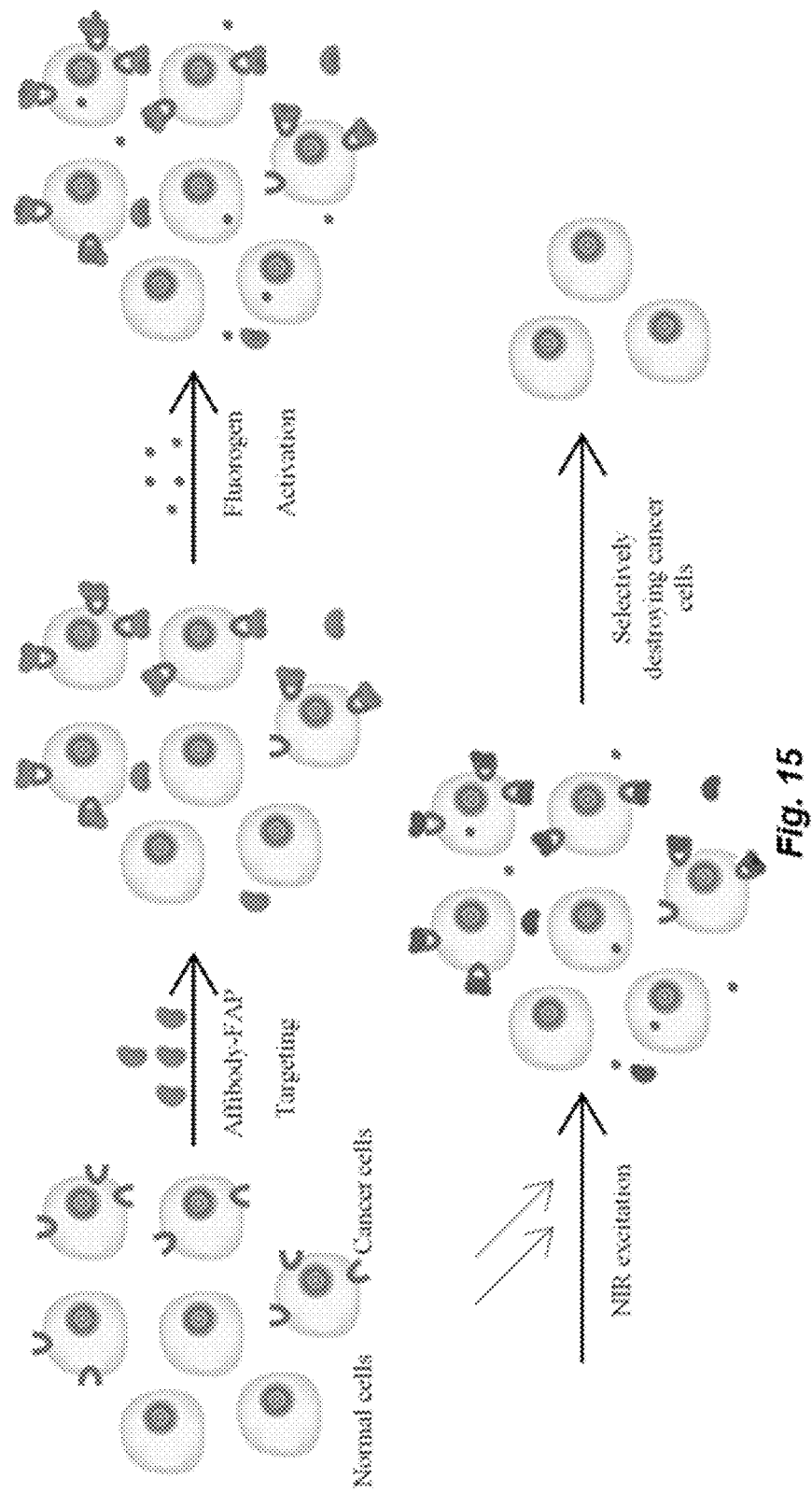
FIG. 15 illustrates the method of the cancer cell targeting activatable photodynamic therapy achievable with the two-component FAP photosensitizer.

The two-component FAP photosensitizer was targeted to cancer cells through FAP-conjugated affibodies to study its phototoxicity towards cancer cells (FIG. 15).

DNA Construction. The *Escherichia coli* (*E. coli*) bacterial strain MACH1-T1 (Invitrogen) was used as the host for cloning. The pET21a vector was modified to include an N-terminal 10×His and GST followed by an HRV3C protease cleavage site. Multiple cloning sites were introduced after the HRV3C protease site in the order of HindIII, NheI, BamHI, SpeI, KpnI, and XhoI from 5' to 3'. Fragments of $FAP_{dL5}$ and affibody $Z_{EGFR:1907}$ were amplified from pPNL6 and pJET1.2, respectively. In construct $Z_{EGFR:1907}$, affibody was inserted into the modified pET21a vector using HindIII and XhoI sites. FAP was inserted between NheI and BamHI sites to make construct $FAP_{dL5:}$. In construct $FAP_{dL5}$-$Z_{EGFR:1907}$, FAP was introduced into the vector between HindIII and NheI sites; affibody was inserted between KpnI and XhoI sites. In constructs $Z_{EGFR:1907}$-$FAP_{dL5}$, FAP and affibody were introduced using KpnI, XhoI, HindIII, and NheI sites. For construct $Z_{EGFR:1907}$-$FAP_{dL5}$-$Z_{EGFR:1907}$, affibody was introduced into $Z_{EGFR:1907}$-$AP_{dL5}$ construct through HindIII and BamHI sites. Affibody constructs of $Z_{HER2:342}$ were built on $Z_{EGFR:1907}$ constructs by replacing affibody fragment. Full sequences for various "AffiFAP" polypeptides are provided in FIGS. 16A and 16B (SEQ ID NOS: 10-15).

Protein Expression and Purification. Expression of recombinant proteins was carried out in the *E. coli* strain Rosetta-gami 2 (DE3) (Novagen). The plasmids were transformed into competent cells and fresh colonies were grown in 5 mL overnights with 12.5 µg/mL tetracycline, 34 µg/mL chloramphenicol, and 50 µg/mL ampicillin. The 5 mL cultures were then added to 500 mL LB+GB (10 g/L tryptone, 5 g/L yeast extract, 4 g/L NaCl with 100 mM phosphate pH 7.2 and supplemented with 20 mM succinic acid, 0.4% glycerol) to an OD of 0.8 at 37° C., the temperature was dropped to 22° C. for 1 h and then cultures were induced with 500 µM IPTG and supplemented with 0.4% glucose for 18 h growth at 22° C. Cells were pelleted and washed once with cold PBS before freezing at −20° C. The pellets were resuspended in 3 mL of wash buffer A (50 mM Tris-Cl pH 7.5, 750 mM NaCl, 0.1% Triton X-100, 0.02% Tween-20, 50 mM imidazole) and sonicated with 10, 15 s pulses prior to dilution with 15 mL of wash buffer A. This lysate was centrifuged 30 min at 20 000 g and the supernatant was incubated with Ni-NTA agarose beads (Thermo Fisher) for 2 h at 4° C. with rocking. After binding, beads were washed with 10 mL of wash buffer A and then put on a column and washed with wash buffer 150 (same as wash buffer A but with 150 mM NaCl). His tagged HRV 3C protease was used to cleave the FAP—affibody away from His-GST at 4° C. overnight and protease was then removed by incubating with additional Ni-NTA beads at 4° C. for 2 h. Protein released by the proteolytic digestion was collected as flowthrough and was then purified on Superdex 75 Gel Filtration Colume (GE Healthcare) by fast protein liquid chromatography (BioLogic DuoFlow, Biorad). Endotoxin was removed from the purified protein by endotoxin removal resin (Thermo Fisher). Purity was evaluated using SDS-PAGE and protein was quantified using a DU730 UV/vis spectrophotometer based on the absorbance at 280 nm (Beckman Coulter Inc.).

In Vitro Studies (A431 Cells)

Figure 17:
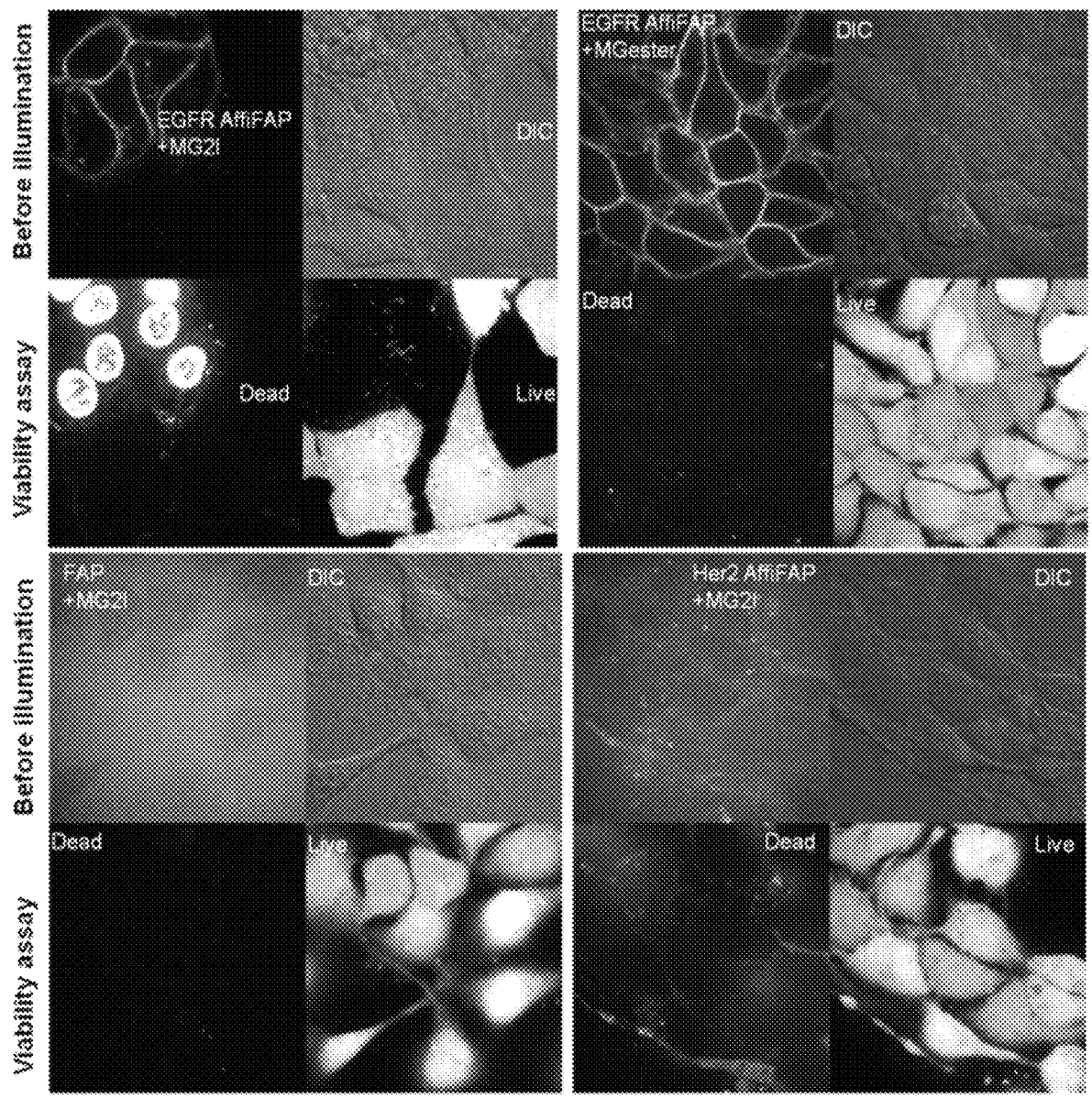
FIG. 17 shows the selective cancer cell killing effect. AffiFAP/FAP was added first and allow cell targeting for 30 minutes, MG2I/MG-ester was then added and incubated for another 30 minutes (No washing is needed in the process). After 1 min illumination (60× objective, 2.43 W/cm$^2$), Dead/Live working solution was used to replace the cell culture medium. Two-color viability fluorescence assay was performed after 1 hr staining

FAP-conjugated HER1 affibody was used to target EGFR over-expressing tumor cells A431 in cell cultures mixed with wild-type HEK cells. 250 nM affiFAP was first added to label A431 cells, followed by 250 nM MG2I/MG. As shown in FIG. 17, neither dye with FAP (no EFGR binding) nor affiFAP with MG caused any significant kill upon illumination; however, when affiFAP and MG2I together were added, and the mixed cells were illuminated, only the EGFR1-expressing tumor cells were killed; adjacent normal HEK cells were unharmed. The results that nonbinding FAP photosensitizer exhibits no obvious toxicity in cells indicate close contact to critical target site is necessary for effective killing; this is because the singlet oxygen has a very short radius of action (<0.02 µm). It is shown that the tumor cells need to be targeted first by the HER1-dL5 affibody, and become accessible to photosentisization only after MG2I is added and bound to the affiFAP. Similar results were seen in FAP conjugated HER2 affibody-labeled SKBR3 cancer cells (FIG. 18). Thus, by controlling the specific generation of singlet oxygen on the tumor site, we can eliminate the nonspecific damage to normal cells. Moreover, the whole process requires no washing and has a fast binding time, while the affibody is reported to have a short clearance time (for example: Affibody-DyLight750 half-life of 37.5±2.8 min). This improvement to the current state-of-the-art photodynamic therapy will be of great utility, for example with the methods and modularity described herein.

Affibody and FAP Arrangement

N and C-terminal fusions were evaluated, as well as a single FAP flanked by two affibodies for their properties to bind and activate MG-fluorogens as well as their binding to target receptors on cultured cells. In the presence of MG, fluorescence scans of all three $Z_{EGFR:1907}$ fusion probes AF, FA and AFA featured a major and a minor excitation peak at 636 nm and 480 nm, and a single emission peak at 664 nm, which are consistent with the fluorescence spectra of F. FA and AFA probes showed an enhanced fluorescence intensity compared to F and AF. Based on the measurement of fluorescence under equilibrium binding conditions, these three probes possessed sub-nanomolar dissociation constants, which were comparable to F alone. A small, but significant decrease in association rate was observed in all FAP-affibody fusion proteins compared to the F only. No detectable fluorescence activation or fluorogen binding by affibody alone were observed. Hence, all fusion proteins preserve the fluorogen activating properties of the unmodified FAP, and the affibody alone does not interfere with fluorogen activation.

TABLE 4

| Recombinant probes | Ex/Em (nm) | Kd (nM) | Kd (nM) Cell surface | $k_{on}$ ($*10^6 M^{-1} S^{-1}$) |
|---|---|---|---|---|
| F | 633/666 | 0.70 ± 0.08 | 4.7 ± 1 | 1.38 |
| AF | 634/664 | 0.43 ± 0.12 | 122 ± 16 | 1.05 |
| FA | 634/664 | 0.28 ± 0.10 | 101 ± 17 | 1.03 |
| AFA | 634/666 | 0.53 ± 0.11 | 37 ± 6 | 1.02 |

Characterization of recombinant probes affibody $Z_{EGFR:1907}$ (A) and $FAP_{dL5**}$ (F) binding to malachite green.

For $FAP/Z_{HER2:342}$ probes, the fluorescence excitation and emission scans were compared to F. The dye-only control showed no detectable fluorescence. The constructs A and AA also showed no significant fluorescence activation of MG. The fusion of affibody to dL5 decreased fluorescence activation by about 25%. A red shift was also observed with the affibody-FAP fusion constructs. In order to test the binding of dye to the fusion proteins, the dissociation constant of probes binding to MG-Btau were measured. Constructs A and AA showed no significant binding of MG upon titrations. The fusion of affibody to dL5 slightly lowered down the affinity of FAP binding to MG, but the dissociation constants of all the constructs were still in the nanomolar range.

The labeling of cell surface EGFR by $Z_{EGFR:1907}$ fusion probes was tested with A431 cells, a cell line that expressed EGFR at high levels, ~2000000/cell. Based on live-cell imaging, three fusion probes AF, FA and AFA all showed clear cell surface labeling, and control protein F failed to target to the cell surface. By equilibrium binding fluorescence, the cell surface dissociation constant was estimated to be 122±16 nM for AF, 101±17 nM for FA and 37±6 nM for AFA.

To validate the $Z_{HER2:342}$ affibody in the fusion probes, cell surface Ka was measured as 8.4±1.6 nM for AF, 25.3±4.7 nM for FA and 6.1±1.8 nM for AFA. The binding specificity of the FAP/affibody fusion was confirmed by a competition assay, where unlabeled A was titrated into constant concentration of AFA.

Animal Studies

We have conducted two animal studies to validate the effectiveness of this method in vivo.

Figure 19:
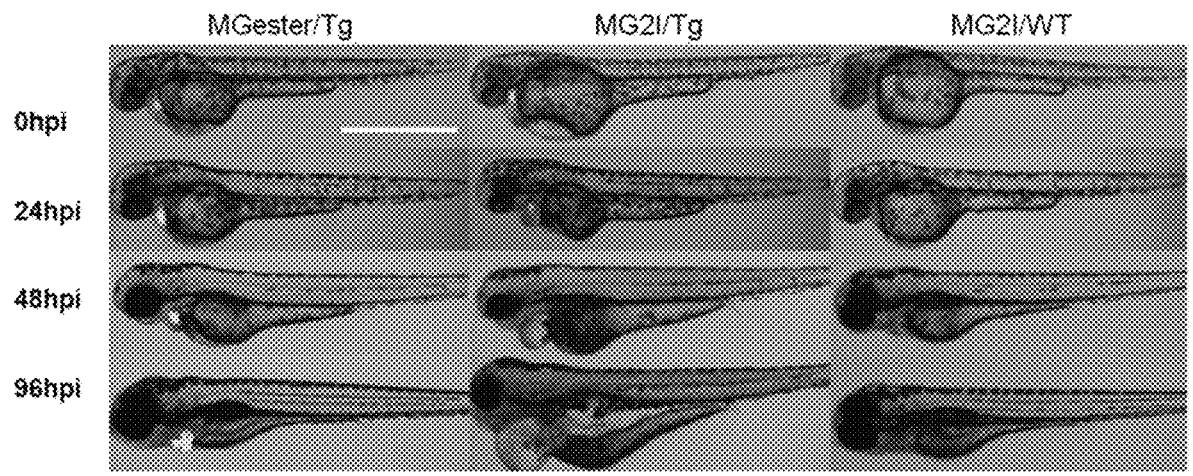
FIG. 19 shows Phenotype development from 0hpi (hour post illumination) to 96 hpi of larval zebrafish. MG2I-FAP induced photo-ablation of cardiac function of transgenic zebrafish. In MG2I-FAP group, the larvae developed a range of visible defects: large cardiac edema, small eyes, and collapsed, nonfunctional heart chambers. In both control groups, development proceeded normally. Scale Bar=1000 µm and applied to all images.

First, transgenic zebrafish lines were produced that expressed a cytoplasmic FAP-mCerulean3 (FAP-mCer3) tandem protein under control of the heart-specific myosin light chain 7 (my17, also known as cmlc2) promoter, Tg(my17: FAP-mCer3). Zebrafish embryos at 48 hour post fertilization (hpf) were treated with 500 nM fluorogen (MG2I or MG-ester) for 3 hours followed by 12 minutes laser illumination (659 nm, 242 mW/cm$^2$) Immediately after illumination, transgenic zebrafish treated with MG2I showed no sign of heart beat or blood circulation, while MG-ester treated transgenic larvae and wild-type zebrafish treated with MG2I were normal (FIG. 19). This indicated that the cytotoxic effects are a result of the optical stimulation of the MG2I-FAP in the expressing cells. FIG. 19 are photomicrographs of zebrafish larvae as described above. White denotes the presence of cytoplasmic FAP-mCerulean3 in live cells.

Figure 20:
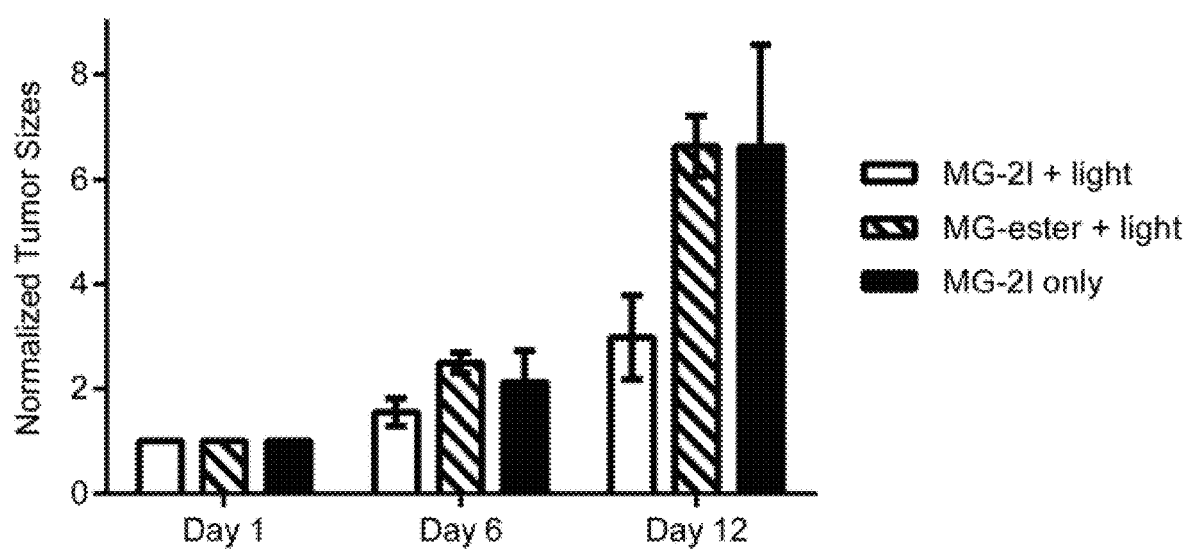
FIG. 20 shows in vivo photodynamic therapy application of MG2I-AffiFAP, which reduce the A431 tumor growth of a nude mice model.

Second, the effectiveness of MG2I-AffiFAP was evaluated by nude mice bearing A431 tumors. MG2I pre-complexed with EGFR AffiFAP was tail-injected to give a final concentration of 500 nM. Three (3) hours after injection, the tumor site of mice was subjected to a 659 nm laser illumination (242 mW/cm$^2$) for 1 hour. Tumor growth was then followed up to 12 days (FIG. 20). The result of this experiment has shown that MG2I-AffiFAP can effectively reduce the tumor growth.

A two-component photosensitizer, which demonstrated robust and selective killing effects for transfected HEK cells and affibody targeted A431 cancer cells both in vitro and in vivo when exposed to near infrared light excitation is described herein. Free MG2I is a pure and stable fluorogen; it is facile to synthesize and modify, and has no toxicity to cells. Unlike conventional photosensitizers, the dye and FAP itself have no photosensitizing effect until they are bound. Different than other activation methods, the activation step is achieved by adding the fluorogen, not the presence of the targeted molecule, so that the leaving of the quenching group can happen; an 'active' activation instead of a 'passive' activation. This method offers the ability to locally "switch on" and selectively generate singlet oxygen at the target site. Importantly, this photosensitizer system can be used for a wide variety of molecular targets.

This invention differs from widely-known methods of photodynamic therapy and general photosensitizer compounds, and has been demonstrated and described in accordance with several examples, which are intended to be illustrative in all aspects rather than restrictive. Thus, the present invention is capable of many variations in detailed implementation, which may be derived from the description contained herein by a person of ordinary skill in the art.

The invention can be further characterized in the following numbered clauses.

Clause 1. A method of targeting and killing cells, comprising:
  a. contacting cells with a targeting activator composition comprising a targeting moiety that selectively binds a target compound of the cell, and an activator moiety that selectively binds a heavy atom-modified malachite green derivative having an excitation wavelength so that the heavy atom-modified malachite green derivative produces singlet oxygen when bound by the targeting activator and exposed to light at the excitation wavelength;
  b. contacting cells with the heavy atom-modified malachite green derivative;
  c. exposing the cells to light at an excitation wavelength of the targeting activator-bound heavy atom-modified malachite green derivative
wherein the heavy atom-modified malachite green derivative has the structure:

(Formula I)

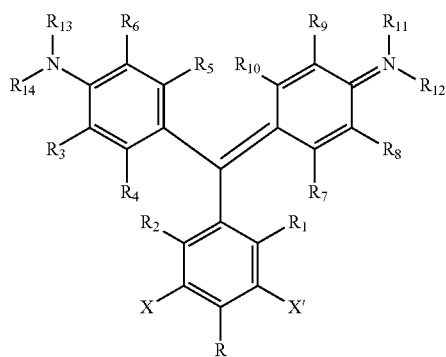

where X and X' are, independently, heavy atoms, R1, R2, R3, R4, R5, R6, R7, R8, R9, and R10 are, independently H or F, R11, R12, R13 and R14 are, independently, methyl, H, aziridine or azetidine, wherein when R11, R12, R13, and/or R14 are aziridine or azetidine, R11 and R12 form a single ring and/or R13 and R14 form a single ring, and where R is selected from —H, —OH, —COO⁻, —SO₃⁻, —PO₄⁻, —NO₂, —NH₂, —N(CH₃)(R15), —OR16, alkyl, ether, polyether, PEG$_{1-30}$, —(C₁-C₄ alkyl)-R17, heterocyles containing N, S or O atoms, substituted acetylenic groups, cyano, and carbohydrate groups, wherein R15 and R16 are: straight- or branched-chain alkyl; straight or branched-chain C$_{1-6}$ alkyl; straight-chain or branched poly(C₁-C₄ alkyl amide); straight-chain or branched poly(C₁-C₄ alkyl amide) having from 2 to 6 amide moieties; poly(C₁-C₄ alkylene glycol); poly(C₁-C₄ alkylene glycol) having from 2 to 30 or from 2-10 C₁-C₄ alkylene glycol moieties; straight-chain or branched poly(C₁-C₄ alkyl amide):poly(C₁-C₄ alkylene glycol) diblock copolymer; straight-chain or branched poly(C₁-C₄ alkyl amide):poly(C₁-C₄ alkylene glycol) diblock copolymer having from 2 to 6 amide moieties and from 2 to 10 C₁-C₄ alkylene glycol moieties; sulfonyl or bis-sulfonyl-terminated straight-chain or branched poly(C₁-C₄ alkyl amide), optionally having from 2 to 6 amide moieties; bis-taurine branched poly(C₁-C₄ alkyl amide), optionally having from 2 to 6 amide moieties; ethyl butyrate; C$_{1-6}$ alkyl C$_{1-6}$ alkanoate; —(CH₂)$_n$—(CH₂)$_n$—C(O)—O—(CH₂)$_m$—CH₃, where n=1-4 and m=0-3, and wherein R17 is selected from H, —OH, —COO⁻, —SO₃⁻, —PO₄⁻, —NO₂, or —NH₂.

Clause 2. The method of claim 1, in which R1, R2, R3, R4, R5, R6, R7, R8, R9, and R10 are H.

Clause 3. The method of clause 1 or 2, in which in which X and X' are independently Br, I, As, Se, Ga, Ge, or Sb.

Clause 4. The method of clause 1 or 2, in which X and X' are independently Br or I.

Clause 5. The method of clause 3, in which X and X' are I.

Clause 6. The method of clauses 1 or 2, in which R11, R12, R13 and R14 are, independently, methyl or H, or R11, R12, R13 and R14 are methyl.

Clause 7. The method of any one of clauses 1-5 in which R is —OR16, and R16 is ethylbutyrate.

Clause 8. The method of clause 1, in which the heavy atom-modified malachite green derivative is:

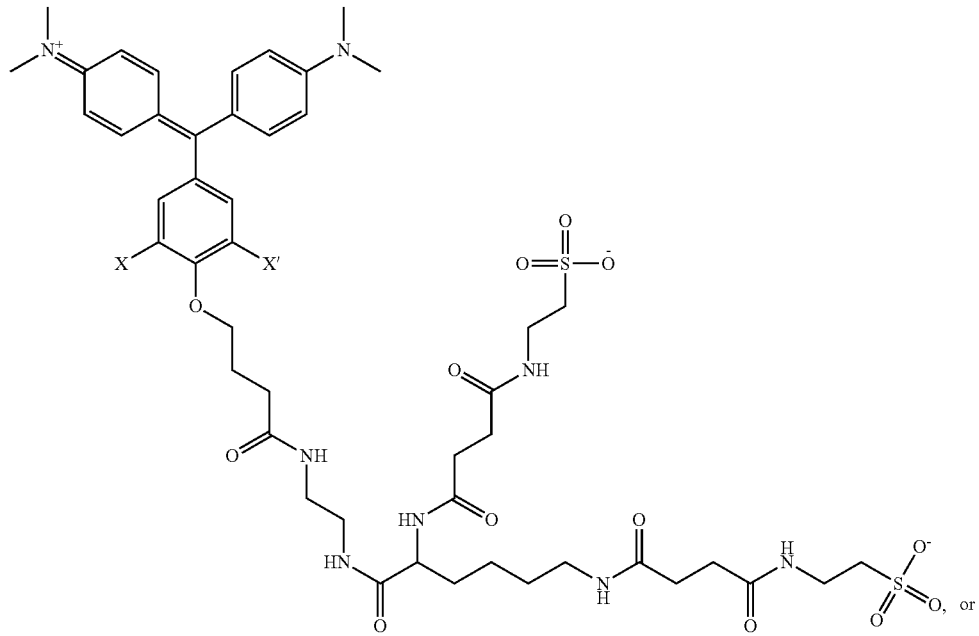

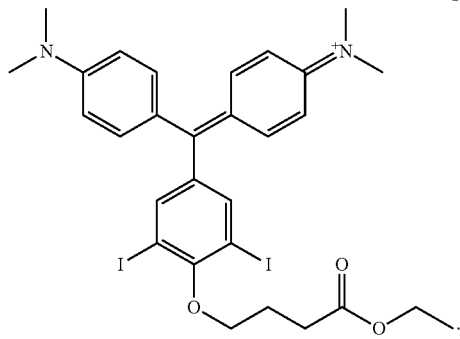

Clause 9. The method of any one of clauses 1-8, in which the activator moiety is fusion protein of an scFv activator moiety and an affibody targeting moiety.

Clause 10. The method of clause 9, in which the scFv is an L5-MG scFv peptide, optionally SEQ ID NOS: 1-4.

Clause 11. The method of any one of clauses 1-10, in which the targeting moiety is selective for an epidermal growth factor receptor.

Clause 12. The method of clause 10, in which the epidermal growth factor receptor is HER1 (human epidermal growth factor receptor 1) or HER2 (human epidermal growth factor receptor 2).

Clause 13. The method of any of clauses 1-12, in which the targeting activator comprises a sequence selected from SEQ ID NOS: 1-4, 10-15, 17 and 18.

Clause 14. A heavy atom-modified malachite green derivative having the structure:

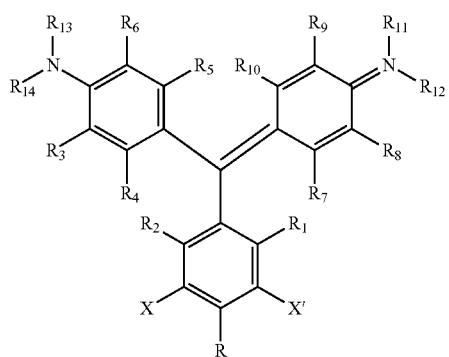

(Formula I)

where X and X' are, independently, heavy atoms, R1, R2, R3, R4, R5, R6, R7, R8, R9, and R10 are, independently H or F, R11, R12, R13 and R14 are, independently, methyl, H, aziridine or azetidine, wherein when R11, R12, R13, and/or R14 are aziridine or azetidine, R11 and R12 form a single ring and/or R13 and R14 form a single ring, and where R is selected from —H, —OH, —COO$^-$, —SO$_3^-$, —PO$_4^-$, —NO$_2$, —NH$_2$, —N(CH$_3$)(R15), —OR16, alkyl, ether, polyether, PEG$_{1-30}$, —(C$_1$-C$_4$ alkyl)-R17, heterocyles containing N, S or O atoms, substituted acetylenic groups, cyano, and carbohydrate groups, wherein R15 and R16 are: straight- or branched-chain alkyl; straight or branched-chain C$_{1-6}$ alkyl; straight-chain or branched poly(C$_1$-C$_4$ alkyl amide); straight-chain or branched poly(C$_1$-C$_4$ alkyl amide) having from 2 to 6 amide moieties; poly(C$_1$-C$_4$ alkylene glycol); poly(C$_1$-C$_4$ alkylene glycol) having from 2 to 30 or from 2-10 C$_1$-C$_4$ alkylene glycol moieties; straight-chain or branched poly(C$_1$-C$_4$ alkyl amide):poly(C$_1$-C$_4$ alkylene glycol) diblock copolymer; straight-chain or branched poly(C$_1$-C$_4$ alkyl amide):poly(C$_1$-C$_4$ alkylene glycol) diblock copolymer having from 2 to 6 amide moieties and from 2 to 10 C$_1$-C$_4$ alkylene glycol moieties; sulfonyl or bis-sulfonyl-terminated straight-chain or branched poly(C$_1$-C$_4$ alkyl amide), optionally having from 2 to 6 amide moieties; bis-taurine branched poly(C$_1$-C$_4$ alkyl amide), optionally having from 2 to 6 amide moieties; ethyl butyrate; C$_{1-6}$ alkyl C$_{1-6}$ alkanoate; —(CH$_2$)$_n$—C(O)—O—(CH$_2$)$_m$—CH$_3$, where n=1-4 and m=0-3, and wherein R17 is selected from H, —OH, —COO$^-$, —SO$_3^-$, —PO$_4^-$, —NO$_2$, or —NH$_2$.

Clause 15. The heavy atom-modified malachite green derivative of clause 14, in which R1, R2, R3, R4, R5, R6, R7, R8, R9, and R10 are H.

Clause 16. The heavy atom-modified malachite green derivative of clause 14 or 15, in which in which X and X' are independently Br, I, As, Se, Ga, Ge, or Sb.

Clause 17. The heavy atom-modified malachite green derivative of clause 14 or 15, in which X and X' are independently Br or I.

Clause 18. The heavy atom-modified malachite green derivative of clause 17, in which X and X' are I.

Clause 19. The heavy atom-modified malachite green derivative of clause 14 or 15, in which R11, R12, R13 and R14 are, independently, methyl or H, or R11, R12, R13 and R14 are methyl.

Clause 20. The heavy atom-modified malachite green derivative of any one of clauses 14-19 in which R is —OR16, and R16 is ethylbutyrate.

Clause 21. The heavy atom-modified malachite green derivative of clause 14, in which the heavy atom-modified malachite green derivative is:

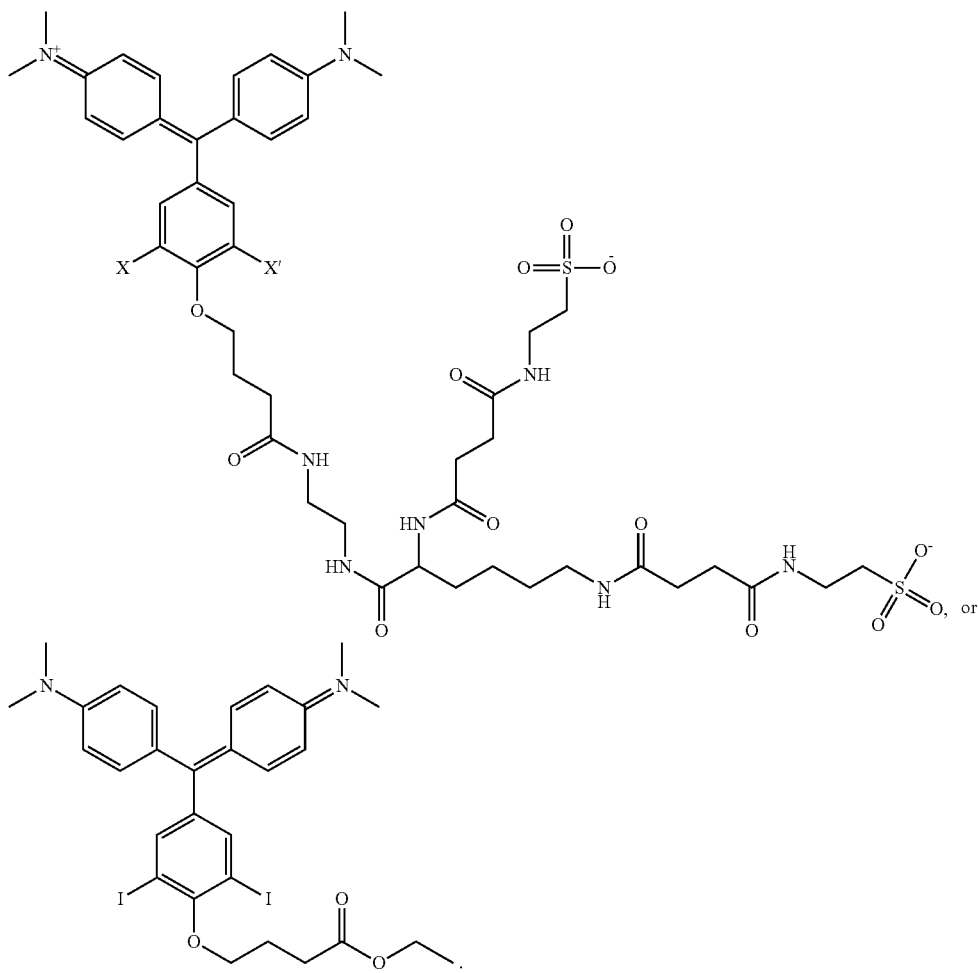

Clause 22. A kit comprising:
a. a first vessel containing the heavy atom-modified malachite green derivative having the structure:

(Formula I)

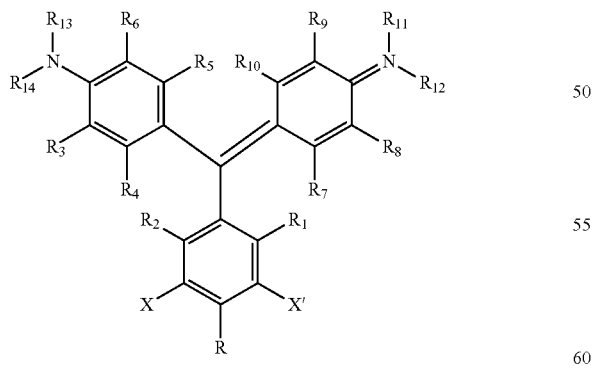

where X and X' are, independently, heavy atoms, R1, R2, R3, R4, R5, R6, R7, R8, R9, and R10 are, independently, H or F, R11, R12, R13 and R14 are, independently, methyl, H, aziridine or azetidine, wherein when R11, R12, R13, and/or R14 are aziridine or azetidine, R11 and R12 form a single ring and/or R13 and R14 form a single ring, and where R is selected from —H, —OH, —COO$^-$, —SO$_3^-$, —PO$_4^-$, —NO$_2$, —NH$_2$, —N(CH$_3$)(R15), —OR16, alkyl, ether, polyether, PEG$_{1-30}$, —(C$_1$-C$_4$ alkyl)-R17, heterocyles containing N, S or O atoms, substituted acetylenic groups, cyano, and carbohydrate groups, wherein R15 and R16 are: straight- or branched-chain alkyl; straight or branched-chain C$_{1-6}$ alkyl; straight-chain or branched poly(C$_1$-C$_4$ alkyl amide); straight-chain or branched poly(C$_1$-C$_4$ alkyl amide) having from 2 to 6 amide moieties; poly(C$_1$-C$_4$ alkylene glycol); poly(C$_1$-C$_4$ alkylene glycol) having from 2 to 30 or from 2-10 C$_1$-C$_4$ alkylene glycol moieties; straight-chain or branched poly(C$_1$-C$_4$ alkyl amide):poly(C$_1$-C$_4$ alkylene glycol) diblock copolymer; straight-chain or branched poly(C$_1$-C$_4$ alkyl amide):poly(C$_1$-C$_4$ alkylene glycol) diblock copolymer having from 2 to 6 amide moieties and from 2 to 10 C$_1$-C$_4$ alkylene glycol moieties; sulfonyl or bis-sulfonyl-terminated straight-chain or branched poly(C$_1$-C$_4$ alkyl amide), optionally having from 2 to 6 amide moieties; bis-taurine branched poly (C$_1$-C$_4$ alkyl amide), optionally having from 2 to 6 amide moieties; ethyl butyrate; C$_{1-6}$ alkyl C$_{1-6}$ alkanoate; —(CH$_2$)$_n$—C(O)—O—(CH$_2$)$_n$—CH$_3$, where n=1-4 and m=0-3, and wherein R17 is selected from H, —OH, —COO$^-$, —SO$_3^-$, —PO$_4^-$, —NO$_2$, or —NH$_2$, in a pharmaceutically-acceptable excipient; and b. a targeting activator composition in the first vessel or in a second vessel containing comprising a targeting moiety that selectively binds a target compound of a cell, and an activator moiety that selectively binds a heavy atom-modified malachite green derivative having an excitation wavelength so that the heavy atom-modified malachite green derivative produces singlet oxygen when bound by the targeting activator and exposed to light at the excitation wavelength in a pharmaceutically-acceptable excipient.

Clause 23. The kit of clause 22, in which R1, R2, R3, R4, R5, R6, R7, R8, R9, and R10 are H.

Clause 24. The kit of clause 22 or 23, in which in which X and X' are independently Br, I, As, Se, Ga, Ge, or Sb.

Clause 25. The kit of clause 22 or 23, in which X and X' are independently Br or I.

Clause 26. The kit of clause 25, in which X and X' are I.

Clause 27. The kit of clause 22 or 23, in which R11, R12, R13 and R14 are, independently, methyl or H, or R11, R12, R13 and R14 are methyl.

Clause 28. The kit of any one of clauses 22-27, in which R is —OR16, and R16 is ethylbutyrate.

Clause 29. The kit of clause 22, in which the heavy atom-modified malachite green derivative is:

Clause 30. The kit of any one of clauses 22-29, in which the activator moiety is fusion protein of an scFv activator moiety and an affibody targeting moiety.

Clause 31. The kit of clause 30, in which the scFv is an L5-MG scFv peptide, optionally SEQ ID NOS: 1-4.

Clause 32. The kit of any one of clauses 22-31, in which the targeting moiety is selective for an epidermal growth factor receptor.

Clause 33. The kit of clause 32, in which the epidermal growth factor receptor is HER1 (human epidermal growth factor receptor 1) or HER2 (human epidermal growth factor receptor 2).

Clause 34. The kit of any of clauses 22-33, in which the targeting activator comprises a sequence selected from SEQ ID NOS: 1-4, 10-15, 17 and 18.

Clause 35. A method of targeting and killing cells in a patient, comprising
a. administering to the patient an effective amount of a targeting activator composition comprising a targeting moiety that selectively binds to targeted cells, and an activator moiety that selectively binds a heavy atom-modified malachite green derivative having an excitation wavelength so that the heavy atom-modified mala-

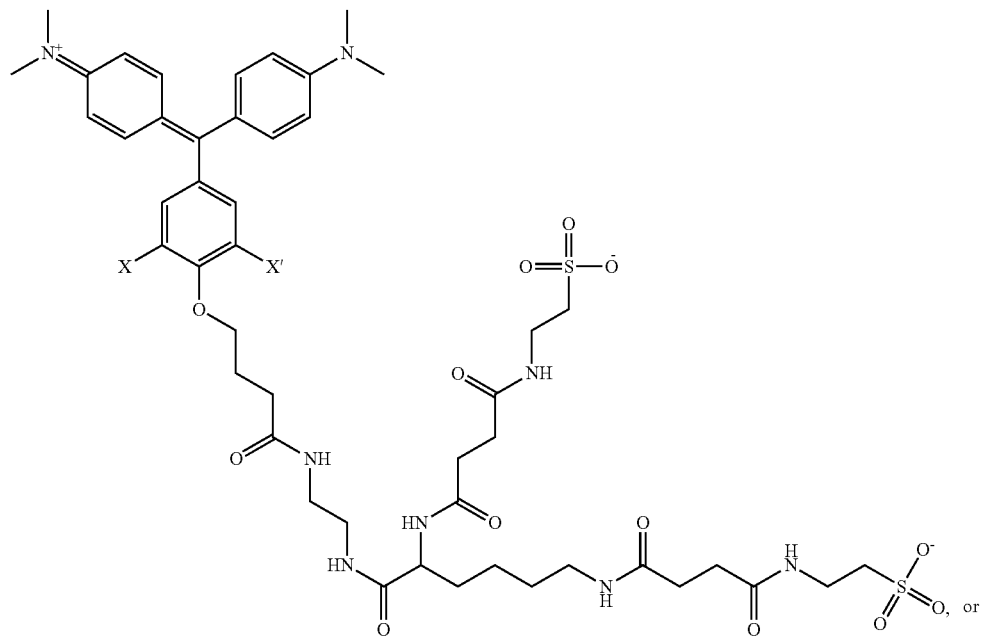

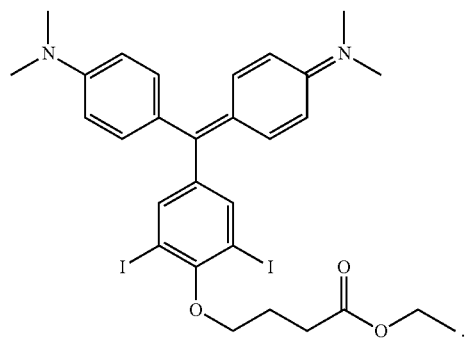

chite green derivative produces singlet oxygen when bound by the targeting activator and exposed to light at the excitation wavelength;
b. administering to the patient an effective amount of the heavy atom-modified malachite green derivative; and
c. exposing the cells to light at an excitation wavelength of the targeting activator-bound heavy atom-modified malachite green derivative, thereby killing the cells, wherein the heavy atom-modified malachite green derivative has the structure:

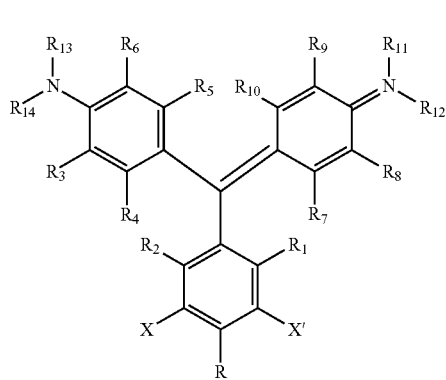

(Formula I)

where X and X' are, independently, heavy atoms, R1, R2, R3, R4, R5, R6, R7, R8, R9, and R10 are, independently H or F, R11, R12, R13 and R14 are, independently, methyl, H, aziridine or azetidine, wherein when R11, R12, R13, and/or R14 are aziridine or azetidine, R11 and R12 form a single ring and/or R13 and R14 form a single ring, and where R is selected from —H, —OH, —COO⁻, —SO₃⁻, —PO₄⁻, —NO₂, —NH₂, —N(CH₃)(R15), —OR16, alkyl, ether, polyether, PEG$_{1-30}$, —(C₁-C₄ alkyl)-R17, heterocycles containing N, S or O atoms, substituted acetylenic groups, cyano, and carbohydrate groups, wherein R15 and R16 are: straight- or branched-chain alkyl; straight or branched-chain C$_{1-6}$ alkyl; straight-chain or branched poly(C₁-C₄ alkyl amide); straight-chain or branched poly(C₁-C₄ alkyl amide) having from 2 to 6 amide moieties; poly(C₁-C₄ alkylene glycol); poly(C₁-C₄ alkylene glycol) having from 2 to 30 or from 2-10 C₁-C₄ alkylene glycol moieties; straight-chain or branched poly(C₁-C₄ alkyl amide):poly(C₁-C₄ alkylene glycol) diblock copolymer; straight-chain or branched poly(C₁-C₄ alkyl amide):poly(C₁-C₄ alkylene glycol) diblock copolymer having from 2 to 6 amide moieties and from 2 to 10 C₁-C₄ alkylene glycol moieties; sulfonyl or bis-sulfonyl-terminated straight-chain or branched poly(C₁-C₄ alkyl amide), optionally having from 2 to 6 amide moieties; bis-taurine branched poly(C₁-C₄ alkyl amide), optionally having from 2 to 6 amide moieties; ethyl butyrate; C$_{1-6}$ alkyl C$_{1-6}$ alkanoate; —(CH₂)$_n$—C(O)—O—(CH₂)$_m$—CH₃, where n=1-4 and m=0-3, and wherein R17 is selected from H, —OH, —COO⁻, —SO₃⁻, —PO₄⁻, —NO₂, or —NH₂.

Clause 36. The method of clause 35, in which R1, R2, R3, R4, R5, R6, R7, R8, R9, and R10 are H.

Clause 37. The method of clause 35 or 36, in which in which X and X' are independently Br, I, As, Se, Ga, Ge, or Sb.

Clause 38. The method of clause 35 or 36, in which X and X' are independently Br or I.

Clause 39. The method of clause 38, in which X and X' are I.

Clause 40. The method of clause 35 or 36, in which R11, R12, R13 and R14 are, independently, methyl or H, or R11, R12, R13 and R14 are methyl.

Clause 41. The method of any one of clauses 35-40, in which R is —OR16, and R16 is ethylbutyrate.

Clause 42. The method of clause 35, in which the heavy atom-modified malachite green derivative is:

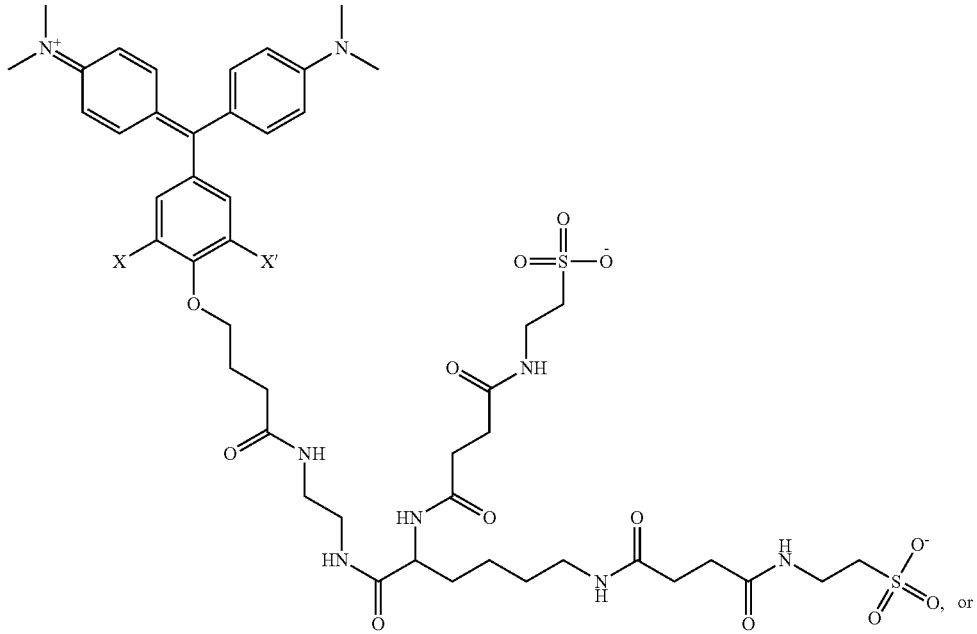

, or

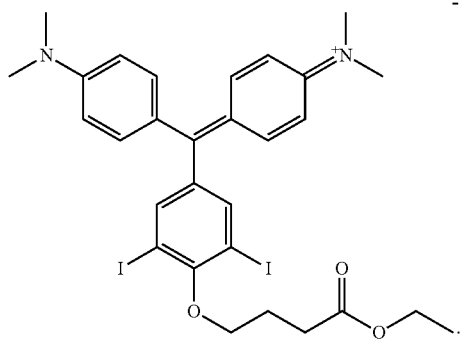

Clause 43. The method of any one of clauses 35-42, in which the activator moiety is fusion protein of an scFv and an affibody.

Clause 44. The method of clause 43, in which the scFv is an L5-MG scFv peptide, optionally SEQ ID NOS: 1-4.

Clause 45. The method of any one of clauses 35-44, in which the targeting moiety is selective for an epidermal growth factor receptor.

Clause 46. The method of clause 45, in which the epidermal growth factor receptor is HER1 (human epidermal growth factor receptor 1) or HER2 (human epidermal growth factor receptor 2).

Clause 47. The method of any of clauses 35-46, in which the targeting activator comprises a sequence selected from SEQ ID NOS: 1-4, 10-15, 17 and 18.

We claim:

1. A kit comprising:

a. a first vessel containing a heavy atom-modified malachite green derivative having the structure:

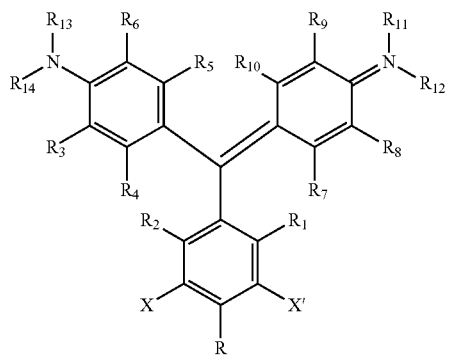

(Formula I)

where X and X' are, independently, Br, I, As, Se, Ga, Ge, or Sb, R1, R2, R3, R4, R5, R6, R7, R8, R9, and R10 are, independently H or F, R11, R12, R13 and R14 are, independently, methyl, H, aziridine or azetidine, wherein when R11, R12, R13, and/or R14 are aziridine or azetidine, R11 and R12 form a single ring and/or R13 and R14 form a single ring, and where R is selected from —OH, —COO⁻, —SO₃⁻, —PO₄⁻, —NO₂, —NH₂, —N(CH₃)(R15), —OR16, alkyl, ether, polyether, PEG$_{1-30}$, —(C$_1$-C$_4$ alkyl)-R17, heterocyles containing N, S or O atoms, substituted acetylenic groups, cyano, and carbohydrate groups, wherein R15 and R16 are: straight- or branched-chain alkyl; straight or branched-chain C$_{1-6}$ alkyl; straight-chain or branched poly(C$_1$-C$_4$ alkyl amide); straight-chain or branched poly(C$_1$-C$_4$ alkyl amide) having from 2 to 6 amide moieties; poly(C$_1$-C$_4$ alkylene glycol); poly(C$_1$-C$_4$ alkylene glycol) having from 2 to 30 or from 2-10 C$_1$-C$_4$ alkylene glycol moieties; straight-chain or branched poly(C$_1$-C$_4$ alkyl amide):poly(C$_1$-C$_4$ alkylene glycol) diblock copolymer; straight-chain or branched poly(C$_1$-C$_4$ alkyl amide):poly(C$_1$-C$_4$ alkylene glycol) diblock copolymer having from 2 to 6 amide moieties and from 2 to 10 C$_1$-C$_4$ alkylene glycol moieties; sulfonyl- or bis-sulfonyl-terminated straight-chain or branched poly(C$_1$-C$_4$ alkyl amide); bis-taurine-terminated branched poly(C$_1$-C$_4$ alkyl amide); ethyl butyrate; C$_1$-6 alkyl C$_{1-6}$ alkanoate; —(CH$_2$)n-C(O)—O—(CH$_2$)m-CH$_3$, where n=1-4 and m=0-3, and wherein R17 is selected from H, —OH, —COO—, —SO$_3$—, —PO$_4$—, —NO$_2$, or —NH$_2$; and b. a targeting activator in the first vessel or in a second vessel, comprising a targeting moiety that selectively binds a target compound of a cell and an activator moiety that selectively binds the heavy atom-modified malachite green derivative having an excitation wavelength so that the heavy atom-modified malachite green derivative produces singlet oxygen when bound by the targeting activator and exposed to light at the excitation wavelength.

2. The kit of claim 1, wherein R1, R2, R3, R4, R5, R6, R7, R8, R9, and R10 are H.

3. The kit of claim 1, wherein X and X' are independently Br or I.

4. The kit of claim 1, wherein X and X' are I.

5. The kit of claim 1, wherein R11, R12, R13 and R14 are, independently, methyl or H, or R11, R12, R13 and R14 are methyl.

6. The kit of claim 1, wherein R is —OR16, and R16 is ethylbutyrate.

7. The kit of claim 1, wherein the heavy atom-modified malachite green derivative has having the structure:

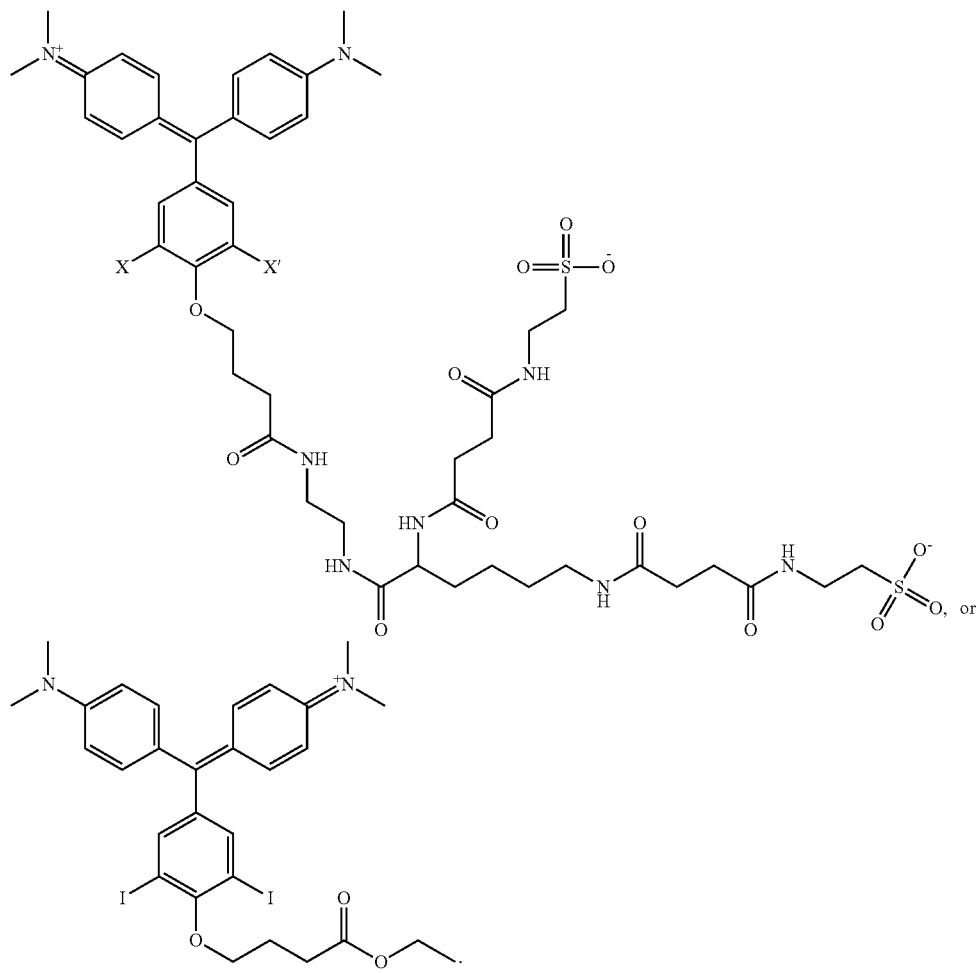

8. The kit of claim 1, wherein the targeting activator is a fusion protein of an scFv activator moiety and an affibody targeting moiety.

9. The kit of claim 8, wherein the scFv is an L5-MG scFv peptide.

10. The kit of claim 8, wherein the scFv is one of SEQ ID NOS: 1-4.

11. The kit of claim 1, wherein the targeting moiety is selective for an epidermal growth factor receptor.

12. The kit of claim 11, wherein the epidermal growth factor receptor is HER1 (human epidermal growth factor receptor 1) or HER2 (human epidermal growth factor receptor 2).

13. The kit of claim 1, wherein the targeting activator comprises a sequence selected from SEQ ID NOS: 1-4, 10-15, 17 and 18.

14. The kit of claim 1, wherein R is —OR16, and R16 is sulfonyl- or bis-sulfonyl-terminated straight-chain or branched poly($C_1$-$C_4$ alkyl amide) having from 2 to 6 amide moieties.

* * * * *

UNITED STATES PATENT AND TRADEMARK OFFICE
CERTIFICATE OF CORRECTION

PATENT NO.        : 10,946,098 B2
APPLICATION NO.   : 16/568886
DATED             : March 16, 2021
INVENTOR(S)       : Marcel P. Bruchez et al.

Page 1 of 1

It is certified that error appears in the above-identified patent and that said Letters Patent is hereby corrected as shown below:

In the Claims

Column 67, Line 57, Claim 1, delete "$PEG_{1\_30}$," and insert -- $PEG_{1-30}$, --

Column 67, Lines 57-58, Claim 1, delete "heterocyles" and insert -- heterocycles --

Column 68, Line 30, Claim 1, delete "$C_1$-6" and insert -- $C_{1-6}$ --

Column 68, Line 67, Claim 7, after "has" delete "having"

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*